United States Patent [19]

Levitt et al.

[11] Patent Number: 4,492,599

[45] Date of Patent: Jan. 8, 1985

[54] HERBICIDAL S-TRIAZINES

[75] Inventors: George Levitt, Wilmington; Wallace C. Petersen, Hockessin, both of Del.

[73] Assignee: E. I. Du Pont de Nemours and Company, Wilmington, Del.

[21] Appl. No.: 424,478

[22] Filed: Sep. 27, 1982

Related U.S. Application Data

[60] Division of Ser. No. 212,869, Dec. 4, 1980, Pat. No. 4,370,480, which is a continuation-in-part of Ser. No. 168,891, Jul. 17, 1980, abandoned, which is a continuation-in-part of Ser. No. 098,776, Nov. 30, 1979, abandoned.

[51] Int. Cl.[3] .................. C07D 251/46; C07D 405/12; A01N 43/68; A01N 43/70

[52] U.S. Cl. ........................................ 71/93; 544/113; 544/211; 544/212; 544/206; 544/207; 544/208; 544/209; 260/239.6

[58] Field of Search .................... 71/93; 544/113, 211, 544/212, 206, 207, 208, 209; 542/454; 260/239.6

[56] References Cited

U.S. PATENT DOCUMENTS

| | | | |
|---|---|---|---|
| 4,127,405 | 11/1978 | Levitt | 71/93 |
| 4,169,719 | 10/1979 | Levitt | 71/92 |
| 4,383,113 | 5/1983 | Levitt | 544/211 |
| 4,394,506 | 7/1983 | Levitt | 544/321 |

FOREIGN PATENT DOCUMENTS

| | | |
|---|---|---|
| 0044209 | 1/1982 | European Pat. Off. . |

*Primary Examiner*—John M. Ford

[57] ABSTRACT

This invention relates to novel urea and isourea compounds, agricultural compositions containing them and to their method of use as pre- and post- emergence herbicides and to plant growth regulants.

26 Claims, No Drawings

HERBICIDAL S-TRIAZINES

This application is a divisional application of our copending Ser. No. 212,869, filed Dec. 4, 1980, now U.S. Pat. No. 4,370,480, which is a continuation-in-part of our application Ser. No. 168,891, filed July 17, 1980, now abandoned, which is a continuation-in-part of our application Ser. No. 098,776, filed Nov. 30, 1979, now abandoned.

BACKGROUND OF THE INVENTION

This invention relates to ureas and isoureas having agricultural activity and in particular pre- and post-emergence herbicidal activity.

Netherlands Pat. No. 121,788 published Sept. 15, 1966, discloses the preparation of compounds of the following Formula and their use as general or selective herbicides:

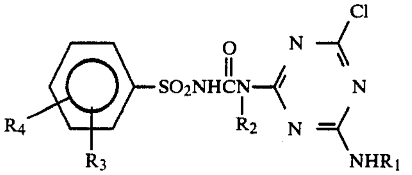

wherein $R_1$ and $R_2$ may independently be alkyl of 1–4 carbon atoms; and $R_3$ and $R_4$ may independently be hydrogen, chlorine or alkyl of 1–4 carbon atoms. U.S. Pat. No. 3,637,366 discloses compounds having the formula:

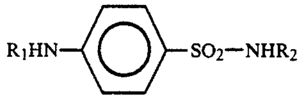

wherein $R_1$ is hydrogen or lower saturated aliphatic acyl and $R_2$ is hydrogen, 2-pyrimidinyl, pyridyl, amidino, acetyl or carbamoyl.

The disclosed compounds are said to provide control of crabgrass, cress, endive, clover and *Poa annua*.

French Pat. No. 1,468,747 discloses the following para-substituted phenylsulfonamides as being useful as antidiabetic agents:

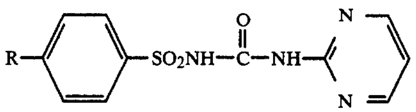

wherein R=H, halogen, $CF_3$ or alkyl.

Logemann et al. Chem Ab., 53, 18052 g (1959), disclose a number of sulfonamides, including uracil derivatives and those having the formula:

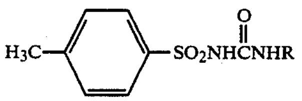

wherein

R is butyl, phenyl, or

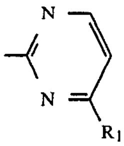

and $R_1$ is hydrogen or methyl.

When tested for hypoglycemic effect in rats (oral doses of 25 mg/100 g), the compounds in which R is butyl and phenyl were most potent. The others were of low potency or inactive.

Wojciechowski, J. Acta. Polon. Pharm 19, p. 121–5 (1962) [Chem. Ab., 59 1633 e] describes the synthesis of N-[(2,6-dimethoxypyrimidin-4-yl)amino-carbonyl]-4-methylbenzenesulfonamide:

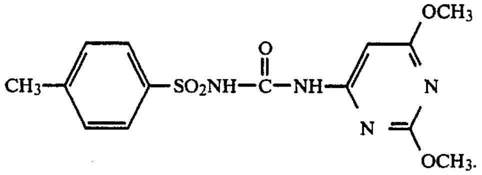

Based upon similarity to a known compound, the author speculated that the foregoing compound might have a hypoglycemic activity.

U.S. Pat. No. 3,823,007 discloses isourea salts as herbicides:

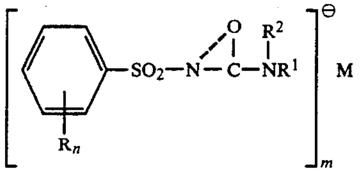

wherein $R_n$ is chloro, bromo, iodo, cyano, alkyl alkoxy, nitro, amino or

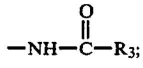

$R^3$ is hydrogen or alkyl;

n is the integer one to three;

m is the integer one or two;

M is of alkali metal, alkaline earth metal or ammonium;

$R^1$ and $R^2$ are each independently hydrogen, alkyl, alkoxy, alkynyl, phenyl, substituted phenyl having a maximum of three substituents said substituents being alkyl bromine, chlorine, alkoxy, phenoxy, mono and dihalogenated phenoxy said halogen being chlorine or bromine, or the group

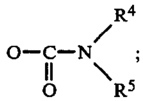 ; and and $R^4$ and $R^5$ are each independently hydrogen or alkyl.

U.S. Pat. No. 3,714,209 discloses the isopropylidineaminoethanol salt of p-nitrobenzenesulfonylisourea as a herbicide:

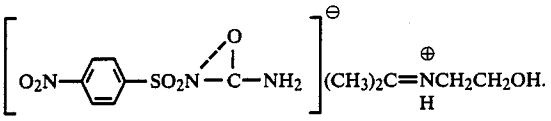

Substituted-pyrimidinyl sulfonylureas of the following formula, which are also para-substituted on the phenyl ring, are disclosed in Farmco Ed. Sci., 12, 586 (1957) [Chem. Ab., 53, 18052 g (1959]:

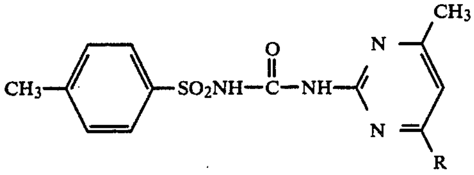

wherein R=H or $CH_3$.

The presence of undesired vegetation causes substantial damage to useful crops, especially agricultural products that satisfy man's basic food and fiber needs, such as cotton, rice, corn, wheat, and the like. The current population explosion and concomitant world food and fiber shortage demand improvements in the efficiency of producing these crops. Preventing or minimizing loss of a portion of such valuable crops by killing, or inhibiting the growth of undesired vegetation is one way of improving this efficiency. A wide variety of materials useful for killing or inhibiting (controlling) the growth of undesired vegetation is available; such materials are commonly referred to as herbicides. The need still exists however, for more effective herbicides.

SUMMARY OF THE INVENTION

This invention relates to novel ureas and isoureas of Formula I, to agricultural compositions containing them and to their method of use as pre- and post-emergence herbicides and to plant growth regulants.

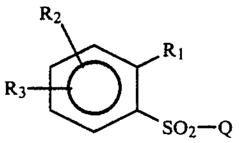

I where $R_1$ is

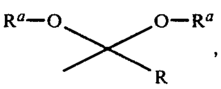

,

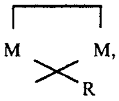

,

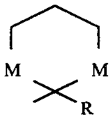

or

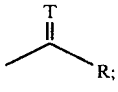

M=0 or $S(0)_G$;

G=0 or 2;

$R^a$ is $CH_3$ or $CH_3CH_2$;

R=H; $C_1$-$C_{12}$ alkyl; $C_2$-$C_6$ alkenyl; $C_2$-$C_6$ alkynyl; $C_1$-$C_4$ alkyl substituted with one to four substituents selected from 0-3 F, 0-3 Cl, 0-3 Br, 0-2 $OCH_3$, 0-1 cyano, 0-1 $CO_2R_1'$ where $R_1'$ is $C_1$-$C_3$ alkyl; $CO_2R_1'$; $C_2$-$C_4$ alkenyl substituted with 1-3 Cl; $C_3$-$C_6$ cycloalkyl; $C_5$-$C_6$ cycloalkenyl; $C_5$-$C_6$ cycloalkyl substituted with substituents selected from 1-3 $CH_3$ or one of $CH_3CH_2$, Cl, $OCH_3$; $C_4$-$C_7$ cycloalkylalkyl;

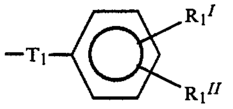

where $T_1$ is

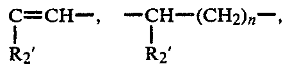

or a single bond;

where $R_2'$ is H or $CH_3$, n is 0 or 1;

$R_1^I$ and $R_1^{II}$ are independently H, $CH_3$, Cl or $OCH_3$;

T=O or

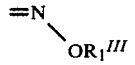

where $R_1^{III}$ is H, $C_1$-$C_4$ alkyl or $C_3$-$C_4$ alkenyl;

$R_2$=H, F, Cl, Br, $C_1$-$C_3$ alkyl, $NO_2$, $SO_2CH_3$, $OCH_3$, $SCH_3$, $CF_3$ or $N(CH_3)_2$;

$R_3$=H, F, Cl, Br or $CH_3$;

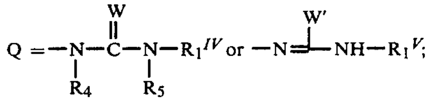

where $R_4$=H or $CH_3$;

$R_5$=H, $CH_3$ or $OCH_3$;

W=O or S;

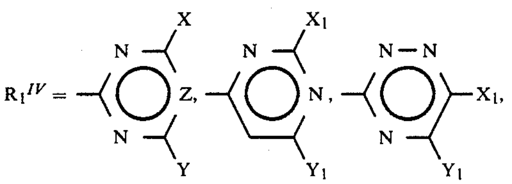

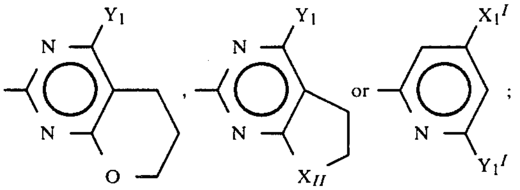

where

Z=CH, N, C—F, C—Cl, C—Br, C—$CH_3$, C—$OCH_3$, C—$CH_2CH_3$ or C—$CH_2CH_2Cl$;

X=H, Cl, —$CH_3$, —$OCH_3$, —$OCH_2CH_3$ or —$OCH_2CH_2OCH_3$;

Y=H; Cl; $C_1$-$C_4$ alkyl; $C_1$-$C_4$ alkyl substituted with —$OCH_3$, —$OC_2H_5$, —CN, —$CO_2CH_3$, —$CO_2C_2H_5$ or 1-3 atoms of F, Cl, Br; $C_3$-$C_4$ alkenyl; —$CH_2C{\equiv}CR_6$ where $R_6$ is H, —$CH_3$, —$CH_2Cl$; —A—$(CH_2)_{n'}$—$A_1$—($C_1$-$C_3$ alkyl) where n' is 2 or 3, A is O or S and $A_1$ is O, S or $SO_2$;

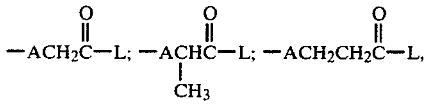

where

L is OH, —$NH_2$,

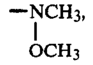

—NH($C_1$-$C_4$ alkyl), —N($C_1$-$C_4$ alkyl)$_2$, $C_1$-$C_6$ alkoxy; SCN; —$N_3$; $NR_7R_8$ where $R_7$ is H or $CH_3$ and $R_8$ is H, —$OCH_3$, $C_1$-$C_4$ alkyl, $C_3$-$C_6$ cycloalkyl, $C_1$-$C_4$ alkyl substituted with —CN or —$CO_2CH_3$ or $CO_2C_2H_5$, $C_3$-$C_4$ alkenyl, or $C_2$-$C_3$ alkyl substituted with $OCH_3$ or $OC_2H_5$, or $R_7$ and $R_8$ can be taken together to form —$CH_2CH_2CH_2CH_2$— or —$CH_2CH_2OCH_2CH_2$—; —O—$R_9$ where $R_9$ is $C_1$-$C_4$ alkyl, $C_2$-$C_4$ alkyl substituted with 1-3 atoms of F, Cl or Br, $C_1$-$C_4$ alkyl substituted with cyano, $C_3$-$C_4$ alkenyl, —$CH_2C{\equiv}CR_6$, where $R_6$ is as previously defined,

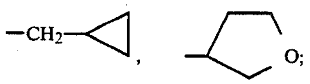

—$SR_{10}$ where $R_{10}$ is $C_1$-$C_4$ alkyl, $C_1$-$C_2$ alkyl substituted with CN, allyl or propargyl;

$X_1$=H, Cl, $OCH_3$, $OCH_2CH_3$ or $CH_3$;

$Y_1$=H, $OCH_3$ or $CH_3$;

$X_{II}$=0 or $CH_2$;

$X_1^I$ and $Y_1^I$=$CH_3$ or $OCH_3$;

W'=$SR_{11}$ or $OR_{12}$; where $R_{11}$ and $R_{12}$=$C_1$-$C_{12}$ alkyl; $C_3$-$C_4$ alkenyl; $CH_2CH_2OCH_3$; $CH_2CH_2OCH_2CH_3$; $CH_2CH_2CH_2OCH_3$; benzyl;

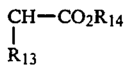

where $R_{13}$ is H or $CH_3$, $R_{14}$ is $C_1$-$C_4$ alkyl;

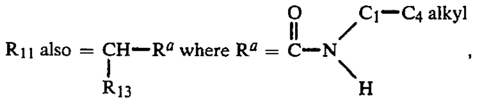

-continued

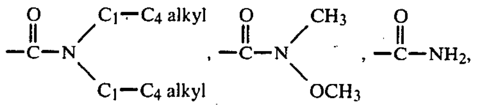

CN, $C_2$-$C_4$ alkenyl, $C_2$-$C_4$ alkynyl, phenyl and phenyl substituted with $CH_3$ or Cl;

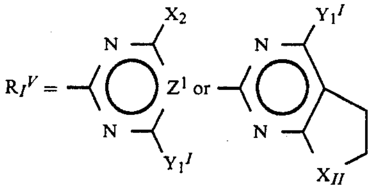

where $Z^I$=CH or N;

$Y_1^I$=$CH_3$ or $OCH_3$;

$X_2$=$CH_3$; $C_1$-$C_4$ alkoxy; $O(CH_2)_{n''}OR_{15}$ where n" is 1-3, $R_{15}$ is $C_1$-$C_3$ alkyl; $OCHR_{16}CO_2R_{17}$ where $R_{16}$ is H or $CH_3$; $OCH_2CF_3$ or $OCH_2CCl_3$; $R_{17}$ is $C_1$-$C_3$ alkyl; and $X_{II}$=O or $CH_2$;

with the provisos that:

(1) when Y contains ≧4 carbon atoms, R contains ≦4 carbon atoms;

(2) when X is Cl, then Y is Cl;

(3) when X and Y are both H, then R is ≦4 carbon atoms;

(4) when Z≠N or CH, then X=H, $CH_3$, $OCH_3$ or Cl and Y=H, $CH_3$ or $OCH_3$;

(5) both $X_1$ and $Y_1$ cannot be H; and (6) when

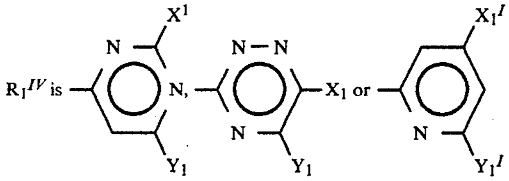

then $R_4$ and $R_5$ are hydrogen and R≦5 carbon atoms;

(7) when T is =N—$OR_1^{III}$, then R contains ≦5 carbon atoms;

and their agriculturally suitable salts.

More preferred are:

(1) A compound of the generic scope where $R_4$ and $R_5$ are H and W is oxygen;

(2) A compound of Preferred 1 where $R_2$ is H, F, Cl, Br, $C_1$-$C_3$ alkyl, $OCH_3$ and $R_3$ is H in the position para to the sulfonyl group;

(3) A compound of Preferred 2 where

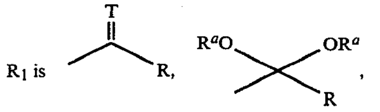

-continued

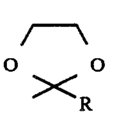 or 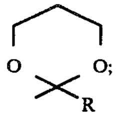

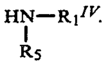

(4) A compound of Preferred 3 where R is H, $C_1$–$C_6$ alkyl, $C_2$–$C_6$ alkenyl, $C_3$–$C_6$ cycloalkyl, or

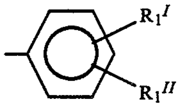

where $R_1^{I}$ and $R_1^{II}$ are independently H, $CH_3$, Cl or $OCH_3$;

(5) A compound of Preferred 4 where X is $CH_3$, $OCH_3$ or $OCH_2CH_3$ and Y is H, $C_1$–$C_3$ alkyl, $CH_2OCH_3$, $CH_2OCH_2CH_3$, —$OCH_2CO_2$—($C_1$—$C_2$ alkyl),

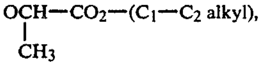

O—($C_1$–$C_3$ alkyl), O—($C_3$–$C_4$ alkenyl), $NR_7R_8$ where $R_7$ is H or $CH_3$ or $R_8$ is $C_1$–$C_3$ alkyl, and Z=CH or N;

(6) A compound of Preferred 5 where

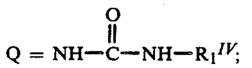

(7) A compound of Preferred 6 where T=O; and (8) A compound of Preferred 7 where $R_1$ is 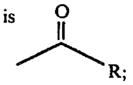

(9) A compound of Preferred 8 where R is H or $C_1$–$C_4$ alkyl.

Specifically preferred for their outstanding herbicidal and plant growth regulant activity are:

2-acetyl-N-[(4,6-dimethoxypyrimidin-2-yl)aminocarbonyl]benzenesulfonamide;

2-acetyl-N-[(4,6-dimethylpyrimidin-2-yl)aminocarbonyl]benzenesulfonamide;

2-acetyl-N-[(4-methoxy-6-methyl-1,3,5-triazin-2-yl)aminocarbonyl]benzenesulfonamide;

2-acetyl-N-[(4-methoxy-6-methylpyrimidin-2-yl)aminocarbonyl]benzenesulfonamide;

2-formyl-N-[(4,6-dimethylpyrimidin-2-yl)aminocarbonyl]benzenesulfonamide; and 2-formyl-N-[(4,6-dimethoxypyrimidin-2-yl)aminocarbonyl]benzenesulfonamide.

Synthesis

Many of the compounds of Formula I, where W=O, may be prepared as shown in Equation I by reaction of an appropriately substituted benzenesulfonylisocyanate, containing an o-ketone functional group protected as the dithiane, with an appropriate heterocyclic compound described as Equation 1

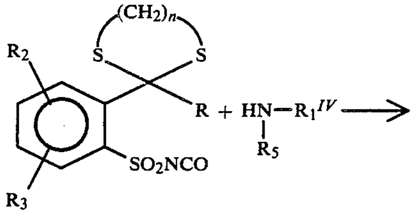

II n = 2 or 3

III'

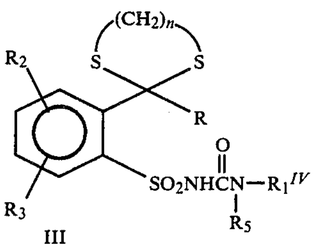

III

The reaction of Equation 1 is best carried out in inert aprotic organic solvents such as methylene chloride, tetrahydrofuran or acetonitrile, at ambient pressure and temperature. The mode of addition is not critical; however, it is often convenient to add the sulfonyl isocyanate to a stirred suspension of amine III'. Since such isocyanates are liquids, low melting solids or are readily soluble in solvents such as those listed above, their addition can be easily controlled.

The reaction is generally exothermic. In some cases, the desired product is soluble in the warm reaction medium and on cooling crystallizes in pure form. Other products which are soluble in the reaction medium are isolated by evaporation of the solvent, trituration of the solid residue with solvents such as 1-chlorobutane or ethyl ether, and filtration.

The dithiane can be converted to the ketone by treatment with mercury salts in aqueous acetone as shown in Equation 2, according to the procedures reviewed by D. S. Toabell and D. P. Harnish, Chem., Rev., 49, 67 (1950).

Equation 2

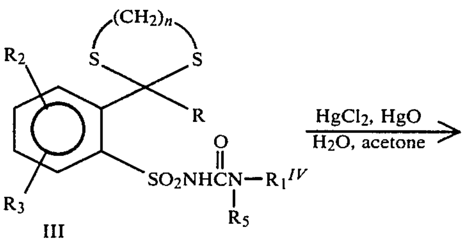

III n = 2 or 3

-continued

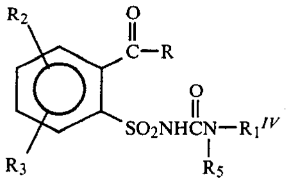

IV

The conversion of alkylsulfides to sulfones is often accomplished by the use of a peracid in an inert solvent as described in The Organic Chemistry of Sulfur, Sutter, Wiley, p. 660.

Thus, o-(2-substituted-1,3-dithiacycloalkan-2-yl)benzenesulfonylisocyanates, II, are important intermediates for the preparation of the compounds of this invention. The synthesis of these compounds is described in Equation 3.

Equation 3

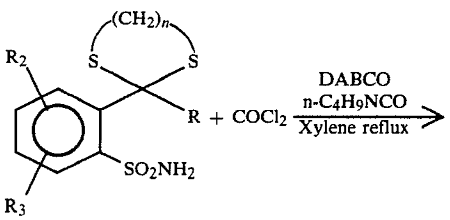

V
n = 2 or 3

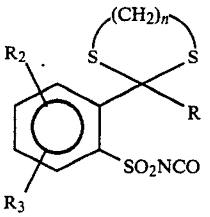

II

The above reaction is carried out by heating a mixture of the appropriate sulfonamide (V), an alkyl isocyanate such as butyl isocyanate and a catalytic amount of 1,4-diaza[2,2,2]bicyclooctane (DABCO) in xylene or other inert solvent of sufficiently high boiling point (e.g. >135°) to approximately 135°. Phosgene is added to the mixture until an excess of phosgene is present as indicated by a drop in the boiling point. (The mixture is heated further to drive off the excess phosgene). After the mixture is cooled and filtered to remove a small amount of insoluble by-products, the solvent and alkyl isocyanate are distilled off in-vacuo leaving a residue which is the crude sulfonylisocyanate (II).

The sulfonylisocyanates (II) can also be prepared, as shown in Equation 4, by first preparing the n-butylsulfonylureas (VI) and subsequently reacting them with phosgene.

Equation 4

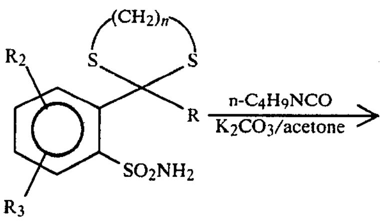

V
n = 2 or 3

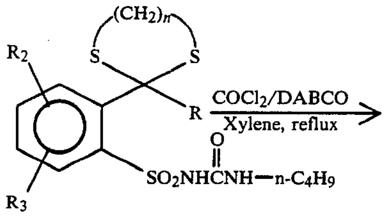

VI
n = 2 or 3

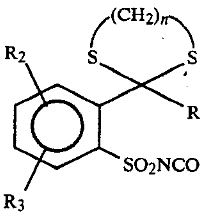

II
n = 2 or 3

The compounds (VI) are conveniently prepared by stirring a mixture of the sulfonamides, (V), anhydrous potassium carbonate and n-butylisocyanate in acetone or methyl ethyl ketone at 25°-80° C. until all of the isocyanate has reacted. The products are isolated by quenching in dilute mineral acid or by distilling the solvent and recrystallizing the residue. The compounds (VI) are treated with phosgene and a catalytic amount of DABCO in refluxing xylene or chlorobenzene in a manner analogous to that described in Equation 3.

The o-(2-substituted-1,3-dithiacycloalkan-2-yl)benzenesulfonamides V bearing substituents $R_2$ and $R_3$ compatible with tert-butyl hypochlorite are prepared from the corresponding anilines VII as described in Equation 5. Following the procedures of P. G. Gassman and H. R. Drewes, *J. Am. Chem. Soc.*, 96, 3002 (1974), the aniline VII is treated sequentially in 3:1 acetonitrile-methylene chloride, at −40° C. with tert-butyl hypochlorite, the dithiane VIII, and sodium methoxide to provide the o-substituted aniline IX. The required dithanes VIII are readily available from the corresponding aldehydes or by alkylation of 1,3-dithiane as described by D. Seebach and E. J. Corey, *J. Org. Chem.*, 40, 231 (1975).

Equation 5

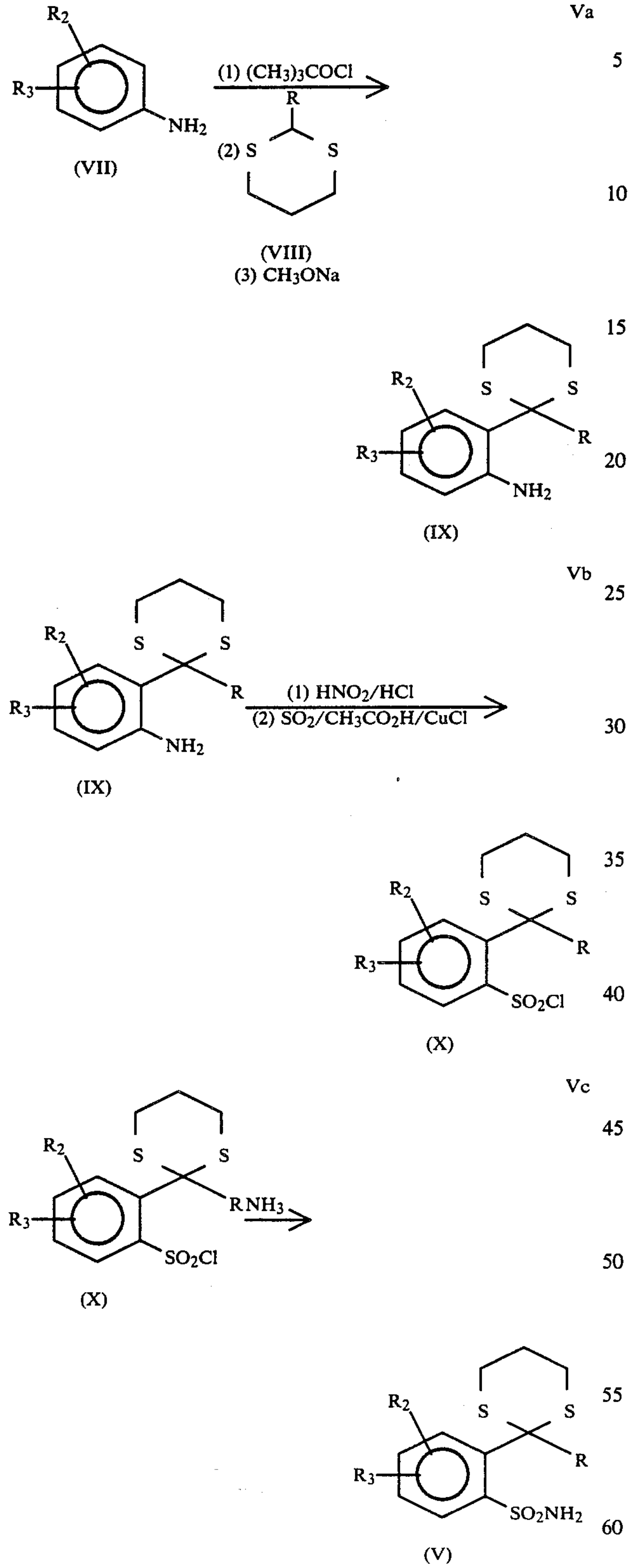

The diazotization and coupling with sulfur dioxide, described in step Vb is accomplished in the following manner. A solution of the o-substituted aniline of Formula IX in a mixture of concentrated hydrochloric acid and glacial acetic acid is treated with a solution of sodium nitrite in water at −5° to 0°. After stirring for 10–15 minutes at 0° to insure complete diazotization, this solution is added to a mixture of an excess of sulfur dioxide, and a catalytic amount of cuprous chloride in glacial acetic acid at 0°–5°. The temperature is kept at 0°–5° for ¼ to 1 hour then raised to 20°–25° and held at that temperature for 2–4 hours. This solution is then poured into a large excess of ice water. The sulfonyl chloride products, X, can be isolated by filtration or by extraction into a solvent such as ethyl ether or methylene chloride followed by evaporation of the solvent.

The amination described in step Vc is conveniently carried out by treating a solution of the sulfonyl chloride of Formula X with an excess of anhydrous ammonia in a solvent such as ethyl ether or methylene chloride at 0°–25°. If the product sulfonamide, V, is insoluble, it may be isolated by filtration followed by washing out the salts with water. If the product sulfonamide is soluble in the reaction solution, it may be isolated by filtering off the precipitated ammonium chloride and evaporation of the solvent.

Certain compounds of Formula I are prepared by the reaction of an excess of organolithium compound with a carboxylic acid derivative of Formula XXVI.

Equation 6

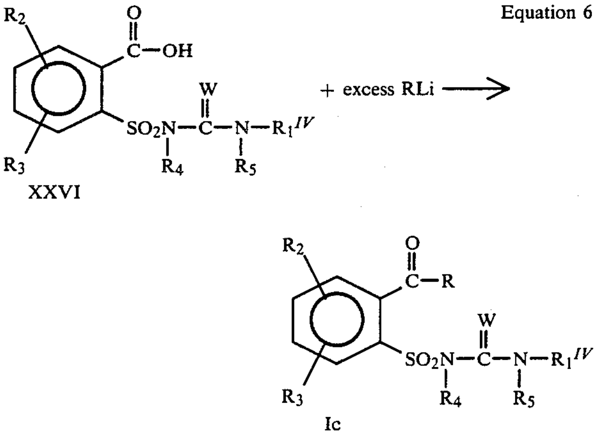

Compounds of Formula XXVI are restricted to structures in which the substituents $R_2$, $R_3$, Z, X, Y, $X_1$, $Y_1$, $X_1^I$ and $Y_1^I$ contain no displaceable halogens; carboxylic acids, esters or amides; $NO_2$; CN; SCN or $N_3$.

An excess of organolithium compound in a suitable solvent such as diethyl ether, hexane, pentane, or benzene is added to a solution or slurry of XXVI in a similar solvent at temperatures between −100° and 0° C. The mixture is allowed to warm to room temperature and stir for 30 minutes. Aqueous acid is then added and the compound Ic is extracted into a suitable solvent to free it from salts followed by evaporation of the solvent. Purification is done by chromatography on silica gel.

The synthesis of a wide variety of organolithium compounds by many different procedures is known in the art. A summary of methods with bibliography is contained in *Organo-Metallic Compounds*, G. E. Coates, John Wiley and Sons, 1960, p. 3–21.

Compounds of Structure XXVI are prepared according to Equation 7.

Equation 7

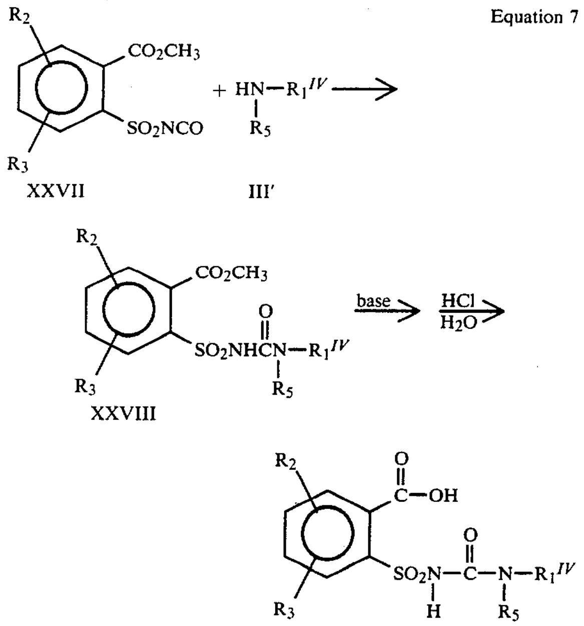

XXVII III'

XXVIII

XXVI

The preparation of compounds XVII from the corresponding sulfonamides is carried out in a manner similar to the preparation of compound II. The reaction of XXVII with III' is carried out in a manner similar to the preparation of III. Compounds of Formula XXVI wherein Z does not equal N are prepared by dissolving compound XXVIII in an aqueous methanol or ethanol solution containing KOH. The mixture is stirred at 0°–25° C. for 6–24 hours. The reaction yields the soluble alkali metal salt of the carboxylic acid. The salt is converted to the acid form by addition of strong mineral acids causing the carboxylic acid (XXVI) to precipitate.

Those compounds of Formula XXVI wherein Z is equal to N are prepared by dissolving compound XXVIII in a solution of potassium tert-butoxide in dimethyl sulfoxide. The mixture is stirred at ambient tem- Equation 9

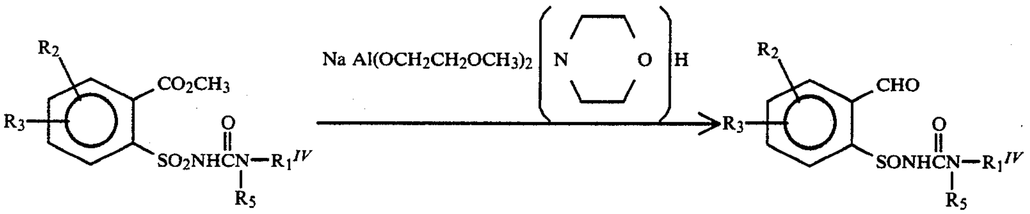

XXVIII XIV perature for three hours and then poured into a large volume of water. Acidification with mineral acids causes the carboxylic acid (XXVI) to precipitate.

Compounds of Formula I wherein T is $=N-OR_1^{III}$ are prepared by standard oximation procedures as outlined in *Preparative Organic Chemistry,* G. Hilgetag and A. Martini, Ed., John Wiley and Sons, p. 513.

Ketals and acetals of Formula XIII a-c are prepared by an acid-catalyzed exchange reaction with the appropriate acetone ketal XII a-c according to the teachings of N. B. Lorette and W. L. Howard, *J. Org. Chem.,* 25, 521 (1960) as shown in Equation 8.

The aldehyde or ketone of Formula XI is treated with the appropriate acetone ketal XII with or without a cosolvent such as dichloromethane and an acid catalyst such as p-toluenesulfonic acid or boron trifluoride at, or above, ambient temperature. The acid catalyst is removed by washing with a dilute aqueous solution of sodium bicarbonate and the solvents are removed by distillation at reduced pressure.

Equation 8

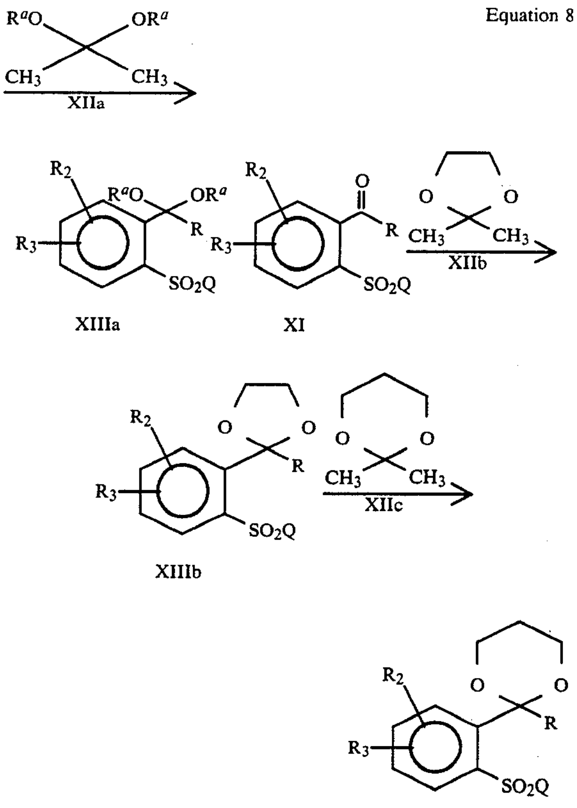

XIIa

XIIIa XI XIIb

XIIIb XIIc

XIIIc

Aldehydes of Formula XIV wherein $R_2$ does not equal $-NO_2$ are prepared by the procedure of Equation 9.

Following the procedure of R. Kanazawa and T. Tokoroyama, *Synthesis,* 526 (1976), a solution of sodium bis-(2-methoxyethoxy)aluminum hydride in THF is reacted with one equivalent of morpholine. To this solution at −40° C. is added a methyl ester of Formula XXVIII and the solution is allowed to warm to 25° C. The product is isolated by addition of aqueous acid and extraction into ether or methylene chloride. Evaporation of the solvent and crystallization or column chromatography on silica gel affords the pure aldehyde, XIV.

Aldehydes of Formula XIV may also be prepared from the esters of Formula XXVIII by treatment with diisobutylaluminum hydride according to the procedures of E. Winterfeldt, *Synthesis,* 617 (1975).

Aldehydes of Formula XIV wherein $R_3$ and $R_5$ are H, $R_2$ does not equal $-SO_2CH_3$, $-OCH_3$, $-SCH_3$ or $-N(CH_3)_2$ and $R_1^{IV}$ is 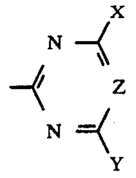 or 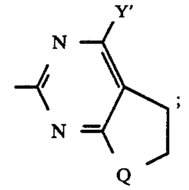 ;

- X is H, Cl, Br, $CH_3$, $CH_3CH_2$, $C_1$-$C_3$ alkoxy, $CF_3$, $CH_3S$ or $CH_3OCH_2$;
- Y is $CH_3$ or $CH_3O$;
- Z is N, CH, C—Cl, C—Br, C—$CH_3$, —C—$CH_2CH_3$ or —C—$CH_2CH_2Cl$;
- Y' is H, $CH_3$, $OCH_3$ or Cl;
- Q is O or $CH_2$;

can also be prepared by the procedure outlined in Equation 9'.

Equation 9'

IX'a

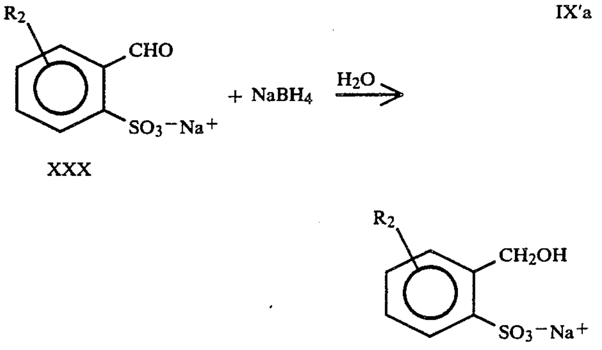

XXX

XXXI

IX'b

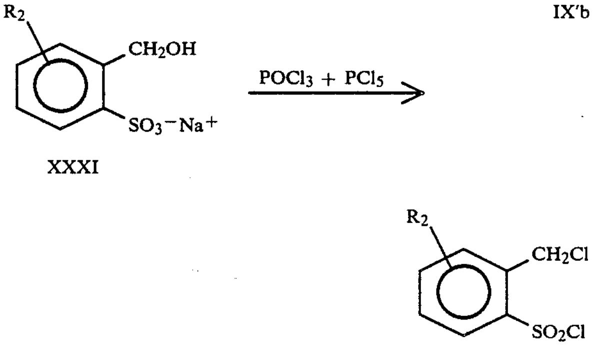

XXXI

XXXII

IX'c

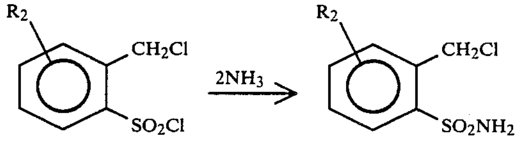

XXXII XXXIII

-continued

Equation 9'

IX'd

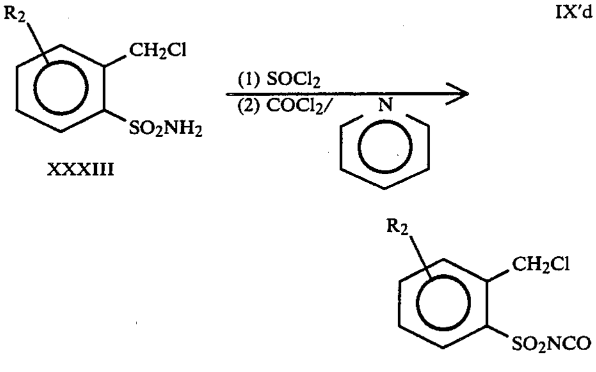

XXXIII

XXXIV

IX'e

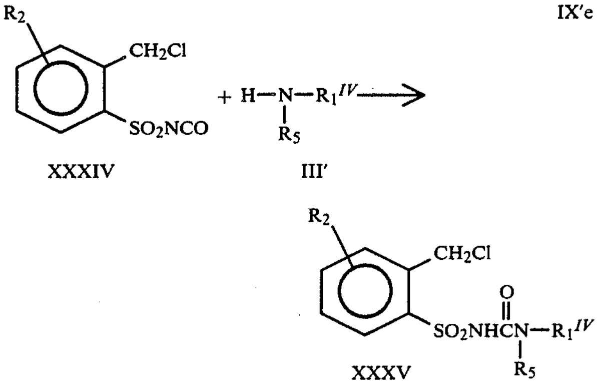

XXXIV III'

XXXV

IX'f

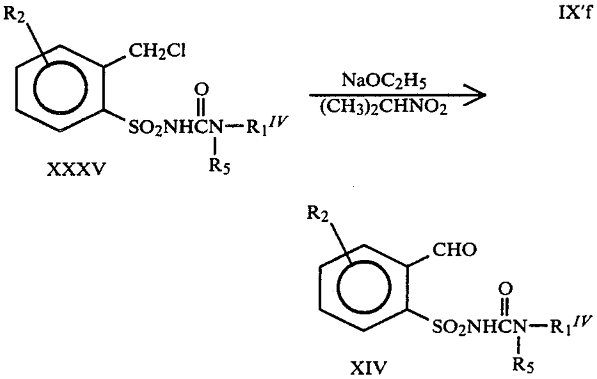

XXXV

XIV

Following the teachings of N. Kornblum, *Angew. Chem., Int. Ed.,* 14, 734 (1975), the chloromethyl compound XXXV is treated in step IX'f with the sodium salt of 2-nitropropane in ethanol at reflux for 4 hours. The solvent is removed under reduced pressure and the crude product is dissolved in water. Acidificaiton causes the crude aldehyde XIV to precipitate. The product is purified by chromatography or recrystallization.

The required chloromethyl compound XXXV is synthesized as outlined in steps IX'a through IX'e. The aldehyde XXX is first reduced to the corresponding alcohol XXXI using sodium borohydride under standard conditions.

The chlorination described in step IX'b is accomplished using the procedure of J. F. King, et al., *Can. J. Chem.,* 49, 943 (1971). The alcohol is dissovled in phosphorus oxychloride and contacted with portions of phosphorus pentachloride. After heating at 70° C. for 2 days, the phosphorus oxychloride is removed at reduced pressure. The crude product is dissolved in toluene, washed with water, and distilled to provide the pure compound XXXII.

The amination procedure of step IX'c is analogous to that previously described for the preparation of compound V. The recrystallized sulfonamide XXXIII is refluxed with thionyl chloride for 36 hours. After removal of the thionyl chloride at reduced pressure, toluene and pyridine are added and the mixture is heated to 70° C. The solution is treated with excess phosgene for 2 hours.

Removal of the solvent affords the crude sulfonylisocyanate XXXIV which is immediately dissolved in acetonitrile and contacted with the amine III'. After stirring at ambient temperature for 16 hours, the resulting solid is filtered and washed with acetonitrile. The solid is then dissolved in dilute aqueous sodium hydroxide, filtered, and reprecipitated by the addition of dilute hydrochloric acid to provide the purified chloromethyl compound XXXV.

As shown in Equation 10, compounds of Formula I, wherein $R_4=CH_3$; $R_5-H$; and W=S, are prepared by the reaction of an appropriately substituted o-carbonylbenzenesulfonamide with the appropriate heterocyclic isothiocyanate of Formula $SCN—R_1^{IV}$.

Equation 10

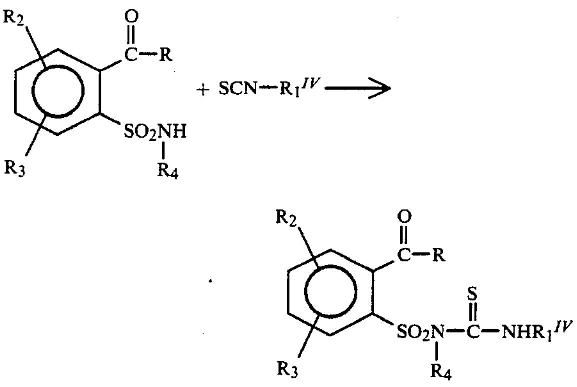

The reaction of Equation 10 is best carried out by dissolving or suspending the sulfonamide and isothiocyanate in a polar solvent such as acetone, acetonitrile, ethyl acetate or methyl ethyl ketone, adding an equivalent of a base such as potassium carbonate and stirring the mixture at ambient temperature up to the reflux temperature for one to twentyfour hours. In some cases, the product precipitates from the reaction mixture and can be removed by filtration. The product is stirred in dilute mineral acid, filtered and washed with cold water. If the product does not precipitate from the reaction mixture it can be isolated by evaporation of the solvent, trituration of the residue with dilute mineral acid and filtering off the insoluble product.

The heterocyclic isothiocyanates which are used in the procedure of Equation 10 are prepared, for example, according to the method of Japan Patent Application Pub: Kokai No. 51-143686, June 5, 1976, or that of W. Abraham and G. Barnikow, Tetrahedron 29, 691-7 (1973).

As shown in Equation 11, compounds of Formula I, wherein W is O or S; $R_4=CH_3$; $R_5=CH_3$ or $OCH_3$, can also be prepared by the reaction of an appropriately substituted sulfonyl-N-methylcarbamyl chloride or sulfonyl-N-methylthiocarbamyl chloride of Formula XV with an appropriate aminoheterocycle of Formula III':

Equation 11

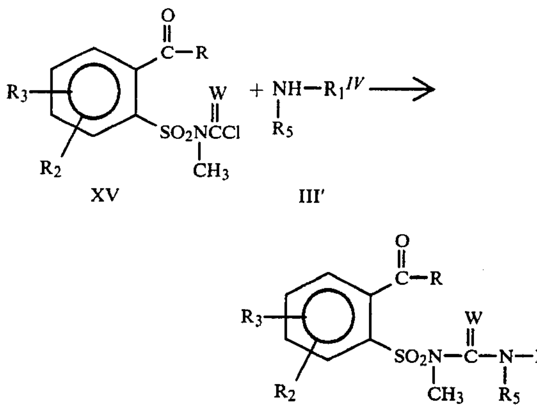

XV III'

$R_5 = CH_3$ or $OCH_3$

The preparation of ureas and thioureas, like those of Formula I, from amines and carbamyl chlorides and thiocarbamyl chlorides is well known to the art. The reaction can best be carried out by adding equivalent amounts of the chloride XV and amine III' to an inert organic solvent, such as tetrahydrofuran, xylene, or methylene chloride, in the presence of an acid acceptor, such as triethylamine, pyridine, or sodium carbonate employing temperatures from 20°-130°. Soluble products can be isolated by filtering off the precipitated salts and concentration of the filtrate. Insoluble products can be filtered off and washed free of salts with water.

Certain compounds of Formula I wherein W=O and $R_5=H$ may be prepared by reacting the appropriately substituted benzenesulfonamide with a heterocyclic isocyanate as shown in Equation 11'.

Equation 11'

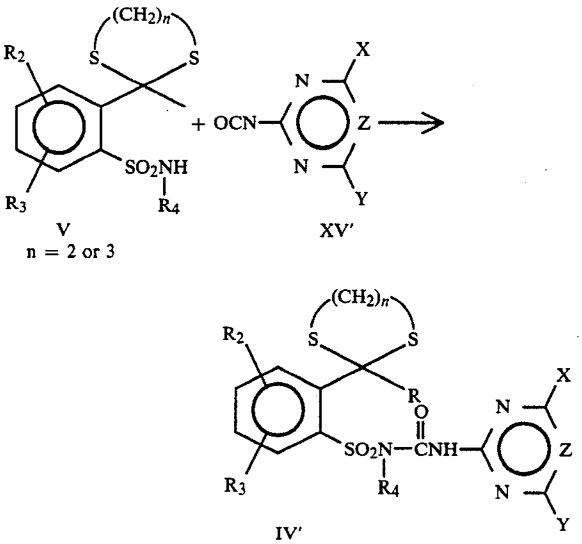

V XV' n = 2 or 3

IV'

In Equation 11', Z is N or CH and X=Y=Cl. Compound IV' is converted to compounds of Formula I by treatment with an alkoxide included in the description of X and Y. The reaction of Equation 11' is best carried out by dissolving or suspending the sulfonamide and heterocyclic isocyanate in an inert solvent such as acetonitrile, tetrahydrofuran (THF), toluene, acetone or methyl ethyl ketone in the presence of a base catalyst such as 1,4-diazobicyclo[2.2.2]octane (DABCO), potassium carbonate, sodium hydride, or potassium tert-butoxide. The reaction is performed at 25° to 100° for 1 to 24 hours. The product generally can be recovered by cooling the reaction mixture and filtration.

The displacement of halogen from halopyrimidines and halotriazines by alkoxide is known in the art, *The Chemistry of Heterocyclic Compounds* 16, 201 (1962) Interscience Publishers, A. Weissberger, U.S. Pat. No. 3,972,882. The preparation of haloheterocyclic isocyanates by reaction of haloheterocyclic amines with phosgene or oxalyl chloride has been reported [Swiss Pat. No. 579,062: U.S. Pat. Nos. 3,919,228 and 3,732,223; Angew, Chem. Int. Ed., 10 #6 (1971)].

The chlorides of Formula XV can be prepared by phosgenation or thiophosgenation of N-alkylsulfonamide salts. The sulfonamide salt is added to an excess of phosgene or thiophosgene in an inert organic solvent, such as tetrahydrofuran, toluene, or xylene, whereupon, after removal of the excess phosgene, the chloride XV can be isolated or reacted in-situ with the amine III'.

Compounds of Formula I, wherein

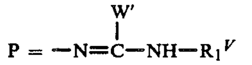

and $W'=OR_{12}$, may be prepared by the sequence of reactions shown in Equation 12.

Equation 12

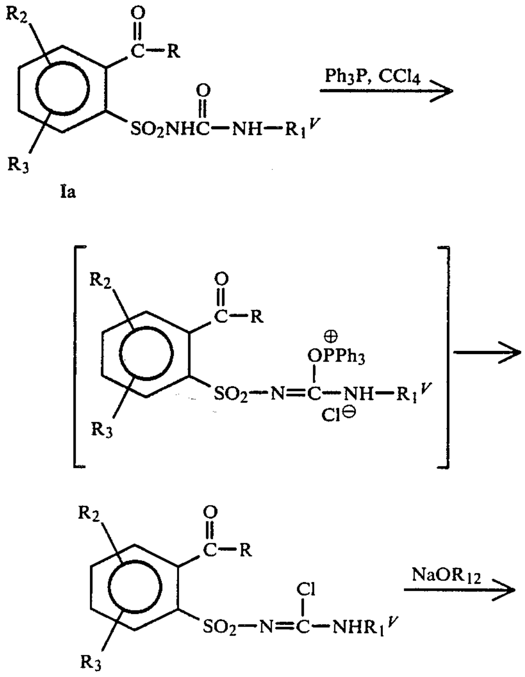

Ia

XVI

-continued

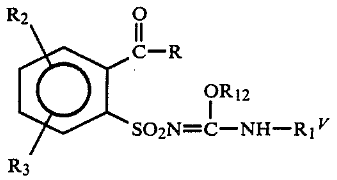

XVII

The compounds of Formula XVII are prepared by adding the appropriate carbon tetrahalide to a solution of one of the compounds of Formula Ia and triphenyl phosphine in an inert aprotic solvent such as acetonitrile at about −10° to 25°. The reaction is completed by stirring at the designated temperature for 10 to 48 hours. The carbamimidoyl halides of Formula XVI may be isolated by passing the reaction solution through a silica gel column to remove the triphenyl phosphine oxide and then removing the solvent by evaporation under reduced pressure.

The compounds of Formula XVI may also be converted directly to the compounds of Formula XVII by reacting the reaction mixture with a metal alkoxide at −10° to 25°. The reaction is completed by stirring at ambient temperature for 2 to 24 hours. The crude products of Formula XVII are isolated by filtering off the precipitated metal halide and removing the solvent by evaporation under reduced pressure. Further purification may be accomplished by recrystallization or by column chromatography over silica gel.

It will be understood by one skilled in the art that the compounds of Formula XVI are not necessarily converted directly to the compounds of Formula XVII, but may first form the carbodiimides of Formula XVIII.

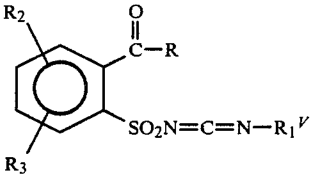

XVIII

As shown in Equation 13, the compounds of Formula I, wherein

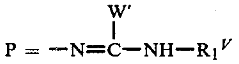

and $W'=SR_{11}$, can be prepared by reacting an appropriately substituted carbamimidothioic acid salt of Formula XXII with an alkylating agent of Formula XXIII.

Equation 13

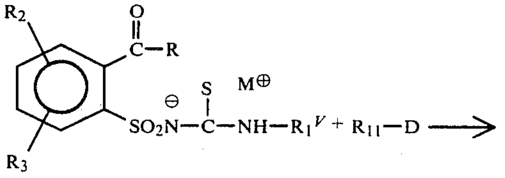

XXII XXIII

-continued

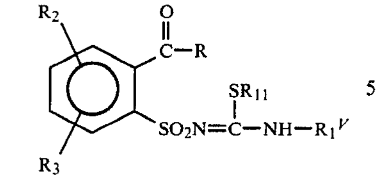

XXIV wherein D is a sulfate or halogen, such as Cl, Br or I; M is an alkali or alkaline earth metal.

The reaction is best carried out in inert aprotic organic solvents such as tetrahydrofuran or diethyl ether at temperatures between about 25° and 100° C. and at ambient pressure. The mode of addition is not critical; however, it is often convenient to add the alkylating agent in solution to a stirred suspension of said salt. The end product is isolated by evaporation of the solvent and recrystallization of the residue from a solvent such as acetonitrile or ethanol.

The metal salts of Formula XXII can be prepared by treating the corresponding sulfonylthiourea with a solution of an alkali metal or alkaline earth metal salt having an anion sufficiently basic to abstract the proton (e.g. hydroxide, alkoxide, carbonate or hydride).

The synthesis of heterocyclic amines has been reviewed in "The Chemistry of Heterocyclic Compounds" a series published by Interscience Publ., New York and London. 2-Aminopyrimidines are described by D. J. Brown in *The Pyrimidines,* Vol. XVI of this series. The 2-amino-1,3,5-triazines are reviewed by K. R. Huffman and in *The Triazines* of this same series. The synthesis of triazines are also described by F. C. Schaefer, U.S. Pat. No. 3,154,547 and by K. R. Huffman and F. C. Schaeffer, *J. Org. Chem.* 28, 1816-1821 (1963).

2-Aminopyridines are described in the volumes of this series entitled "Pyridine and Its Derivatives", 1962, edited by E. Klingsberg.

The preparation of the aminoheterocycles described by Formula XXIX varies according to the definition of $Y_1$ and $X_{II}$.

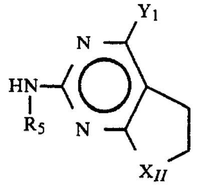

(XXIX)

Braker, Sheehan, Spitzmiller and Lott, *J. Am. Chem. Soc.* 69, 3072 (1947) describe the preparation of 6,7-dihydro-4-methoxy-5H-cyclopentapyrimidin-2-amine by the following sequence of reactions.

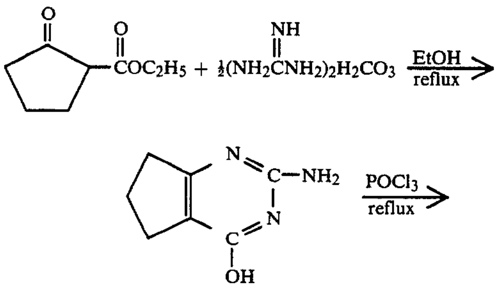

-continued

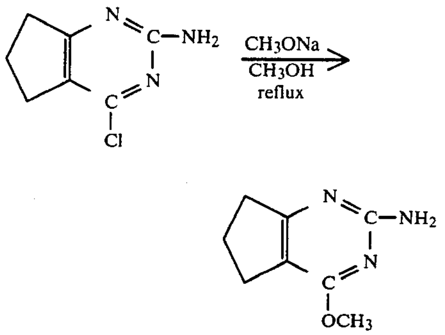

6,7-dihydro-4-methoxy-5H—cyclopentapyrimidin-2-amine.

Similarly, 6,7-dihydro-4-methyl-5H-cyclopentapyrimidin-2-amine can be prepared by the condensation of 2-acetylcyclopentanone with guanidine carbonate, but preferably under acidic conditions, removing the water formed.

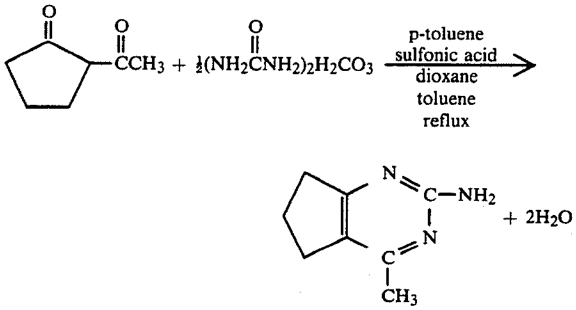

6,7-dihydro-4-methyl-5H—cyclopentapyrimidin-2-amine.

Shrage and Hitchings, *J. Org. Chem.* 16, 1153 (1951) describe the preparation of 5,6-dihydro-4-methylfuro[2,3-d]pyrimidin-2-amine by the following sequence of reactions

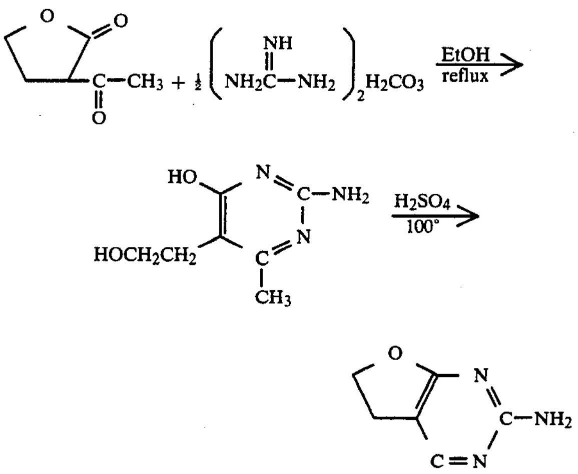

An analogous sequence of reactions can be used to prepare 6,7-dihydro-4-methyl-5H-pyrano[2,3-d]pyrimidin-2-amine starting with 2-acetyl-δ valerolactone [Korte and Wusten, *Tetrahedron* 19, 1423 (1963)].

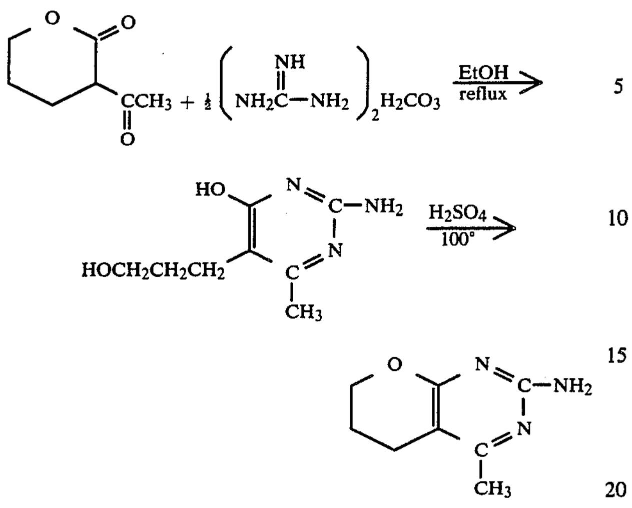

5,6-Dihydro-4-methoxyfuro[2,3-d]pyrimidin-2-amine can be prepared by the method of Braker et al., *J. Am. Chem. Soc.* 69, 3072 (1947), using 5,6-dihydro-4-hydroxyfuro[2,3-d]pyrimidin-2-amine (Svab, Budesinski and Vavrina, *Collection Czech. Chem. Commun.* 32, 1582 (1967)].

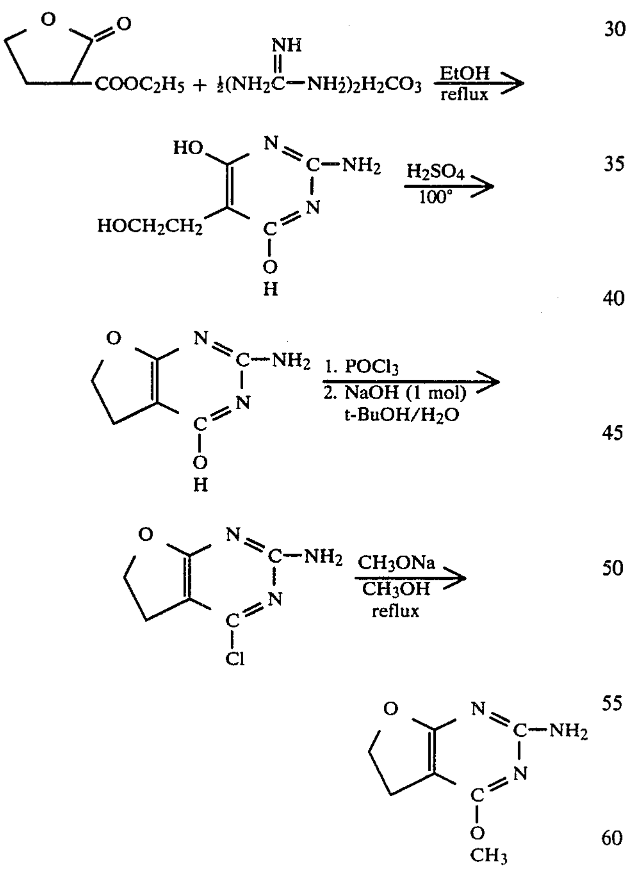

6,7-Dihydro-4-hydroxy-5H-pyrano[2,3-d]pyrimidin-2-amine can be prepared from diethyl 3-chloropropylmalonate, guanidine carbonate and sodium ethoxide in ethanol. Treatment of the product $ClCH_2CH_2CH_2CH(CO_2C_2H_5)_2$ +

-continued

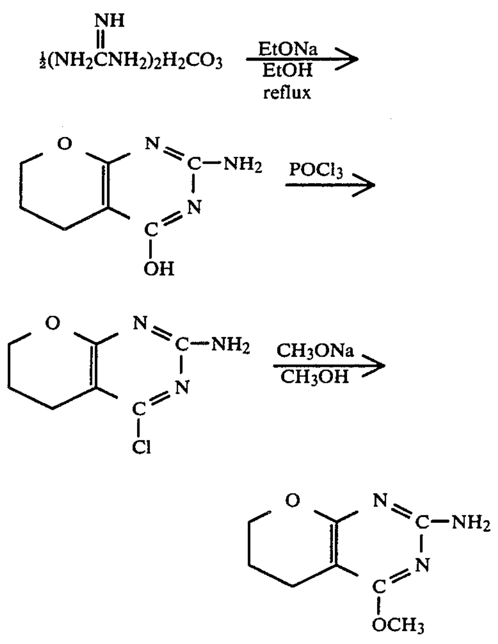

with phosphorus oxychloride gives 4-chloro-6,7-dihydro-5H-pyrano[2,3-d]pyrimidin-2-amine and subsequent reaction with sodium methoxide in refluxing methanol affords 6,7-dihydro-4-methoxy-5H-pyrano[2,3-d]pyrimidin-2-amine.

Caldwell, Kornfeld and Donnell, *J. Am. Chem. Soc.* 63, 2188 (1941), describe the preparation of 6,7-dihydro-5H-cyclopentapyrimidin-2-amine by the following sequence of reactions.

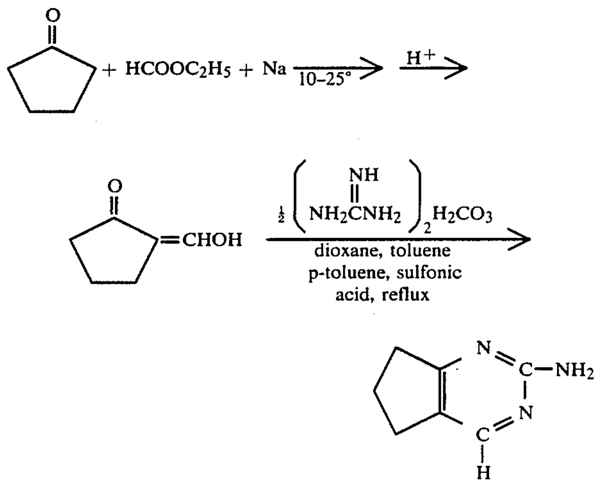

Fissekis, Myles and Brown, *J. Org. Chem.* 29, 2670 (1964), describe the preparation of 2-amino-4-hydroxy-5-(2-hydroxyethyl)pyrimidine which can be converted to 5,6-dihydrofuro[2,3-d]pyrimidin-2-amine by dehydration.

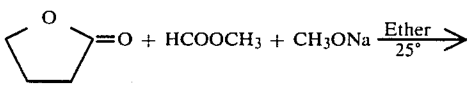

-continued

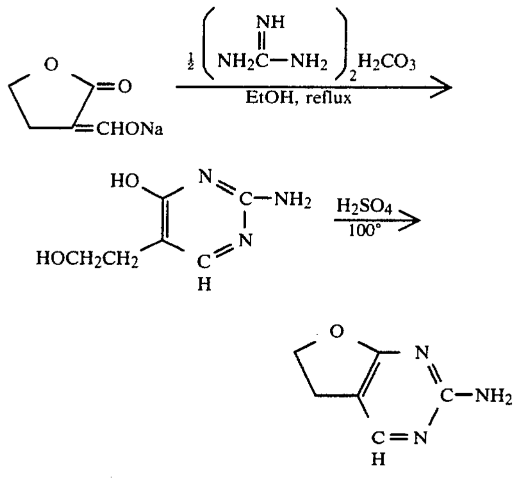

2-Amino-4-hydroxy-5-pyrimidinepropanol can be prepared in two steps by reaction of δ-valerolactone with ethyl formate and sodium hydride followed by treatment of the resulting sodium salt with guanidine carbonate in ethanol. Dehydration with sulfuric acid and subsequent liberation of the free amine with sodium hydroxide affords 6,7-dihydro-5H-pyrano[2,3-d]pyrimidin-2-amine.

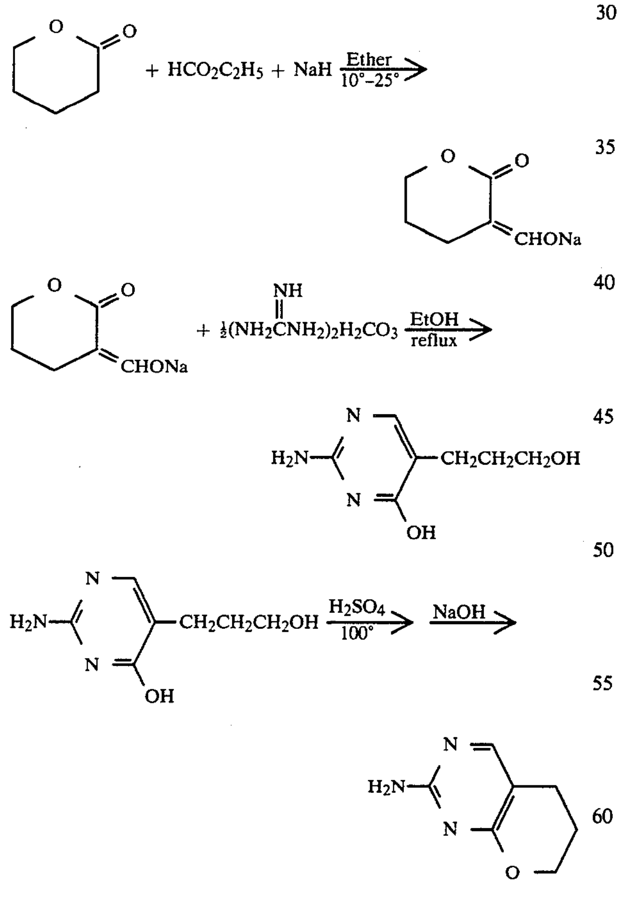

Agriculturally suitable salts of compounds of Formula I are also useful herbicides and can be prepared by a number of ways known to the art. For example, metal salts can be made by treating compounds of Formula I with a solution of alkali or alkaline earth metal salt having a sufficiently basic anion (e.g., hydroxide, alkoxide, carbonate or hydride). Quaternary amine salts can be made by similar techniques.

Salts of compounds of Formula I can also be prepared by exchange of one cation to another. Cationic exchange can be effected by direct treatment of an aqueous solution of a salt of a compound of Formula I (e.g., alkali metal or quaternary amine salt) with a solution containing the cation to be exchanged. This method is most effective when the desired salt containing the exchanged cation is insoluble in water, e.g., a copper salt, and can be separated by filtration.

Exchange may also be effected by passing an aqueous solution of a salt of a compound of Formula I (e.g., an alkali metal or quaternary amine salt) through a column packed with a cation exchange resin containing the cation to be exchanged. In this method, the cation of the resin is exchanged for that of the original salt and the desired product is eluted from the column. This method is particularly useful when the desired salt is water soluble, e.g., a potassium, sodium or calcium salt.

Acid addition salts, useful in this invention, can be obtained by reacting a compound of Formula I with a suitable acid, e.g., p-toluenesulfonic acid, trichloroacetic acid or the like.

The compounds of this invention and their preparation are further illustrated by the following examples wherein temperatures are given in degrees centigrade and all parts are by weight unless otherwise indicated.

EXAMPLE 1

Methyl 2-(isocyanatosulfonyl)benzoate

A stirred mixture containing 157 g of methyl 2-sulfamoylbenzoate, 73 g of butyl isocyanate, 0.3 g of 1,4-diazabicyclo[2,2,2]octane and 1.0 l of xylene was heated to reflux for one half hour. Phosgene gas was then passed into the system under a dry ice reflux condenser allowing the reaction temperature to drop to 120°. This addition was continued until the reflux temperature remained at 120° without further phosgene addition. The temperature of the reaction mixture was then raised to 136° (by removal of the dry ice reflux condenser) after which it was cooled to room temperature and filtered. Evaporation of the filtrate yielded the desired crude sulfonyl isocyanate which could be purified by distillation at 132°-138° C. under 1.0 to 1.1 mm of mercury pressure. The product is extremely reactive with water so contact with moisture should be scrupulously avoided.

EXAMPLE 2

N-[(4,6-Dimethoxypyrimidin-2-yl)aminocarbonyl]-2-methoxycarbonylbenzenesulfonamide A mixture containing 1.6 g of 2-amino-4,6-dimethoxypyrimidine, 30 ml of anhydrous methylene chloride and 2.4 g of 2-methoxycarbonylbenzenesulfonylisocyanate was stirred at ambient temperature and pressure for 16 hours. It was then filtered to remove unreacted amine and the filtrate evaporated at temperatures up to 40° and reduced pressure. The residue thus obtained was stirred in 25 ml of water, the pH adjusted to 10 by the addition of 50% aqueous sodium hydroxide and the solution filtered. Acidification of the filtrate to pH 3 caused the formation of a precipitate. Filtration and drying the precipitate yielded 1.7 g of the desired product, melting at 185°-190°. Its infrared absorption peaks at 1700 and 1710 $cm^{-1}$ are consistent for the desired structure and the nuclear magnetic resonance absorption peaks at 3.8 and 3.85 are consistent for the two different types of methoxy groups brought together in this product.

EXAMPLE 3

N-[(4,6-Dimethoxypyrimidin-2-yl)aminocarbonyl]-2-carboxybenzenesulfonamide

A mixture containing 5 g of N-[(4,6-dimethoxypyrimidin-2-yl)aminocarbonyl]-2-methoxycarbonylbenzenesulfonamide, 20 ml of ethanol, 2.5 ml of water and 2.5 g of potassium hydroxide was stirred at ambient temperature and pressure for 18 hours. The mixture was then diluted with 250 ml of water and 20 ml of concentrated hydrochloric acid was added with stirring. The precipitate was filtered and washed with water and dried to yield 4.85 g of the desired product, melting at 161°-2° C. The infrared absorption peaks at 3500, 3400 and 1700 $cm^{-1}$ are consistent with the desired structure and the nuclear magnetic resonance absorption peaks at 3.95 ppm, s, 6H, $OCH_3$ of pyrimidine; 5.8 ppm, s, 1H, pyrimidine proton at position 5; and 7.6–8.3 ppm, m, 4H, aromatic protons, are consistent with the desired structure.

EXAMPLE 4

2-Acetyl-N-[(4,6-dimethoxypyrimidin-2-yl)aminocarbonyl]benzenesulfonamide

A mixture containing 0.85 g of N-[(4,6-dimethoxypyrimidin-2-yl)aminocarbonyl]-2-carboxybenzenesulfonamide in 50 ml of anhydrous tetrahydrofuran was treated with 40 ml of a 1.4 molar solution of methyl lithium (low halide, Aldrich) in ether at 25° under a nitrogen atmosphere. The mixture was stirred for 4 hours at 25° and was then poured into 500 ml of water containing 10 ml of concentrated hydrochloric acid. The precipitated oil was extracted into methylene chloride and the oil on evaporation of solvent was purified by preparative thin layer chromatography on silica gel (Analtec, 2000 micron, 20×20 plates) by elution with ethyl acetate/hexane in a one to one ratio. The isolated product was recrystallized from a 1-chlorobutane and hexane mixture to give 0.1 g, m.p. 126°-8°. The infrared absorption showed a broadened carbonyl peak at 1710 $cm^{-1}$, and the absence of the 3500 and 3400 $cm^{-1}$ peaks of the starting material. The nuclear magnetic resonance spectrum showed peaks at 2.6 ppm, s, 3H, $$CH_3\overset{\overset{O}{\|}}{C}Ar;$$

4.0 ppm, s, 6H, $CH_3O$ of pyrimidine; 5.7 ppm, s, 1H, pyrimidine proton at position 5; and 7.3–7.7 ppm and 8.0 ppm, m, 4H, aromatic, which are consistent with the desired structure.

EXAMPLE 5

2-[(4-Methoxy-6-methyl-1,3,5-triazin-2-yl)aminocarbonyl]aminosulfonylbenzoic acid A solution of 0.5 g of potassium tert-butoxide and 1.0 g of methyl 2-[(4-methoxy-6-methyl-1,3,5-triazin-2-yl)aminocarbonyl]aminosulfonylbenzoate in 25 ml of dimethyl sulfoxide was stirred at ambient temperature for 3 hours. The yellow solution was then poured into 250 ml of cold water. The free carboxylic acid was precipitated by the addition of enough concentrated hydrochloric acid to reach pH 3. The crude product was filtered, washed with water and dried in vacuo. Recrystallization from acetonitrile yielded 0.5 g of the title compound, m.p. 157°-158° C. The mass spectrum of this compound exhibited the expected molecular ion at m/e=367. The infrared bands at 3300 $cm^{-1}$ and 1725 $cm^{-1}$ are consistent with the desired structure. The nuclear magnetic resonance spectrum showed peaks at 2.5 ppm (triazine $CH_3$), 3.9 ppm (triazine $OCH_3$) and 7.4–8.2 ppm (phenyl). The methyl ester peak present in the starting material was not observed in the spectrum of the product.

EXAMPLE 6

2-Formyl-N-[4,6-dimethoxypyrimidin-2-yl)aminocarbonyl]benzenesulfonamide

To a mixture of 3.0 g (10 mmol) of a 70 percent solution of sodium bis-(2-methoxyethoxy)aluminum hydride, 25 ml of tetrahydrofuran, and 0.9 g (10 mmol) of morpholine, cooled to −40° C., was added 1.0 g (3 mmol) of N-[(4,6-dimethoxypyrimidin-2-yl)aminocarbonyl]-2-carboxybenzenesulfonamide. The solution was allowed to warm to ambient temperature over a 2-hour period and 100 ml of 2M hydrochloric acid was then added. The product was extracted with methylene chloride and the extracts were dried over magnesium sulfate. Purification of the crude product by chromatography on silica gel provided the title compound, m.p. 180° C. The infrared spectrum exhibited carbonyl bands at 1710 $cm^{-1}$ and 1700 $cm^{-1}$, indicative of the urea and aldehyde carbonyls present in this molecule. The nuclear magnetic resonance peaks at 3.95 ppm ($OCH_3$), 5.95 ppm (pyrimidine H), 7.6–8.4 ppm (phenyl) and 10.7 ppm (CHO) are consistent with the assigned structure.

EXAMPLE 7

2-Formyl-N-[(4,6-dimethylpyrimidin-2-yl)aminocarbonyl]benzenesulfonamide

To a solution of 6.26 mmol of sodium ethoxide in 10 ml of absolute ethanol under an argon atmosphere was added 0.80 ml of 2-nitropropane. Next 0.74 g (2.09 mmol) of 2-chloromethyl-N-[(4,6-dimethylpyrimidin-2-yl)aminocarbonyl]benzenesulfonamide was added and the solution was heated to reflux. The mixture became pasty shortly after heating was begun and an additional 3 ml of ethanol was added to facilitate stirring. After heating for 4 hours, the solvent was removed under reduced pressure and the residue was dissolved in 12 ml of water. The crude product was precipitated by neutralization of the solution with 3N hydrochloric acid. The crude product was purified by preparative thin layer chromatography on silica gel and subsequent recrystallization from acetone to provide the title compound, m.p. 157° C. (decomp.). The infrared spectrum showed a new carbonyl band at 1675 $cm^{-1}$, indicative of the formation of an aldehyde, in addition to the urea carbonyl band at 1710 $cm^{-1}$. The nuclear magnetic resonance spectrum showed peaks at 10.57 ppm and 10.67 ppm which are consistent with an aromatic aldehyde with restricted rotation.

Anal. Calcd. for $C_{14}H_{14}N_4O_4S$: C, 50.29%; H, 4.22%; N, 16.76. Found: C, 49.94%: H, 4.32%; N, 16.57%.

Using the procedures of Examples 1 to 7 and the proper reactants or the methods described herein, the compounds in Tables I–XI may be prepared.

TABLE I

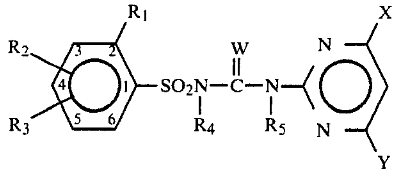

| $R_1$ | $R_2$ | $R_3$ | $R_4$ | $R_5$ | W | X | Y | melting point °C. |
|---|---|---|---|---|---|---|---|---|
| $CH_3\overset{\overset{O}{\|}}{C}-$ | H | H | H | H | O | $CH_3O-$ | $CH_3O-$ | 126-128 |
| $CH_3\overset{\overset{O}{\|}}{C}-$ | H | H | H | H | O | $CH_3O-$ | $CH_3-$ | 136.5-140 |
| $CH_3\overset{\overset{O}{\|}}{C}-$ | H | H | H | H | O | $CH_3-$ | $CH_3-$ | 173-174 |
| $CH_3\overset{\overset{O}{\|}}{C}-$ | H | H | H | H | S | $CH_3O-$ | $CH_3O-$ | |
| $CH_3\overset{\overset{O}{\|}}{C}-$ | H | H | H | $CH_3$ | O | $CH_3O-$ | $CH_3-$ | |
| $CH_3\overset{\overset{O}{\|}}{C}-$ | H | H | H | $CH_3O$ | O | $CH_3O-$ | $CH_3-$ | |
| $CH_3\overset{\overset{O}{\|}}{C}-$ | H | H | $CH_3$ | $CH_3$ | O | $CH_3O-$ | $CH_3-$ | |
| $CH_3\overset{\overset{O}{\|}}{C}-$ | 3-Cl | H | $CH_3$ | $CH_3$ | O | $CH_3O-$ | $CH_3-$ | |
| $CH_3\overset{\overset{O}{\|}}{C}-$ | 4-Cl | H | $CH_3$ | $CH_3$ | O | $CH_3O-$ | $CH_3-$ | |
| $CH_3\overset{\overset{O}{\|}}{C}-$ | 5-Cl | H | $CH_3$ | $CH_3$ | O | $CH_3O-$ | $CH_3-$ | |
| $CH_3\overset{\overset{O}{\|}}{C}-$ | 6-Cl | H | $CH_3$ | $CH_3$ | O | $CH_3O-$ | $CH_3-$ | |
| $CH_3\overset{\overset{O}{\|}}{C}-$ | 4-Cl | 5-Cl | $CH_3$ | $CH_3$ | O | $CH_3O-$ | $CH_3-$ | |
| $CH_3\overset{\overset{O}{\|}}{C}-$ | 5-Cl | 6-$CH_3$ | $CH_3$ | $CH_3$ | O | $CH_3O-$ | $CH_3-$ | |
| $CH_3\overset{\overset{O}{\|}}{C}-$ | 5-F | H | $CH_3$ | $CH_3$ | O | $CH_3O-$ | $CH_3-$ | |
| $CH_3\overset{\overset{O}{\|}}{C}-$ | 5-Br | H | $CH_3$ | $CH_3$ | O | $CH_3O-$ | $CH_3-$ | |
| $CH_3\overset{\overset{O}{\|}}{C}-$ | 5-$CH_3$ | H | $CH_3$ | $CH_3$ | O | $CH_3O-$ | $CH_3-$ | |
| $CH_3\overset{\overset{O}{\|}}{C}-$ | 5-i-$C_3H_7$ | H | $CH_3$ | $CH_3$ | O | $CH_3O-$ | $CH_3-$ | |
| $CH_3\overset{\overset{O}{\|}}{C}-$ | 5-$NO_2$ | H | $CH_3$ | $CH_3$ | O | $CH_3O-$ | $CH_3-$ | |

TABLE I-continued

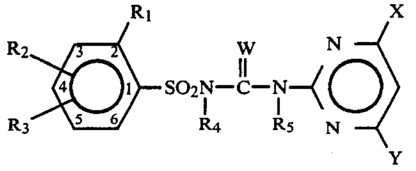

| $R_1$ | $R_2$ | $R_3$ | $R_4$ | $R_5$ | W | X | Y | melting point °C. |
|---|---|---|---|---|---|---|---|---|
| $CH_3\overset{O}{\overset{\|}{C}}-$ | 5-$CH_3\underset{\underset{O}{\|}}{\overset{\overset{O}{\|}}{S}}-$ | H | $CH_3$ | $CH_3$ | O | $CH_3O-$ | $CH_3-$ | |
| $CH_3\overset{O}{\overset{\|}{C}}-$ | 5-$CH_3O-$ | H | $CH_3$ | $CH_3$ | O | $CH_3O-$ | $CH_3-$ | |
| $CH_3\overset{O}{\overset{\|}{C}}-$ | 5-$CH_3S-$ | H | $CH_3$ | $CH_3$ | O | $CH_3O-$ | $CH_3-$ | |
| $CH_3\overset{O}{\overset{\|}{C}}-$ | 5-$CF_3-$ | H | $CH_3$ | $CH_3$ | O | $CH_3O-$ | $CH_3-$ | |
| $CH_3\overset{O}{\overset{\|}{C}}-$ | 5-$(CH_3)_2N-$ | H | $CH_3$ | $CH_3$ | O | $CH_3O-$ | $CH_3-$ | |
| $CH_3\overset{O}{\overset{\|}{C}}-$ | 6-$NO_2-$ | H | $CH_3$ | $CH_3$ | O | $CH_3O-$ | $CH_3-$ | |
| $CH_3\overset{O}{\overset{\|}{C}}-$ | 6-$CF_3$ | H | $CH_3$ | $CH_3$ | O | $CH_3O-$ | $CH_3-$ | |
| $CH_3\overset{O}{\overset{\|}{C}}-$ | 6-$CH_3\underset{\underset{O}{\|}}{\overset{\overset{O}{\|}}{S}}-$ | H | $CH_3$ | $CH_3$ | O | $CH_3O-$ | $CH_3-$ | |
| $CH_3\overset{O}{\overset{\|}{C}}-$ | H | H | H | H | O | H | H | |
| $CH_3\overset{O}{\overset{\|}{C}}-$ | H | H | H | H | O | Cl | Cl | |
| $CH_3\overset{O}{\overset{\|}{C}}-$ | H | H | H | H | O | $CH_3CH_2O-$ | $CH_3-$ | |
| $CH_3\overset{O}{\overset{\|}{C}}-$ | H | H | H | H | O | $CH_3OCH_2CH_2O-$ | $CH_3-$ | |
| $CH_3\overset{O}{\overset{\|}{C}}-$ | H | H | H | H | O | $CH_3$ | Cl | |
| $CH_3\overset{O}{\overset{\|}{C}}-$ | H | H | H | H | O | $CH_3$ | n-$C_4H_9-$ | |
| $CH_3\overset{O}{\overset{\|}{C}}-$ | H | H | H | H | O | $CH_3$ | $CH_3OCH_2-$ | |
| $CH_3\overset{O}{\overset{\|}{C}}-$ | H | H | H | H | O | $CH_3$ | $CH_3O(CH_2)_4-$ | |
| $CH_3\overset{O}{\overset{\|}{C}}-$ | H | H | H | H | O | $CH_3$ | $NCCH_2-$ | |

TABLE I-continued

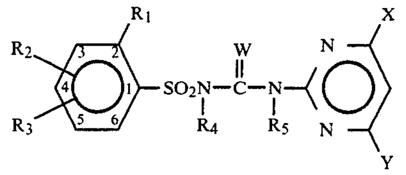

| $R_1$ | $R_2$ | $R_3$ | $R_4$ | $R_5$ | W | X | Y | melting point °C. |
|---|---|---|---|---|---|---|---|---|
| O<br>‖<br>$CH_3C$— | H | H | H | H | O | $CH_3$ | $CH_3O_2CCH_2$— | |
| O<br>‖<br>$CH_3C$— | H | H | H | H | O | $CH_3$ | $C_2H_5O_2CCH_2$— | |
| O<br>‖<br>$CH_3C$— | H | H | H | H | O | $CH_3$ | $CF_3$— | |
| O<br>‖<br>$CH_3C$— | H | H | H | H | O | $CH_3$ | $ClCH_2CH_2$— | |
| O<br>‖<br>$CH_3C$— | H | H | H | H | O | $CH_3$ | $BrCH_2CH_2$— | |
| O<br>‖<br>$CH_3C$— | H | H | H | H | O | $CH_3$ | $CH_2{=}CHCH_2$— | |
| O<br>‖<br>$CH_3C$— | H | H | H | H | O | $CH_3$ | $CH_3C{\equiv}CCH_2$— | |
| O<br>‖<br>$CH_3C$— | H | H | H | H | O | $CH_3$ | $ClCH_2C{\equiv}CCH_2$— | |
| O<br>‖<br>$CH_3C$— | H | H | H | H | O | $CH_3$ | O<br>‖<br>$CH_3SCH_2CH_2O$—<br>‖<br>O | |
| O<br>‖<br>$CH_3C$— | H | H | H | H | O | $CH_3$— | $CH_3S(CH_2)_3O$— | |
| O<br>‖<br>$CH_3C$— | H | H | H | H | O | $CH_3$— | $CH_3O_2CCH_2O$— | |
| O<br>‖<br>$CH_3C$— | H | H | H | H | O | $CH_3$— | $CH_3O_2CCH_2S$— | |
| O<br>‖<br>$CH_3C$— | H | H | H | H | O | $CH_3$— | $CH_3O_2CCHO$—<br>\|<br>$CH_3$ | |
| O<br>‖<br>$CH_3C$— | H | H | H | H | O | $CH_3$— | n-$C_6H_{13}O_2CCHO$—<br>\|<br>$CH_3$ | |
| O<br>‖<br>$CH_3C$— | H | H | H | H | O | $CH_3$— | $HO_2CCHO$—<br>\|<br>$CH_3$ | |
| O<br>‖<br>$CH_3C$— | H | H | H | H | O | $CH_3$— | O<br>‖<br>$H_2NCCH_2O$ | |
| O<br>‖<br>$CH_3C$— | H | H | H | H | O | $CH_3$— | O<br>‖<br>$CH_3N$—$CCH_2O$—<br>\|<br>$OCH_3$ | |

TABLE I-continued

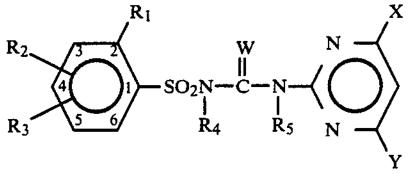

| $R_1$ | $R_2$ | $R_3$ | $R_4$ | $R_5$ | W | X | Y | melting point °C. |
|---|---|---|---|---|---|---|---|---|
| $CH_3\overset{O}{\overset{\|}{C}}-$ | H | H | H | H | O | $CH_3-$ | $n\text{-}C_4H_9NH\overset{O}{\overset{\|}{C}}CH_2O$ | |
| $CH_3\overset{O}{\overset{\|}{C}}-$ | H | H | H | H | O | $CH_3-$ | $(CH_3)_2N\overset{O}{\overset{\|}{C}}CH_2O-$ | |
| $CH_3\overset{O}{\overset{\|}{C}}-$ | H | H | H | H | O | $CH_3-$ | $NCS-$ | |
| $CH_3\overset{O}{\overset{\|}{C}}-$ | H | H | H | H | O | $CH_3-$ | $N_3-$ | |
| $CH_3\overset{O}{\overset{\|}{C}}-$ | H | H | H | H | O | $CH_3-$ | $H_2N-$ | |
| $CH_3\overset{O}{\overset{\|}{C}}-$ | H | H | H | H | O | $CH_3-$ | $(CH_3)_2N-$ | |
| $CH_3\overset{O}{\overset{\|}{C}}-$ | H | H | H | H | O | $CH_3-$ | $n\text{-}C_4H_9HN-$ | |
| $CH_3\overset{O}{\overset{\|}{C}}-$ | H | H | H | H | O | $CH_3-$ | $CH_3-\underset{OCH_3}{\underset{\|}{N}}-$ | |
| $CH_3\overset{O}{\overset{\|}{C}}-$ | H | H | H | H | O | $CH_3-$ | $CH_5-\underset{CH_2CN}{\underset{\|}{N}}-$ | |
| $CH_3\overset{O}{\overset{\|}{C}}-$ | H | H | H | H | O | $CH_3-$ | 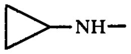 | |
| $CH_3\overset{O}{\overset{\|}{C}}-$ | H | H | H | H | O | $CH_3-$ | 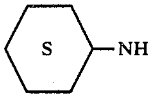 | |
| $CH_3\overset{O}{\overset{\|}{C}}-$ | H | H | H | H | O | $CH_3-$ | $CH_3O_2CCH_2\underset{CH_3}{\underset{\|}{N}}-$ | |
| $CH_3\overset{O}{\overset{\|}{C}}-$ | H | H | H | H | O | $CH_3-$ | $CH_2{=}CHCH_2NH-$ | |
| $CH_3\overset{O}{\overset{\|}{C}}-$ | H | H | H | H | O | $CH_3-$ | $CH_3O(CH_2)_2\underset{CH_3}{\underset{\|}{N}}-$ | |
| $CH_3\overset{O}{\overset{\|}{C}}-$ | H | H | H | H | O | $CH_3-$ | 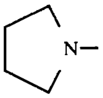 | |
| $CH_3\overset{O}{\overset{\|}{C}}-$ | H | H | H | H | O | $CH_3-$ | 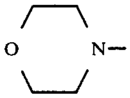 | |

TABLE I-continued

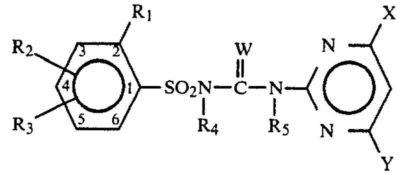

| $R_1$ | $R_2$ | $R_3$ | $R_4$ | $R_5$ | W | X | Y | melting point °C. |
|---|---|---|---|---|---|---|---|---|
| $CH_3\overset{O}{\overset{\|}{C}}-$ | H | H | H | H | O | $CH_3-$ | $n\text{-}C_4H_9O-$ | |
| $CH_3\overset{O}{\overset{\|}{C}}-$ | H | H | H | H | O | $CH_3-$ | $CF_3CH_2O-$ | |
| $CH_3\overset{O}{\overset{\|}{C}}-$ | H | H | H | H | O | $CH_3-$ | $ClCH_2CH_2O-$ | |
| $CH_3\overset{O}{\overset{\|}{C}}-$ | H | H | H | H | O | $CH_3-$ | $BrCH_2CH_2O-$ | |
| $CH_3\overset{O}{\overset{\|}{C}}-$ | H | H | H | H | O | $CH_3-$ | $NCCH_2CH_2O-$ | |
| $CH_3\overset{O}{\overset{\|}{C}}-$ | H | H | H | H | O | $CH_3-$ | $CH_2{=}CHCH_2O-$ | |
| $CH_3\overset{O}{\overset{\|}{C}}-$ | H | H | H | H | O | $CH_3-$ | $CH_3C{\equiv}CCH_2O-$ | |
| $CH_3\overset{O}{\overset{\|}{C}}-$ | H | H | H | H | O | $CH_3-$ | $ClCH_2C{\equiv}CCH_2O-$ | |
| $CH_3\overset{O}{\overset{\|}{C}}-$ | H | H | H | H | O | $CH_3-$ | 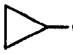 $-CH_2O-$ | |
| $CH_3\overset{O}{\overset{\|}{C}}-$ | H | H | H | H | O | $CH_3-$ | 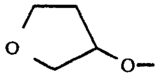 | |
| $CH_3\overset{O}{\overset{\|}{C}}-$ | H | H | H | H | O | $CH_3-$ | $CH_3S-$ | |
| $CH_3\overset{O}{\overset{\|}{C}}-$ | H | H | H | H | O | $CH_3-$ | $n\text{-}C_4H_9S-$ | |
| $CH_3\overset{O}{\overset{\|}{C}}-$ | H | H | H | H | O | $CH_3-$ | $NCCH_2CH_2S-$ | |
| $CH_3\overset{O}{\overset{\|}{C}}-$ | H | H | H | H | O | $CH_3-$ | $CH_2{=}CHCH_2S-$ | |
| $CH_3\overset{O}{\overset{\|}{C}}-$ | H | H | H | H | O | $CH_3-$ | $HC{\equiv}CCH_2S-$ | |
| $CH_3CH_2-\overset{O}{\overset{\|}{C}}-$ | H | H | H | H | O | $CH_3-$ | $CH_3O-$ | |
| $(CH_3)_2CH-\overset{O}{\overset{\|}{C}}-$ | H | H | H | H | O | $CH_3-$ | $CH_3O-$ | |
| $n\text{-}C_{12}H_{25}\overset{O}{\overset{\|}{C}}-$ | H | H | H | H | O | $CH_3-$ | $CH_3O-$ | |

TABLE I-continued

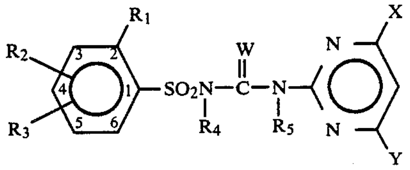

| $R_1$ | $R_2$ | $R_3$ | $R_4$ | $R_5$ | W | X | Y | melting point °C. |
|---|---|---|---|---|---|---|---|---|
| $CH_2{=}CH{-}\overset{O}{\overset{\|}{C}}{-}$ | H | H | H | H | O | $CH_3-$ | $CH_3O-$ | |
| $CH_2{=}CHCH_2\overset{O}{\overset{\|}{C}}{-}$ | H | H | H | H | O | $CH_3-$ | $CH_3O-$ | |
| $CH_3(CH_2)_2CH{=}CHCH_2\overset{O}{\overset{\|}{C}}{-}$ | H | H | H | H | O | $CH_3-$ | $CH_3O-$ | |
| $CH_3C{\equiv}CCH_2\overset{O}{\overset{\|}{C}}{-}$ | H | H | H | H | O | $CH_3-$ | $CH_3O-$ | |
| $ClCH_2\overset{O}{\overset{\|}{C}}{-}$ | H | H | H | H | O | $CH_3-$ | $CH_3O-$ | |
| $BrCH_2CH_2\overset{O}{\overset{\|}{C}}{-}$ | H | H | H | H | O | $CH_3-$ | $CH_3O-$ | |
| $CF_3\overset{O}{\overset{\|}{C}}{-}$ | H | H | H | H | O | $CH_3-$ | $CH_3O-$ | |
| $CH_3OCH_2\overset{O}{\overset{\|}{C}}{-}$ | H | H | H | H | O | $CH_3-$ | $CH_3O-$ | |
| $NCCH_2\overset{O}{\overset{\|}{C}}{-}$ | H | H | H | H | O | $CH_3-$ | $CH_3O-$ | |
| $CH_3O\overset{O}{\overset{\|}{C}}{-}\overset{O}{\overset{\|}{C}}{-}$ | H | H | H | H | O | $CH_3-$ | $CH_3O-$ | |
| $C_2H_5O{-}\overset{O}{\overset{\|}{C}}{-}CH_2\overset{O}{\overset{\|}{C}}{-}$ | H | H | H | H | O | $CH_3-$ | $CH_3O-$ | |
| $i\text{-}C_3H_7O\overset{O}{\overset{\|}{C}}CH_2CH_2\overset{O}{\overset{\|}{C}}{-}$ | H | H | H | H | O | $CH_3-$ | $CH_3O-$ | |
| $ClCH_2CH{=}CHCH_2\overset{O}{\overset{\|}{C}}$ | H | H | H | H | O | $CH_3-$ | $CH_3O-$ | |
| 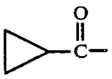 | H | H | H | H | O | $CH_3-$ | $CH_3O-$ | |
| 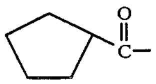 | H | H | H | H | O | $CH_3-$ | $CH_3O-$ | |
| 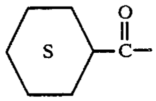 | H | H | H | H | O | $CH_3-$ | $CH_3O-$ | |

TABLE I-continued
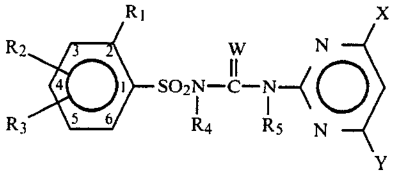
| $R_1$ | $R_2$ | $R_3$ | $R_4$ | $R_5$ | W | X | Y | melting point °C. |
|---|---|---|---|---|---|---|---|---|
| 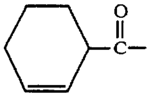 | H | H | H | H | O | $CH_3-$ | $CH_3O-$ | |
| 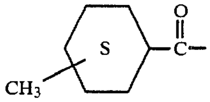 | H | H | H | H | O | $CH_3-$ | $CH_3O-$ | |
| 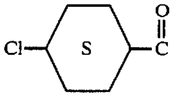 | H | H | H | H | O | $CH_3-$ | $CH_3O-$ | |
| 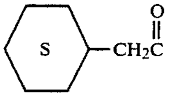 | H | H | H | H | O | $CH_3-$ | $CH_3O-$ | |
| 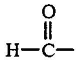 | H | H | H | H | O | $CH_3-$ | $CH_3O-$ | |
| 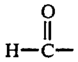 | H | H | H | H | O | $CH_3O-$ | $CH_3O-$ | 180 |
| 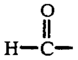 | H | H | H | H | O | $CH_3-$ | $CH_3-$ | 157 (decom.) |
| 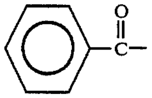 | H | H | H | H | O | $CH_3-$ | $CH_3O-$ | |
| 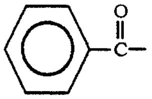 | H | H | H | H | O | $CH_3O-$ | $CH_3O-$ | |
| 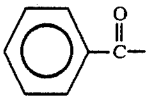 | H | H | H | H | O | $CH_3-$ | $CH_3-$ | |
| 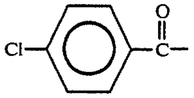 | H | H | H | H | O | $CH_3-$ | $CH_3O-$ | |
| 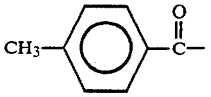 | H | H | H | H | O | $CH_3-$ | $CH_3O-$ | |
| 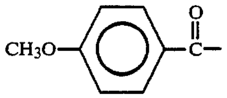 | H | H | H | H | O | $CH_3-$ | $CH_3O-$ | |

TABLE I-continued

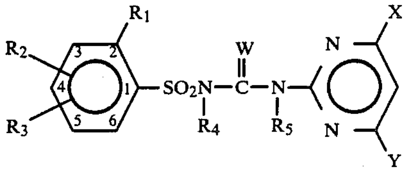

| $R_1$ | $R_2$ | $R_3$ | $R_4$ | $R_5$ | W | X | Y | melting point °C. |
|---|---|---|---|---|---|---|---|---|
| 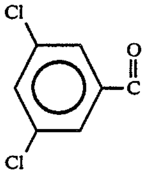 | H | H | H | H | O | $CH_3$— | $CH_3O$— | |
| 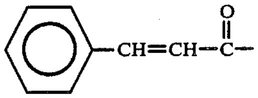 | H | H | H | H | O | $CH_3$— | $CH_3O$— | |
| 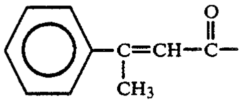 | H | H | H | H | O | $CH_3$— | $CH_3O$— | |
| 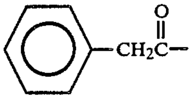 | H | H | H | H | O | $CH_3$— | $CH_3O$— | |
| 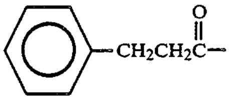 | H | H | H | H | O | $CH_3$— | $CH_3O$— | |
| 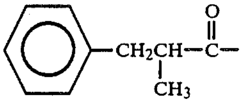 | H | H | H | H | O | $CH_3$— | $CH_3O$— | |
| $NOCH_3$<br>‖<br>$CH_3C$— | H | H | H | H | O | $CH_3$— | $CH_3O$— | |
| $NOCH_3$<br>‖<br>$CH_3C$— | H | H | H | H | O | $CH_3O$— | $CH_3O$— | |
| $NOCH_3$<br>‖<br>$CH_3C$— | H | H | H | H | O | $CH_3$— | $CH_3$— | |
| NO—n-$C_4H_9$<br>‖<br>$CH_3C$— | H | H | H | H | O | $CH_3$— | $CH_3O$— | |
| $NOCH_2CH{=}CH_2$<br>‖<br>$CH_3C$— | H | H | H | H | O | $CH_3$— | $CH_3O$— | |
| $NOCH_3$<br>‖<br>H—C— | H | H | H | H | O | $CH_3$— | $CH_3O$— | |
| O $NOCH_3$<br>‖ ‖<br>$CH_3OCCH_2C$— | H | H | H | H | O | $CH_3$— | $CH_3O$— | |
| $NOCH_3$<br>‖<br>$(CH_3)_2CHC$— | H | H | H | H | O | $CH_3$— | $CH_3O$— | |

TABLE I-continued
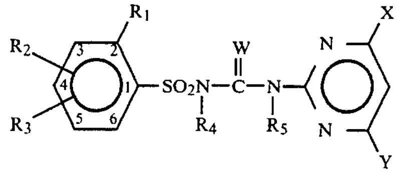
| $R_1$ | $R_2$ | $R_3$ | $R_4$ | $R_5$ | W | X | Y | melting point °C. |
|---|---|---|---|---|---|---|---|---|
| 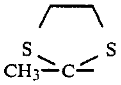 | H | H | H | H | O | $CH_3$— | $CH_3O$— | |
| 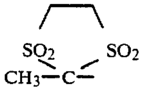 | H | H | H | H | O | $CH_3$— | $CH_3O$— | |
| 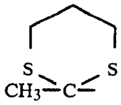 | H | H | H | H | O | $CH_3$— | $CH_3O$— | |
| 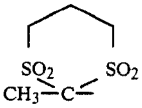 | H | H | H | H | O | $CH_3$— | $CH_3O$— | |
| 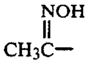 | H | H | H | H | O | $CH_3$— | $CH_3O$— | |
| 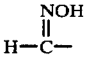 | H | H | H | H | O | $CH_3$— | $CH_3O$— | |
| 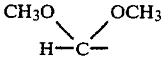 | H | H | H | H | O | $CH_3$— | $CH_3O$— | |
| 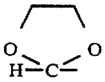 | H | H | H | H | O | $CH_3$— | $CH_3O$— | |
| 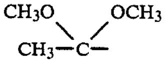 | H | H | H | H | O | $CH_3$— | $CH_3O$— | |
| 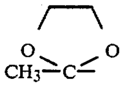 | H | H | H | H | O | $CH_3$— | $CH_3O$— | |
| 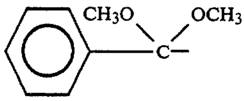 | H | H | H | H | O | $CH_3$— | $CH_3O$— | |
| 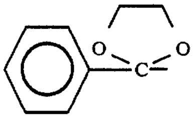 | H | H | H | H | O | $CH_3$— | $CH_3O$— | |
| 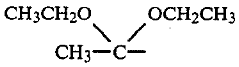 | H | H | H | H | O | $CH_3$— | $CH_3O$— | |

TABLE I-continued

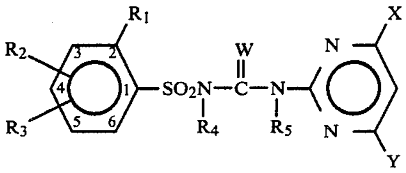

| $R_1$ | $R_2$ | $R_3$ | $R_4$ | $R_5$ | W | X | Y | melting point °C. |
|---|---|---|---|---|---|---|---|---|
| 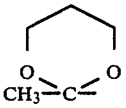 | H | H | H | H | O | $CH_3-$ | $CH_3O-$ | |

TABLE II

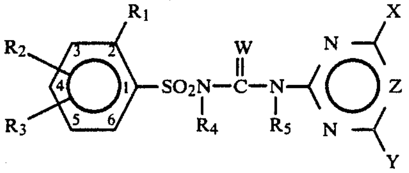

| $R_1$ | $R_2$ | $R_3$ | $R_4$ | $R_5$ | W | Z | X | Y |
|---|---|---|---|---|---|---|---|---|
| $CH_3\overset{\overset{O}{\|}}{C}-$ | H | H | H | H | O | C—F | $CH_3-$ | $CH_3-$ |
| $CH_3\overset{\overset{O}{\|}}{C}-$ | H | H | H | H | O | C—Cl | $CH_3-$ | $CH_3-$ |
| $CH_3\overset{\overset{O}{\|}}{C}-$ | H | H | H | H | O | C—Br | $CH_3-$ | $CH_3-$ |
| $CH_3\overset{\overset{O}{\|}}{C}-$ | H | H | H | H | O | $C-CH_3$ | $CH_3-$ | $CH_3-$ |
| $CH_3\overset{\overset{O}{\|}}{C}-$ | H | H | H | H | O | $C-C_2H_5$ | $CH_3-$ | $CH_3-$ |
| $CH_3\overset{\overset{O}{\|}}{C}-$ | H | H | H | H | O | $C-CH_2CH_2Cl$ | $CH_3-$ | $CH_3-$ |
| $CH_3\overset{\overset{O}{\|}}{C}-$ | H | H | H | H | O | $C-CH_3$ | H | H |
| $CH_3\overset{\overset{O}{\|}}{C}-$ | H | H | H | H | O | $C-CH_3$ | H | $CH_3-$ |
| $CH_3\overset{\overset{O}{\|}}{C}-$ | H | H | H | H | O | $C-CH_3$ | H | $CH_3O-$ |
| $CH_3\overset{\overset{O}{\|}}{C}-$ | H | H | H | H | O | $C-CH_3$ | $CH_3-$ | $CH_3O-$ |
| $CH_3\overset{\overset{O}{\|}}{C}-$ | H | H | H | H | O | $C-CH_3$ | $CH_3O-$ | $CH_3O-$ |
| $CH_3\overset{\overset{O}{\|}}{C}-$ | H | H | H | H | O | $C-CH_3$ | Cl | H |
| $CH_3\overset{\overset{O}{\|}}{C}-$ | H | H | H | H | O | $C-CH_3$ | Cl | $CH_3-$ |

TABLE II-continued
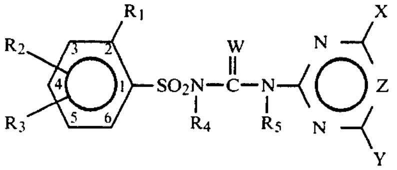
| $R_1$ | $R_2$ | $R_3$ | $R_4$ | $R_5$ | W | Z | X | Y |
|---|---|---|---|---|---|---|---|---|
| 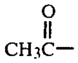 | H | H | H | H | O | C—$CH_3$ | Cl | $CH_3O$— |
| 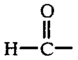 | H | H | H | H | O | C—$CH_3$ | $CH_3$— | $CH_3$— |
| 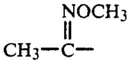 | H | H | H | H | O | C—$CH_3$ | $CH_3$— | $CH_3$— |
| 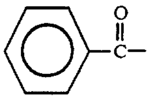 | H | H | H | H | O | C—$CH_3$ | $CH_3$— | $CH_3$— |
| 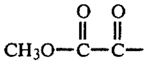 | H | H | H | H | O | C—$CH_3$ | $CH_3$— | $CH_3$— |
| 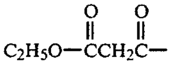 | H | H | H | H | O | C—$CH_3$ | $CH_3$— | $CH_3$— |
| 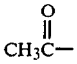 | H | H | H | H | S | C—$CH_3$ | $CH_3$— | $CH_3$— |
| 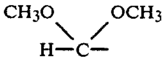 | H | H | H | H | O | C—$CH_3$ | $CH_3$— | $CH_3$— |
| 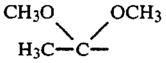 | H | H | H | H | O | C—$CH_3$ | $CH_3$— | $CH_3$— |
| 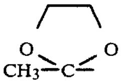 | H | H | H | H | O | C—$CH_3$ | $CH_3$— | $CH_3$— |
| 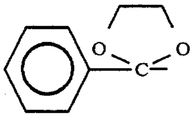 | H | H | H | H | O | C—$CH_3$ | $CH_3$— | $CH_3$— |
TABLE III
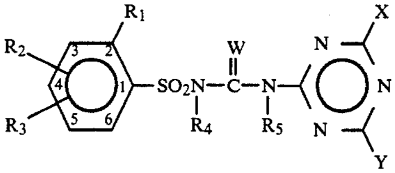
| $R_1$ | $R_2$ | $R_3$ | $R_4$ | $R_5$ | W | X | Y |
|---|---|---|---|---|---|---|---|
| 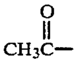 | H | H | H | H | O | $CH_3O$— | $CH_3O$— |
| 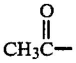 | H | H | H | H | O | $CH_3O$— | $CH_3$— |

TABLE III-continued

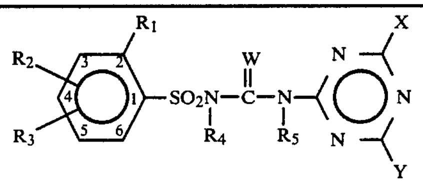

| $R_1$ | $R_2$ | $R_3$ | $R_4$ | $R_5$ | W | X | Y |
|---|---|---|---|---|---|---|---|
| O<br>‖<br>$CH_3C$— | H | H | H | H | O | $CH_3$— | $CH_3$— |
| O<br>‖<br>$CH_3C$— | H | H | H | H | S | $CH_3O$— | $CH_3O$— |
| O<br>‖<br>$CH_3C$— | H | H | H | $CH_3$ | O | $CH_3O$— | $CH_3$— |
| O<br>‖<br>$CH_3C$— | H | H | H | $CH_3O$ | O | $CH_3O$— | $CH_3$— |
| O<br>‖<br>$CH_3C$— | H | H | $CH_3$ | $CH_3$ | O | $CH_3O$— | $CH_3$— |
| O<br>‖<br>$CH_3C$— | 3-Cl | H | $CH_3$ | $CH_3$ | O | $CH_3O$— | $CH_3$— |
| O<br>‖<br>$CH_3C$— | 4-Cl | H | $CH_3$ | $CH_3$ | O | $CH_3O$— | $CH_3$— |
| O<br>‖<br>$CH_3C$— | 5-Cl | H | $CH_3$ | $CH_3$ | O | $CH_3O$— | $CH_3$— |
| O<br>‖<br>$CH_3C$— | 6-Cl | H | $CH_3$ | $CH_3$ | 0 | $CH_3O$— | $CH_3$— |
| O<br>‖<br>$CH_3C$— | 4-Cl | 5-Cl | $CH_3$ | $CH_3$ | O | $CH_3O$— | $CH_3$— |
| O<br>‖<br>$CH_3C$— | 5-Cl | 6-$CH_3$ | $CH_3$ | $CH_3$ | O | $CH_3O$— | $CH_3$— |
| O<br>‖<br>$CH_3C$— | 5-F | H | $CH_3$ | $CH_3$ | O | $CH_3O$— | $CH_3$— |
| O<br>‖<br>$CH_3C$— | 5-Br | H | $CH_3$ | $CH_3$ | O | $CH_3O$— | $CH_3$— |
| O<br>‖<br>$CH_3C$— | 5-$CH_3$ | H | $CH_3$ | $CH_3$ | O | $CH_3O$— | $CH_3$— |
| O<br>‖<br>$CH_3C$— | 5-i-$C_3H_7$ | H | $CH_3$ | $CH_3$ | O | $CH_3O$— | $CH_3$— |
| O<br>‖<br>$CH_3C$— | 5-$NO_2$ | H | $CH_3$ | $CH_3$ | O | $CH_3O$— | $CH_3$— |
| O<br>‖<br>$CH_3C$— | O<br>‖<br>5-$CH_3S$—<br>‖<br>O | H | $CH_3$ | $CH_3$ | O | $CH_3O$— | $CH_3$— |
| O<br>‖<br>$CH_3C$— | 5-$CH_3O$— | H | $CH_3$ | $CH_3$ | O | $CH_3O$— | $CH_3$— |

TABLE III-continued

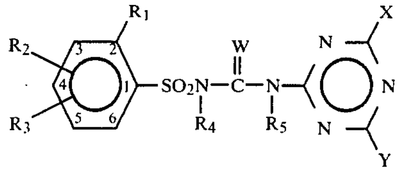

| $R_1$ | $R_2$ | $R_3$ | $R_4$ | $R_5$ | W | X | Y |
|---|---|---|---|---|---|---|---|
| $CH_3\overset{\overset{O}{\|}}{C}-$ | 5-$CH_3S-$ | H | $CH_3$ | $CH_3$ | O | $CH_3O-$ | $CH_3-$ |
| $CH_3\overset{\overset{O}{\|}}{C}-$ | 5-$CF_3-$ | H | $CH_3$ | $CH_3$ | O | $CH_3O-$ | $CH_3-$ |
| $CH_3\overset{\overset{O}{\|}}{C}-$ | 5-$(CH_3)_2N-$ | H | $CH_3$ | $CH_3$ | O | $CH_3O-$ | $CH_3-$ |
| $CH_3\overset{\overset{O}{\|}}{C}-$ | 6-$NO_2-$ | H | $CH_3$ | $CH_3$ | O | $CH_3O-$ | $CH_3-$ |
| $CH_3\overset{\overset{O}{\|}}{C}-$ | 6-$CF_3$ | H | $CH_3$ | $CH_3$ | O | $CH_3O-$ | $CH_3-$ |
| $CH_3\overset{\overset{O}{\|}}{C}-$ | 6-$CH_3\overset{\overset{O}{\|}}{\underset{\underset{O}{\|}}{S}}-$ | H | $CH_3$ | $CH_3$ | O | $CH_3O-$ | $CH_3-$ |
| $CH_3\overset{\overset{O}{\|}}{C}-$ | H | H | H | H O | H | H | |
| $CH_3\overset{\overset{O}{\|}}{C}-$ | H | H | H | H | O | Cl | Cl |
| $CH_3\overset{\overset{O}{\|}}{C}-$ | H | H | H | H | O | $CH_3CH_2O-$ | $CH_3-$ |
| $CH_3\overset{\overset{O}{\|}}{C}-$ | H | H | H | H | O | $CH_3OCH_2CH_2O-$ | $CH_3-$ |
| $CH_3\overset{\overset{O}{\|}}{C}-$ | H | H | H | H | O | $CH_3$ | Cl |
| $CH_3\overset{\overset{O}{\|}}{C}-$ | H | H | H | H | O | $CH_3$ | n-$C_4H_9-$ |
| $CH_3\overset{\overset{O}{\|}}{C}-$ | H | H | H | H | O | $CH_3$ | $CH_3OCH_2-$ |
| $CH_3\overset{\overset{O}{\|}}{C}-$ | H | H | H | H | O | $CH_3$ | $CH_3O(CH_2)_4-$ |
| $CH_3\overset{\overset{O}{\|}}{C}-$ | H | H | H | H | O | $CH_3$ | $NCCH_2-$ |
| $CH_3\overset{\overset{O}{\|}}{C}-$ | H | H | H | H | O | $CH_3$ | $CH_3O_2C\overline{C}H_2-$ |
| $CH_3\overset{\overset{O}{\|}}{C}-$ | H | H | H | H | O | $CH_3$ | $C_2H_5O_2CCH_2-$ |
| $CH_3\overset{\overset{O}{\|}}{C}-$ | H | H | H | H | O | $CH_3$ | $CF_3-$ |

TABLE III-continued

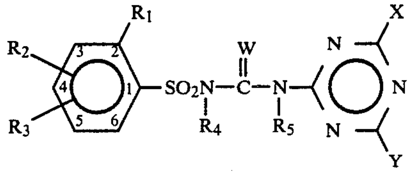

| $R_1$ | $R_2$ | $R_3$ | $R_4$ | $R_5$ | W | X | Y |
|---|---|---|---|---|---|---|---|
| $CH_3\overset{\overset{O}{\|}}{C}-$ | H | H | H | H | O | $CH_3$ | $ClCH_2CH_2-$ |
| $CH_3\overset{\overset{O}{\|}}{C}-$ | H | H | H | H | O | $CH_3$ | $BrCH_2CH_2-$ |
| $CH_3\overset{\overset{O}{\|}}{C}-$ | H | H | H | H | O | $CH_3$ | $CH_2{=}CHCH_2-$ |
| $CH_3\overset{\overset{O}{\|}}{C}-$ | H | H | H | H | O | $CH_3$ | $CH_3C{\equiv}CCH_2-$ |
| $CH_3\overset{\overset{O}{\|}}{C}-$ | H | H | H | H | O | $CH_3$ | $ClCH_2C{\equiv}CCH_2-$ |
| $CH_3\overset{\overset{O}{\|}}{C}-$ | H | H | H | H | O | $CH_3$ | $CH_3\underset{\underset{O}{\|}}{\overset{\overset{O}{\|}}{S}}CH_2CH_2O-$ |
| $CH_3\overset{\overset{O}{\|}}{C}-$ | H | H | H | H | O | $CH_3-$ | $CH_3S(CH_2)_3O-$ |
| $CH_3\overset{\overset{O}{\|}}{C}-$ | H | H | H | H | O | $CH_3-$ | $CH_3O_2CCH_2O-$ |
| $CH_3\overset{\overset{O}{\|}}{C}-$ | H | H | H | H | O | $CH_3-$ | $CH_3O_2CCH_2S-$ |
| $CH_3\overset{\overset{O}{\|}}{C}-$ | H | H | H | H | O | $CH_3-$ | $CH_3O_2C\underset{\underset{CH_3}{\mid}}{C}HO-$ |
| $CH_3\overset{\overset{O}{\|}}{C}-$ | H | H | H | H | O | $CH_3-$ | $n\text{-}C_6H_{13}O_2C\underset{\underset{CH_3}{\mid}}{C}HO-$ |
| $CH_3\overset{\overset{O}{\|}}{C}-$ | H | H | H | H | O | $CH_3-$ | $HO_2C\underset{\underset{CH_3}{\mid}}{C}HO-$ |
| $CH_3\overset{\overset{O}{\|}}{C}-$ | H | H | H | H | O | $CH_3-$ | $H_2N\overset{\overset{O}{\|}}{C}CH_2O$ |
| $CH_3\overset{\overset{O}{\|}}{C}-$ | H | H | H | H | O | $CH_3-$ | $CH_3\underset{\underset{OCH_3}{\mid}}{N}-\overset{\overset{O}{\|}}{C}CH_2O-$ |
| $CH_3\overset{\overset{O}{\|}}{C}-$ | H | H | H | H | O | $CH_3-$ | $n\text{-}C_4H_9NH\overset{\overset{O}{\|}}{C}CH_2O$ |
| $CH_3\overset{\overset{O}{\|}}{C}-$ | H | H | H | H | O | $CH_3-$ | $(CH_3)_2N\overset{\overset{O}{\|}}{C}CH_2O-$ |
| $CH_3\overset{\overset{O}{\|}}{C}-$ | H | H | H | H | O | $CH_3-$ | $NCS-$ |

TABLE III-continued

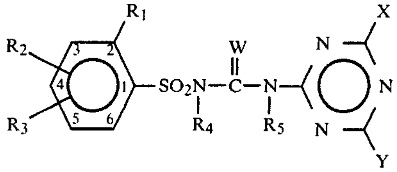

| $R_1$ | $R_2$ | $R_3$ | $R_4$ | $R_5$ | W | X | Y |
|---|---|---|---|---|---|---|---|
| $CH_3\overset{O}{\overset{\|}{C}}-$ | H | H | H | H | O | $CH_3-$ | $N_3-$ |
| $CH_3\overset{O}{\overset{\|}{C}}-$ | H | H | H | H | O | $CH_3-$ | $H_2N-$ |
| $CH_3\overset{O}{\overset{\|}{C}}-$ | H | H | H | H | O | $CH_3-$ | $(CH_3)_2N-$ |
| $CH_3\overset{O}{\overset{\|}{C}}-$ | H | H | H | H | O | $CH_3-$ | $n\text{-}C_4H_9HN-$ |
| $CH_3\overset{O}{\overset{\|}{C}}-$ | H | H | H | H | O | $CH_3-$ | $CH_3-\underset{OCH_3}{\underset{\|}{N}}-$ |
| $CH_3\overset{O}{\overset{\|}{C}}-$ | H | H | H | H | O | $CH_3-$ | $CH_5-\underset{CH_2CN}{\underset{\|}{N}}-$ |
| $CH_3\overset{O}{\overset{\|}{C}}-$ | H | H | H | H | O | $CH_3-$ | 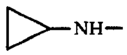 |
| $CH_3\overset{O}{\overset{\|}{C}}-$ | H | H | H | H | O | $CH_3-$ | 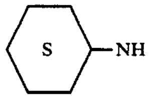 |
| $CH_3\overset{O}{\overset{\|}{C}}-$ | H | H | H | H | O | $CH_3-$ | $CH_3O_2CCH_2\underset{CH_3}{\underset{\|}{N}}-$ |
| $CH_3\overset{O}{\overset{\|}{C}}-$ | H | H | H | H | O | $CH_3-$ | $CH_2{=}CHCH_2NH-$ |
| $CH_3\overset{O}{\overset{\|}{C}}-$ | H | H | H | H | O | $CH_3-$ | $CH_3O(CH_2)_2\underset{CH_3}{\underset{\|}{N}}-$ |
| $CH_3\overset{O}{\overset{\|}{C}}-$ | H | H | H | H | O | $CH_3-$ | 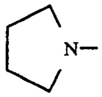 |
| $CH_3\overset{O}{\overset{\|}{C}}-$ | H | H | H | H | O | $CH_3-$ | 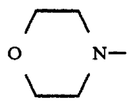 |
| $CH_3\overset{O}{\overset{\|}{C}}-$ | H | H | H | H | O | $CH_3-$ | $n\text{-}C_4H_9O-$ |
| $CH_3\overset{O}{\overset{\|}{C}}-$ | H | H | H | H | O | $CH_3-$ | $CF_3CH_2O-$ |
| $CH_3\overset{O}{\overset{\|}{C}}-$ | H | H | H | H | O | $CH_3-$ | $ClCH_2CH_2O-$ |

TABLE III-continued

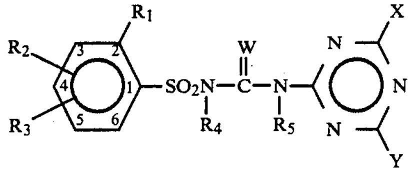

| $R_1$ | $R_2$ | $R_3$ | $R_4$ | $R_5$ | W | X | Y |
|---|---|---|---|---|---|---|---|
| O<br>‖<br>$CH_3C$— | H | H | H | H | O | $CH_3$— | $BrCH_2CH_2O$— |
| O<br>‖<br>$CH_3C$— | H | H | H | H | O | $CH_3$— | $NCCH_2CH_2O$— |
| O<br>‖<br>$CH_3C$— | H | H | H | H | O | $CH_3$— | $CH_2$=$CHCH_2O$— |
| O<br>‖<br>$CH_3C$— | H | H | H | H | O | $CH_3$— | $CH_3C$≡$CCH_2O$— |
| O<br>‖<br>$CH_3C$— | H | H | H | H | O | $CH_3$— | $ClCH_2C$≡$CCH_2O$— |
| O<br>‖<br>$CH_3C$— | H | H | H | H | O | $CH_3$— | 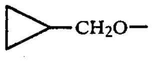 |
| O<br>‖<br>$CH_3C$— | H | H | H | H | O | $CH_3$— | 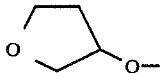 |
| O<br>‖<br>$CH_3C$— | H | H | H | H | O | $CH_3$— | $CH_3S$— |
| O<br>‖<br>$CH_3C$— | H | H | H | H | O | $CH_3$— | n-$C_4H_9S$— |
| O<br>‖<br>$CH_3C$— | H | H | H | H | O | $CH_3$— | $NCCH_2CH_2S$— |
| O<br>‖<br>$CH_3C$— | H | H | H | H | O | $CH_3$— | $CH_2$=$CHCH_2S$— |
| O<br>‖<br>$CH_3C$— | H | H | H | H | O | $CH_3$— | HC≡$CCH_2S$— |
| 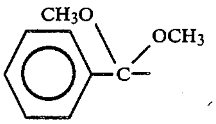 | H | H | H | H | O | $CH_3$— | $CH_3O$— |
| 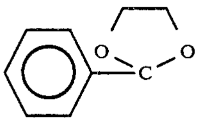 | H | H | H | H | O | $CH_3$— | $CH_3O$— |
| O<br>‖<br>$CH_3CH_2$—C— | H | H | H | H | O | $CH_3$— | $CH_3O$— |
| O<br>‖<br>$(CH_3)_2CH$—C— | H | H | H | H | O | $CH_3$— | $CH_3O$— |

TABLE III-continued
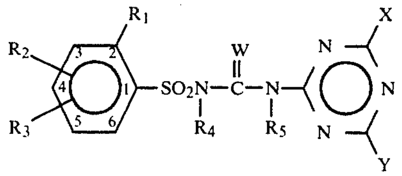
| $R_1$ | $R_2$ | $R_3$ | $R_4$ | $R_5$ | W | X | Y |
|---|---|---|---|---|---|---|---|
| 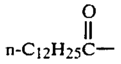 | H | H | H | H | O | $CH_3$— | $CH_3O$— |
| 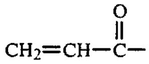 | H | H | H | H | O | $CH_3$— | $CH_3O$— |
| 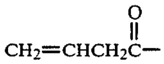 | H | H | H | H | O | $CH_3$— | $CH_3O$— |
| 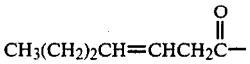 | H | H | H | H | O | $CH_3$— | $CH_3O$— |
| 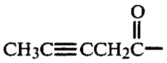 | H | H | H | H | O | $CH_3$— | $CH_3O$— |
| 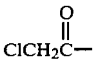 | H | H | H | H | O | $CH_3$— | $CH_3O$— |
| 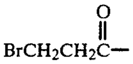 | H | H | H | H | O | $CH_3$— | $CH_3O$— |
| 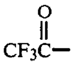 | H | H | H | H | O | $CH_3$— | $CH_3O$— |
| 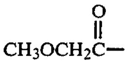 | H | H | H | H | O | $CH_3$— | $CH_3O$— |
| 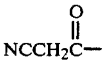 | H | H | H | H | O | $CH_3$— | $CH_3O$— |
| 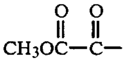 | H | H | H | H | O | $CH_3$— | $CH_3O$— |
| 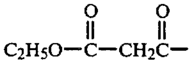 | H | H | H | H | O | $CH_3$— | $CH_3O$— |
| 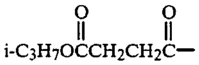 | H | H | H | H | O | $CH_3$— | $CH_3O$— |
| 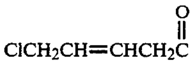 | H | H | H | H | O | $CH_3$— | $CH_3O$— |
| 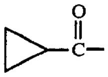 | H | H | H | H | O | $CH_3$— | $CH_3O$— |
| 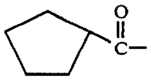 | H | H | H | H | O | $CH_3$— | $CH_3O$— |
| 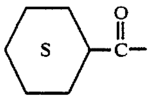 | H | H | H | H | O | $CH_3$— | $CH_3O$— |

TABLE III-continued
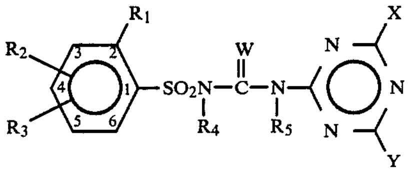
| $R_1$ | $R_2$ | $R_3$ | $R_4$ | $R_5$ | W | X | Y |
|---|---|---|---|---|---|---|---|
| 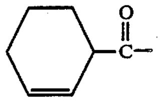 | H | H | H | H | O | $CH_3$— | $CH_3O$— |
| 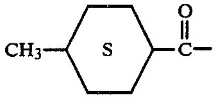 | H | H | H | H | O | $CH_3$— | $CH_3O$— |
| 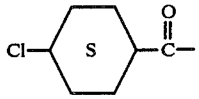 | H | H | H | H | O | $CH_3$— | $CH_3O$— |
| 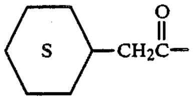 | H | H | H | H | O | $CH_3$— | $CH_3O$— |
| 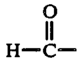 | H | H | H | H | O | $CH_3$— | $CH_3O$— |
| 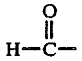 | H | H | H | H | O | $CH_3O$— | $CH_3O$— |
| 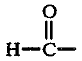 | H | H | H | H | O | $CH_3$— | $CH_3$— |
| 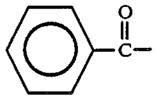 | H | H | H | H | O | $CH_3$— | $CH_3O$— |
| 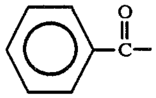 | H | H | H | H | O | $CH_3O$— | $CH_3O$— |
| 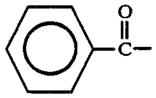 | H | H | H | H | O | $CH_3$— | $CH_3$— |
| 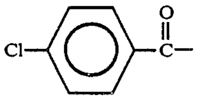 | H | H | H | H | O | $CH_3$— | $CH_3O$— |
| 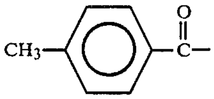 | H | H | H | H | O | $CH_3$— | $CH_3O$— |
| 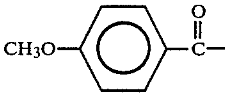 | H | H | H | H | O | $CH_3$— | $CH_3O$— |

TABLE III-continued
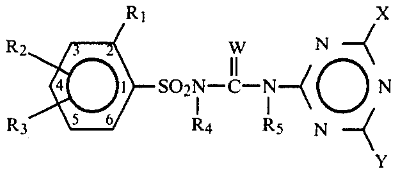
| R₁ | R₂ | R₃ | R₄ | R₅ | W | X | Y |
|---|---|---|---|---|---|---|---|
| 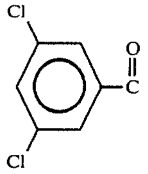 | H | H | H | H | O | $CH_3$— | $CH_3O$— |
| 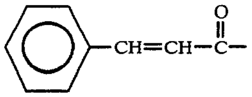 | H | H | H | H | O | $CH_3$— | $CH_3O$— |
| 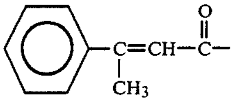 | H | H | H | H | O | $CH_3$— | $CH_3O$— |
| 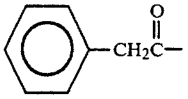 | H | H | H | H | O | $CH_3$— | $CH_3O$— |
| 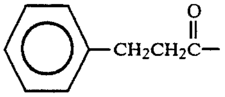 | H | H | H | H | O | $CH_3$— | $CH_3O$— |
| 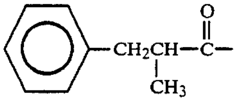 | H | H | H | H | O | $CH_3$— | $CH_3O$— |
| 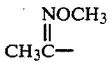 | H | H | H | H | O | $CH_3$— | $CH_3O$— |
| 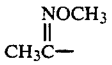 | H | H | H | H | O | $CH_3O$— | $CH_3O$— |
| 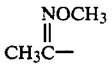 | H | H | H | H | O | $CH_3$— | $CH_3$— |
| 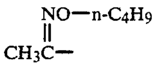 | H | H | H | H | O | $CH_3$— | $CH_3O$— |
| 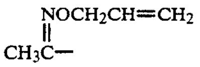 | H | H | H | H | O | $CH_3$— | $CH_3O$— |
| 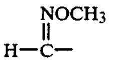 | H | H | H | H | O | $CH_3$— | $CH_3O$— |
| 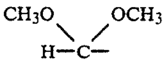 | H | H | H | H | O | $CH_3$— | $CH_3O$— |
| 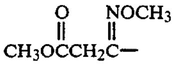 | H | H | H | H | O | $CH_3$— | $CH_3O$— |

TABLE III-continued

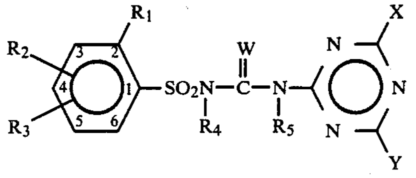

| $R_1$ | $R_2$ | $R_3$ | $R_4$ | $R_5$ | W | X | Y |
|---|---|---|---|---|---|---|---|
| NOCH<sub></sub>$_3$<br>‖<br>$(CH_3)_2CH_3$— | H | H | H | H | O | $CH_3$— | $CH_3O$— |
| 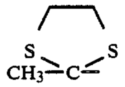 | H | H | H | H | O | $CH_3$— | $CH_3O$— |
| 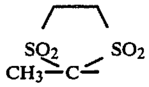 | H | H | H | H | O | $CH_3$— | $CH_3O$— |
| 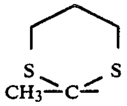 | H | H | H | H | O | $CH_3$— | $CH_3O$— |
| 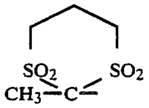 | H | H | H | H | O | $CH_3$— | $CH_3O$— |
| NOH<br>‖<br>$CH_3C$— | H | H | H | H | O | $CH_3$— | $CH_3O$— |
| NOH<br>‖<br>H—C— | H | H | H | H | O | $CH_3$— | $CH_3O$— |
| 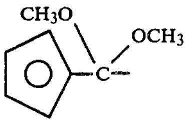 | H | H | H | H | O | $CH_3$— | $CH_3O$— |
| 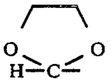 | H | H | H | H | O | $CH_3$— | $CH_3O$— |
| 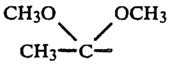 | H | H | H | H | O | $CH_3$— | $CH_3O$— |

TABLE IV

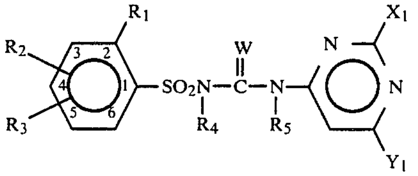

| $R_1$ | $R_2$ | $R_3$ | $R_4$ | $R_5$ | W | $X_1$ | $Y_1$ |
|---|---|---|---|---|---|---|---|
| O<br>‖<br>$CH_3C$— | H | H | H | H | O | $CH_3O$— | $CH_3O$— |
| O<br>‖<br>$CH_3C$— | H | H | H | H | O | $CH_3O$— | $CH_3$— |

TABLE IV-continued

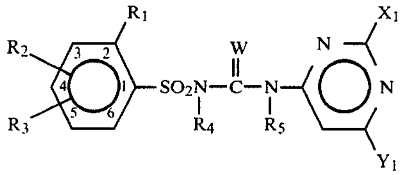

| $R_1$ | $R_2$ | $R_3$ | $R_4$ | $R_5$ | W | $X_1$ | $Y_1$ |
|---|---|---|---|---|---|---|---|
| O<br>‖<br>$CH_3C-$ | H | H | H | H | O | $CH_3-$ | $CH_3-$ |
| O<br>‖<br>$CH_3C-$ | H | H | H | H | S | $CH_3-$ | $CH_3-$ |
| O<br>‖<br>$CH_3C-$ | 3-Cl | H | H | H | O | $CH_3-$ | $CH_3-$ |
| O<br>‖<br>$CH_3C-$ | 4-Cl | H | H | H | O | $CH_3-$ | $CH_3-$ |
| O<br>‖<br>$CH_3C-$ | 5-Cl | H | H | H | O | $CH_3-$ | $CH_3-$ |
| O<br>‖<br>$CH_3C-$ | 6-Cl | H | H | H | O | $CH_3-$ | $CH_3-$ |
| O<br>‖<br>$CH_3C-$ | 4-Cl | 5-Cl | H | H | O | $CH_3-$ | $CH_3-$ |
| O<br>‖<br>$CH_3C-$ | 5-Cl | 6-$CH_3$ | H | H | O | $CH_3-$ | $CH_3-$ |
| O<br>‖<br>$CH_3C-$ | 5-F | H | H | H | O | $CH_3$ | $CH_3-$ |
| O<br>‖<br>$CH_3C-$ | 5-Br | H | H | H | O | $CH_3$ | $CH_3-$ |
| O<br>‖<br>$CH_3C-$ | 5-$CH_3$ | H | H | H | O | $CH_3$ | $CH_3-$ |
| O<br>‖<br>$CH_3C-$ | 5-i-$C_3H_7$ | H | H | H | O | $CH_3$ | $CH_3-$ |
| O<br>‖<br>$CH_3C-$ | 5-$NO_2$ | H | H | H | O | $CH_3$ | $CH_3-$ |
| O<br>‖<br>$CH_3C-$ | O<br>‖<br>5-$CH_3S-$<br>‖<br>O | H | H | H | O | $CH_3-$ | $CH_3-$ |
| O<br>‖<br>$CH_3C-$ | 5-$CH_3O-$ | H | H | H | O | $CH_3-$ | $CH_3-$ |
| O<br>‖<br>$CH_3C-$ | 5-$CH_3S-$ | H | H | H | O | $CH_3-$ | $CH_3-$ |
| O<br>‖<br>$CH_3C-$ | 5-$CF_3-$ | H | H | H | O | $CH_3-$ | $CH_3-$ |
| O<br>‖<br>$CH_3C-$ | 5-$(CH_3)_2N-$ | H | H | H | O | $CH_3-$ | $CH_3-$ |

TABLE IV-continued

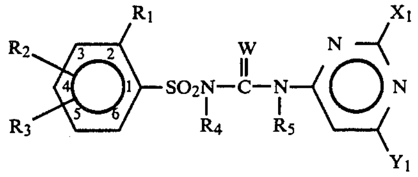

| $R_1$ | $R_2$ | $R_3$ | $R_4$ | $R_5$ | W | $X_1$ | $Y_1$ |
|---|---|---|---|---|---|---|---|
| $CH_3\overset{O}{\overset{\|}{C}}-$ | $6\text{-}NO_2-$ | H | H | H | O | $CH_3-$ | $CH_3-$ |
| $CH_3\overset{O}{\overset{\|}{C}}-$ | $6\text{-}CF_3$ | H | H | H | O | $CH_3-$ | $CH_3-$ |
| $CH_3\overset{O}{\overset{\|}{C}}-$ | $6\text{-}CH_3\underset{O}{\underset{\|}{\overset{O}{\overset{\|}{S}}}}-$ | H | H | H | S | $CH_3-$ | $CH_3-$ |
| $CH_3CH_2-\overset{O}{\overset{\|}{C}}-$ | H | H | H | H | O | $CH_3-$ | $CH_3-$ |
| $(CH_3)_2CH-\overset{O}{\overset{\|}{C}}-$ | H | H | H | H | O | $CH_3-$ | $CH_3-$ |
| $n\text{-}C_5H_{11}-\overset{O}{\overset{\|}{C}}-$ | H | H | H | H | O | $CH_3-$ | $CH_3-$ |
| $CH_2{=}CH-\overset{O}{\overset{\|}{C}}-$ | H | H | H | H | O | $CH_3-$ | $CH_3-$ |
| $CH_2{=}CHCH_2\overset{O}{\overset{\|}{C}}-$ | H | H | H | H | O | $CH_3-$ | $CH_3-$ |
| $CH_3C{\equiv}C-\overset{O}{\overset{\|}{C}}-$ | H | H | H | H | O | $CH_3-$ | $CH_3-$ |
| $ClCH_2\overset{O}{\overset{\|}{C}}-$ | H | H | H | H | O | $CH_3-$ | $CH_3-$ |
| $BrCH_2CH_2\overset{O}{\overset{\|}{C}}-$ | H | H | H | H | O | $CH_3-$ | $CH_3-$ |
| $CF_3\overset{O}{\overset{\|}{C}}-$ | H | H | H | H | O | $CH_3-$ | $CH_3-$ |
| $CH_3OCH_2\overset{O}{\overset{\|}{C}}-$ | H | H | H | H | O | $CH_3-$ | $CH_3-$ |
| $NCCH_2\overset{O}{\overset{\|}{C}}-$ | H | H | H | H | O | $CH_3-$ | $CH_3-$ |
| $CH_3O\overset{O}{\overset{\|}{C}}-\overset{O}{\overset{\|}{C}}-$ | H | H | H | H | O | $CH_3-$ | $CH_3-$ |
| $C_2H_5O-\overset{O}{\overset{\|}{C}}-CH_2\overset{O}{\overset{\|}{C}}-$ | H | H | H | H | O | $CH_3-$ | $CH_3-$ |
| $CH_3O\overset{O}{\overset{\|}{C}}(CH_2)_3\overset{O}{\overset{\|}{C}}-$ | H | H | H | H | O | $CH_3-$ | $CH_3-$ |
| $ClCH_2CH{=}CH-\overset{O}{\overset{\|}{C}}-$ | H | H | H | H | O | $CH_3-$ | $CH_3-$ |

TABLE IV-continued
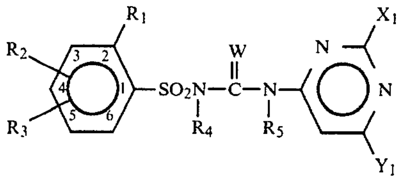
| $R_1$ | $R_2$ | $R_3$ | $R_4$ | $R_5$ | W | $X_1$ | $Y_1$ |
|---|---|---|---|---|---|---|---|
| 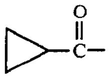 | H | H | H | H | O | $CH_3-$ | $CH_3-$ |
| 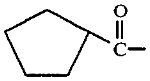 | H | H | H | H | O | $CH_3-$ | $CH_3-$ |
| 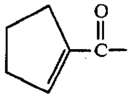 | H | H | H | H | O | $CH_3-$ | $CH_3-$ |
| 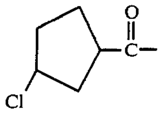 | H | H | H | H | O | $CH_3-$ | $CH_3-$ |
| 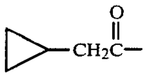 | H | H | H | H | O | $CH_3-$ | $CH_3-$ |
| 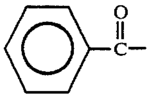 | H | H | H | H | O | $CH_3-$ | $CH_3-$ |
| 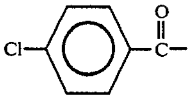 | H | H | H | H | O | $CH_3-$ | $CH_3-$ |
| 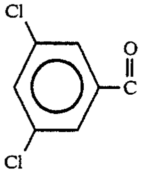 | H | H | H | H | O | $CH_3-$ | $CH_3-$ |
| 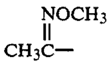 | H | H | H | H | O | $CH_3O-$ | $CH_3-$ |
| 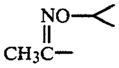 | H | H | H | H | O | $CH_3-$ | $CH_3-$ |
| 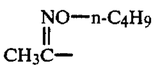 | H | H | H | H | O | $CH_3-$ | $CH_3-$ |
| 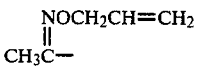 | H | H | H | H | O | $CH_3-$ | $CH_3-$ |
| 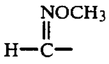 | H | H | H | H | O | $CH_3-$ | $CH_3-$ |
| 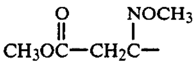 | H | H | H | H | O | $CH_3-$ | $CH_3-$ |

TABLE IV-continued
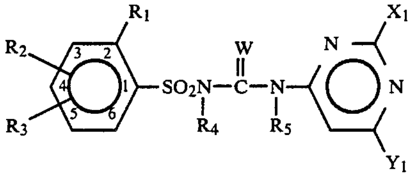
| R1 | R2 | R3 | R4 | R5 | W | X1 | Y1 |
|---|---|---|---|---|---|---|---|
| 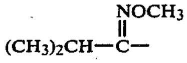 | H | H | H | H | O | $CH_3-$ | $CH_3-$ |
| 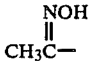 | H | H | H | H | O | $CH_3-$ | $CH_3-$ |
| 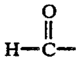 | H | H | H | H | O | $CH_3-$ | $CH_3-$ |
| 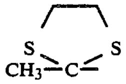 | H | H | H | H | O | $CH_3-$ | $CH_3-$ |
| 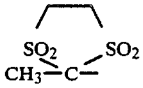 | H | H | H | H | O | $CH_3-$ | $CH_3-$ |
| 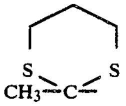 | H | H | H | H | O | $CH_3-$ | $CH_3-$ |
| 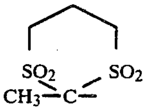 | H | H | H | H | O | $CH_3-$ | $CH_3-$ |
| 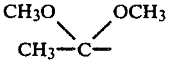 | H | H | H | H | O | $CH_3-$ | $CH_3-$ |
| 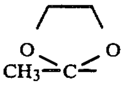 | H | H | H | H | O | $CH_3-$ | $CH_3-$ |
| 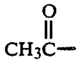 | H | H | H | H | O | H | H |
| 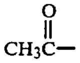 | H | H | H | H | O | H | $CH_3O-$ |
| 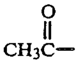 | H | H | H | H | O | H | $CH_3-$ |
| 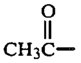 | H | H | H | H | O | Cl | H— |
| 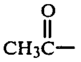 | H | H | H | H | O | Cl | $CH_3O-$ |
| 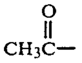 | H | H | H | H | O | Cl | $CH_3-$ |
| 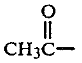 | H | H | H | H | O | $CH_3CH_2O-$ | H— |

TABLE IV-continued
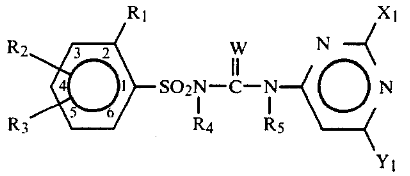
| $R_1$ | $R_2$ | $R_3$ | $R_4$ | $R_5$ | W | $X_1$ | $Y_1$ |
|---|---|---|---|---|---|---|---|
| 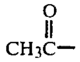 | H | H | H | H | O | $CH_3CH_2O-$ | $CH_3-$ |
| 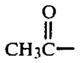 | H | H | H | H | O | $CH_3CH_2O-$ | $CH_3O-$ |
| 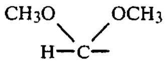 | H | H | H | H | O | $CH_3CH_2O-$ | $CH_3O-$ |
| 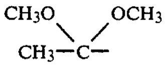 | H | H | H | H | O | $CH_3CH_2O-$ | $CH_3O-$ |
| 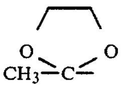 | H | H | H | H | O | $CH_3CH_2O-$ | $CH_3O-$ |
| 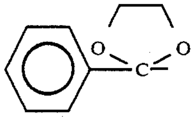 | H | H | H | H | O | $CH_3CH_2O-$ | $CH_3O-$ |
TABLE V
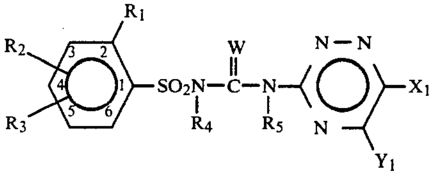
| $R_1$ | $R_2$ | $R_3$ | $R_4$ | $R_5$ | W | $X_1$ | $Y_1$ |
|---|---|---|---|---|---|---|---|
| 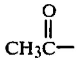 | H | H | H | H | O | $CH_3O-$ | $CH_3O-$ |
| 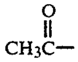 | H | H | H | H | O | $CH_3O-$ | $CH_3-$ |
| 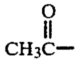 | H | H | H | H | O | $CH_3-$ | $CH_3-$ |
| 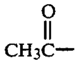 | H | H | H | H | S | $CH_3-$ | $CH_3-$ |
| 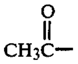 | 3-Cl | H | H | H | O | $CH_3-$ | $CH_3-$ |
| 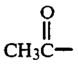 | 4-Cl | H | H | H | O | $CH_3-$ | $CH_3-$ |
| 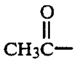 | 5-Cl | H | H | H | O | $CH_3-$ | $CH_3-$ |
| 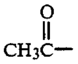 | 6-Cl | H | H | H | O | $CH_3-$ | $CH_3-$ |

TABLE V-continued

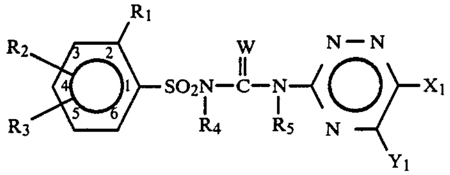

| $R_1$ | $R_2$ | $R_3$ | $R_4$ | $R_5$ | W | $X_1$ | $Y_1$ |
|---|---|---|---|---|---|---|---|
| $CH_3C(=O)-$ | 4-Cl | 5-Cl | H | H | O | $CH_3-$ | $CH_3-$ |
| $CH_3C(=O)-$ | 5-Cl | 6-$CH_3$ | H | H | O | $CH_3-$ | $CH_3-$ |
| $CH_3C(=O)-$ | 5-F | H | H | H | O | $CH_3$ | $CH_3-$ |
| $CH_3C(=O)-$ | 5-Br | H | H | H | O | $CH_3$ | $CH_3-$ |
| $CH_3C(=O)-$ | 5-$CH_3$ | H | H | H | O | $CH_3$ | $CH_3-$ |
| $CH_3C(=O)-$ | 5-i-$C_3H_7$ | H | H | H | O | $CH_3$ | $CH_3-$ |
| $CH_3C(=O)-$ | 5-$NO_2$ | H | H | H | O | $CH_3$ | $CH_3-$ |
| $CH_3C(=O)-$ | 5-$CH_3S(=O)_2-$ | H | H | H | O | $CH_3-$ | $CH_3-$ |
| $CH_3C(=O)-$ | 5-$CH_3O-$ | H | H | H | O | $CH_3-$ | $CH_3-$ |
| $CH_3C(=O)-$ | 5-$CH_3S-$ | H | H | H | O | $CH_3-$ | $CH_3-$ |
| $CH_3C(=O)-$ | 5-$CF_3-$ | H | H | H | O | $CH_3-$ | $CH_3-$ |
| $CH_3C(=O)-$ | 5-$(CH_3)_2N-$ | H | H | H | O | $CH_3-$ | $CH_3-$ |
| $CH_3C(=O)-$ | 6-$NO_2-$ | H | H | H | O | $CH_3-$ | $CH_3-$ |
| $CH_3C(=O)-$ | 6-$CF_3$ | H | H | H | O | $CH_3-$ | $CH_3-$ |
| $CH_3C(=O)-$ | 6-$CH_3S(=O)_2-$ | H | H | H | O | $CH_3-$ | $CH_3-$ |
| $CH_3CH_2-C(=O)-$ | H | H | H | H | O | $CH_3-$ | $CH_3-$ |
| $(CH_3)_2CH-C(=O)-$ | H | H | H | H | O | $CH_3-$ | $CH_3-$ |
| n-$C_5H_{11}-C(=O)-$ | H | H | H | H | O | $CH_3-$ | $CH_3-$ |

TABLE V-continued

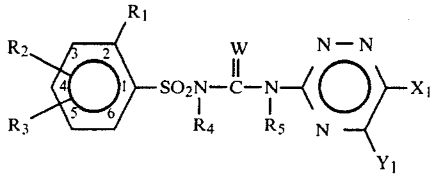

| $R_1$ | $R_2$ | $R_3$ | $R_4$ | $R_5$ | W | $X_1$ | $Y_1$ |
|---|---|---|---|---|---|---|---|
| $CH_2=CH-\overset{O}{\overset{\|}{C}}-$ | H | H | H | H | O | $CH_3-$ | $CH_3-$ |
| $CH_2=CHCH_2\overset{O}{\overset{\|}{C}}-$ | H | H | H | H | O | $CH_3-$ | $CH_3-$ |
| $CH_3C\equiv CCH_2\overset{O}{\overset{\|}{C}}-$ | H | H | H | H | O | $CH_3-$ | $CH_3-$ |
| $ClCH_2\overset{O}{\overset{\|}{C}}-$ | H | H | H | H | O | $CH_3-$ | $CH_3-$ |
| $BrCH_2CH_2\overset{O}{\overset{\|}{C}}-$ | H | H | H | H | O | $CH_3-$ | $CH_3-$ |
| $CF_3\overset{O}{\overset{\|}{C}}-$ | H | H | H | H | O | $CH_3-$ | $CH_3-$ |
| $CH_3OCH_2\overset{O}{\overset{\|}{C}}-$ | H | H | H | H | O | $CH_3-$ | $CH_3-$ |
| $NCCH_2\overset{O}{\overset{\|}{C}}-$ | H | H | H | H | O | $CH_3-$ | $CH_3-$ |
| $CH_3O\overset{O}{\overset{\|}{C}}-\overset{O}{\overset{\|}{C}}-$ | H | H | H | H | O | $CH_3-$ | $CH_3-$ |
| $C_2H_5O-\overset{O}{\overset{\|}{C}}-CH_2\overset{O}{\overset{\|}{C}}-$ | H | H | H | H | O | $CH_3-$ | $CH_3-$ |
| $CH_3O\overset{O}{\overset{\|}{C}}(CH_2)_3\overset{O}{\overset{\|}{C}}-$ | H | H | H | H | O | $CH_3-$ | $CH_3-$ |
| $ClCH_2CH=CH-\overset{O}{\overset{\|}{C}}-$ | H | H | H | H | O | $CH_3-$ | $CH_3-$ |
| 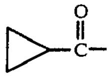 | H | H | H | H | O | $CH_3-$ | $CH_3-$ |
| 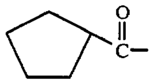 | H | H | H | H | O | $CH_3-$ | $CH_3-$ |
| 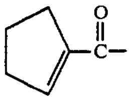 | H | H | H | H | O | $CH_3-$ | $CH_3-$ |
| 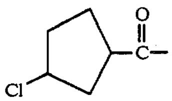 | H | H | H | H | O | $CH_3-$ | $CH_3-$ |

TABLE V-continued
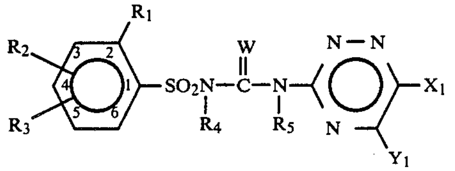
| R1 | R2 | R3 | R4 | R5 | W | X1 | Y1 |
|---|---|---|---|---|---|---|---|
| 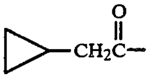 | H | H | H | H | O | $CH_3$— | $CH_3$— |
| 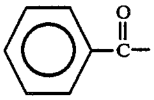 | H | H | H | H | O | $CH_3$— | $CH_3$— |
| 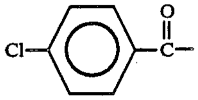 | H | H | H | H | O | $CH_3$— | $CH_3$— |
| 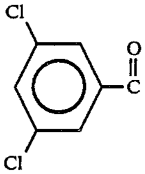 | H | H | H | H | O | $CH_3$— | $CH_3$— |
| 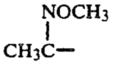 | H | H | H | H | O | $CH_3O$— | $CH_3$— |
| 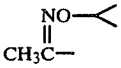 | H | H | H | H | O | $CH_3$— | $CH_3$— |
| 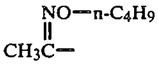 | H | H | H | H | O | $CH_3$— | $CH_3$— |
| 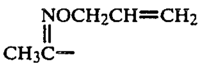 | H | H | H | H | O | $CH_3$— | $CH_3$— |
| 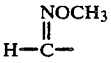 | H | H | H | H | O | $CH_3$— | $CH_3$— |
| 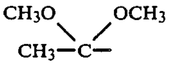 | H | H | H | H | O | $CH_3$— | $CH_3$— |
| 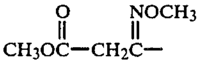 | H | H | H | H | O | $CH_3$— | $CH_3$— |
| 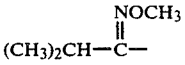 | H | H | H | H | O | $CH_3$— | $CH_3$— |
| 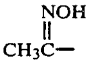 | H | H | H | H | O | $CH_3$— | $CH_3$— |
| 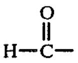 | H | H | H | H | O | $CH_3$— | $CH_3$— |
| 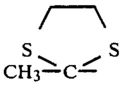 | H | H | H | H | O | $CH_3$— | $CH_3$— |

TABLE V-continued
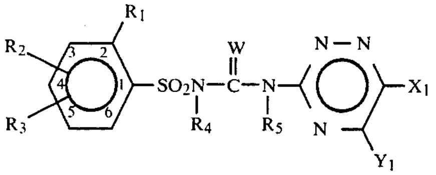
| $R_1$ | $R_2$ | $R_3$ | $R_4$ | $R_5$ | W | $X_1$ | $Y_1$ |
|---|---|---|---|---|---|---|---|
| 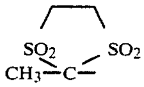 | H | H | H | H | O | $CH_3$— | $CH_3$— |
| 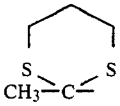 | H | H | H | H | O | $CH_3$— | $CH_3$— |
| 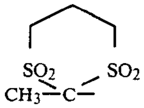 | H | H | H | H | O | $CH_3$— | $CH_3$— |
| 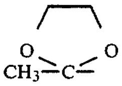 | H | H | H | H | O | $CH_3$— | $CH_3$— |
| 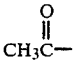 | H | H | H | H | O | H | H |
| 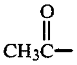 | H | H | H | H | O | H | $CH_3O$— |
| 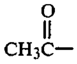 | H | H | H | H | O | H | $CH_3$— |
| 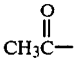 | H | H | H | H | O | Cl | H— |
| 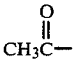 | H | H | H | H | O | Cl | $CH_3O$— |
| 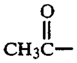 | H | H | H | H | O | Cl | $CH_3$— |
| 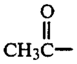 | H | H | H | H | O | $CH_3CH_2O$— | H |
| 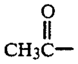 | H | H | H | H | O | $CH_3CH_2O$— | $CH_3$— |
| 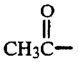 | H | H | H | H | O | $CH_3CH_2O$— | $CH_3O$— |

TABLE VI

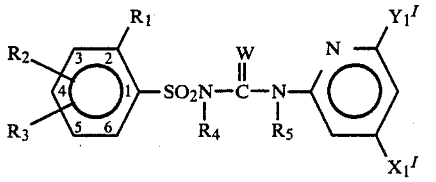

| $R_1$ | $R_2$ | $R_3$ | $R_4$ | $R_5$ | W | $X_1{}^I$ | $Y_1{}^I$ |
|---|---|---|---|---|---|---|---|
| $CH_3\overset{\overset{O}{\|}}{C}-$ | H | H | H | H | O | $CH_3O-$ | $CH_3O-$ |
| $CH_3\overset{\overset{O}{\|}}{C}-$ | H | H | H | H | O | $CH_3O-$ | $CH_3-$ |
| $CH_3\overset{\overset{O}{\|}}{C}-$ | H | H | H | H | O | $CH_3-$ | $CH_3-$ |
| $CH_3\overset{\overset{O}{\|}}{C}-$ | H | H | H | H | S | $CH_3-$ | $CH_3-$ |
| $CH_3\overset{\overset{O}{\|}}{C}-$ | 3-Cl | H | H | H | O | $CH_3-$ | $CH_3-$ |
| $CH_3\overset{\overset{O}{\|}}{C}-$ | 4-Cl | H | H | H | O | $CH_3-$ | $CH_3-$ |
| $CH_3\overset{\overset{O}{\|}}{C}-$ | 5-Cl | H | H | H | O | $CH_3-$ | $CH_3-$ |
| $CH_3\overset{\overset{O}{\|}}{C}-$ | 6-Cl | H | H | H | O | $CH_3-$ | $CH_3-$ |
| $CH_3\overset{\overset{O}{\|}}{C}-$ | 4-Cl | 5-Cl | H | H | O | $CH_3-$ | $CH_3-$ |
| $CH_3\overset{\overset{O}{\|}}{C}-$ | 5-Cl | 6-$CH_3$ | H | H | O | $CH_3-$ | $CH_3-$ |
| $CH_3\overset{\overset{O}{\|}}{C}-$ | 5-F | H | H | H | O | $CH_3$ | $CH_3-$ |
| $CH_3\overset{\overset{O}{\|}}{C}-$ | 5-Br | H | H | H | O | $CH_3$ | $CH_3-$ |
| $CH_3\overset{\overset{O}{\|}}{C}-$ | 5-$CH_3$ | H | H | H | O | $CH_3$ | $CH_3-$ |
| $CH_3\overset{\overset{O}{\|}}{C}-$ | 5-i-$C_3H_7$ | H | H | H | O | $CH_3$ | $CH_3-$ |
| $CH_3\overset{\overset{O}{\|}}{C}-$ | 5-$NO_2$ | H | H | H | O | $CH_3$ | $CH_3-$ |
| $CH_3\overset{\overset{O}{\|}}{C}-$ | 5-$CH_3\overset{\overset{O}{\|}}{\underset{\underset{O}{\|}}{S}}-$ | H | H | H | O | $CH_3-$ | $CH_3-$ |
| $CH_3\overset{\overset{O}{\|}}{C}-$ | 5-$CH_3O-$ | H | H | H | O | $CH_3-$ | $CH_3-$ |
| $CH_3\overset{\overset{O}{\|}}{C}-$ | 5-$CH_3S-$ | H | H | H | O | $CH_3-$ | $CH_3-$ |

TABLE VI-continued

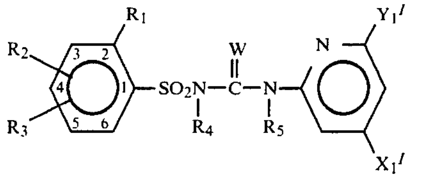

| $R_1$ | $R_2$ | $R_3$ | $R_4$ | $R_5$ | W | $X_1{}^I$ | $Y_1{}^I$ |
|---|---|---|---|---|---|---|---|
| $CH_3\overset{O}{\overset{\|}{C}}-$ | $5\text{-}CF_3-$ | H | H | H | O | $CH_3-$ | $CH_3-$ |
| $CH_3\overset{O}{\overset{\|}{C}}-$ | $5\text{-}(CH_3)_2N-$ | H | H | H | O | $CH_3-$ | $CH_3-$ |
| $CH_3\overset{O}{\overset{\|}{C}}-$ | $6\text{-}NO_2-$ | H | H | H | O | $CH_3-$ | $CH_3-$ |
| $CH_3\overset{O}{\overset{\|}{C}}-$ | $6\text{-}CF_3$ | H | H | H | O | $CH_3-$ | $CH_3-$ |
| $CH_3\overset{O}{\overset{\|}{C}}-$ | $6\text{-}CH_3\underset{\underset{O}{\|}}{\overset{O}{\overset{\|}{S}}}-$ | H | H | H | O | $CH_3-$ | $CH_3-$ |
| $CH_3CH_2-\overset{O}{\overset{\|}{C}}-$ | H | H | H | H | O | $CH_3-$ | $CH_3-$ |
| $(CH_3)_2CH-\overset{O}{\overset{\|}{C}}-$ | H | H | H | H | O | $CH_3-$ | $CH_3-$ |
| $n\text{-}C_5H_{11}-\overset{O}{\overset{\|}{C}}-$ | H | H | H | H | O | $CH_3-$ | $CH_3-$ |
| $CH_2{=}CH-\overset{O}{\overset{\|}{C}}-$ | H | H | H | H | O | $CH_3-$ | $CH_3-$ |
| $CH_2{=}CHCH_2\overset{O}{\overset{\|}{C}}-$ | H | H | H | H | O | $CH_3-$ | $CH_3-$ |
| $CH_3C{\equiv}C-H_2\overset{O}{\overset{\|}{C}}-$ | H | H | H | H | O | $CH_3-$ | $CH_3-$ |
| $ClCH_2\overset{O}{\overset{\|}{C}}-$ | H | H | H | H | O | $CH_3-$ | $CH_3-$ |
| $BrCH_2CH_2\overset{O}{\overset{\|}{C}}-$ | H | H | H | H | O | $CH_3-$ | $CH_3-$ |
| $CF_3\overset{O}{\overset{\|}{C}}-$ | H | H | H | H | O | $CH_3-$ | $CH_3-$ |
| $CH_3OCH_2\overset{O}{\overset{\|}{C}}-$ | H | H | H | H | O | $CH_3-$ | $CH_3-$ |
| $NCCH_2\overset{O}{\overset{\|}{C}}-$ | H | H | H | H | O | $CH_3-$ | $CH_3-$ |
| $CH_3O\overset{O}{\overset{\|}{C}}-\overset{O}{\overset{\|}{C}}-$ | H | H | H | H | O | $CH_3-$ | $CH_3-$ |
| $C_2H_5O-\overset{O}{\overset{\|}{C}}-CH_2\overset{O}{\overset{\|}{C}}-$ | H | H | H | H | O | $CH_3-$ | $CH_3-$ |

TABLE VI-continued
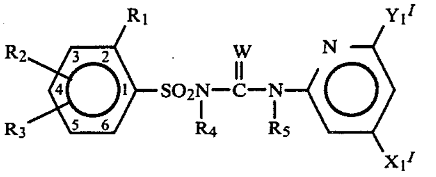
| $R_1$ | $R_2$ | $R_3$ | $R_4$ | $R_5$ | W | $X_1{}^I$ | $Y_1{}^I$ |
|---|---|---|---|---|---|---|---|
| 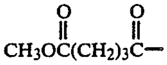 | H | H | H | H | O | $CH_3-$ | $CH_3-$ |
| 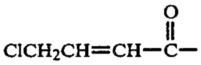 | H | H | H | H | O | $CH_3-$ | $CH_3-$ |
| 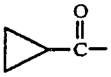 | H | H | H | H | O | $CH_3-$ | $CH_3-$ |
| 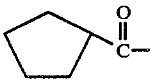 | H | H | H | H | O | $CH_3-$ | $CH_3-$ |
| 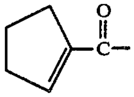 | H | H | H | H | O | $CH_3-$ | $CH_3-$ |
| 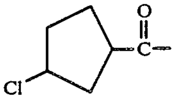 | H | H | H | H | O | $CH_3-$ | $CH_3-$ |
| 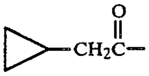 | H | H | H | H | O | $CH_3-$ | $CH_3-$ |
| 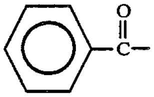 | H | H | H | H | O | $CH_3-$ | $CH_3-$ |
| 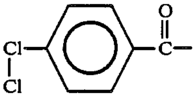 | H | H | H | H | O | $CH_3-$ | $CH_3-$ |
| 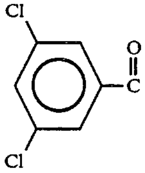 | H | H | H | H | O | $CH_3-$ | $CH_3-$ |
| 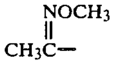 | H | H | H | H | O | $CH_3O-$ | $CH_3-$ |
| 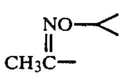 | H | H | H | H | O | $CH_3-$ | $CH_3-$ |
| 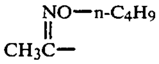 | H | H | H | H | O | $CH_3-$ | $CH_3-$ |

TABLE VI-continued
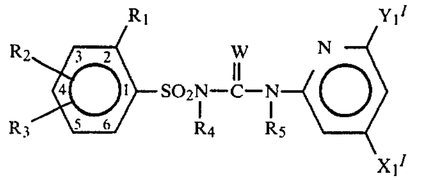
| $R_1$ | $R_2$ | $R_3$ | $R_4$ | $R_5$ | W | $X_1{}^I$ | $Y_1{}^I$ |
|---|---|---|---|---|---|---|---|
| 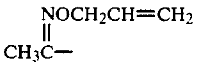 | H | H | H | H | O | $CH_3$— | $CH_3$— |
| 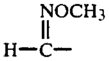 | H | H | H | H | O | $CH_3$— | $CH_3$— |
| 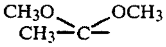 | H | H | H | H | O | $CH_3$— | $CH_3$— |
| 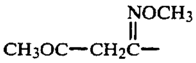 | H | H | H | H | O | $CH_3$— | $CH_3$— |
| 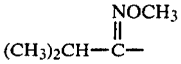 | H | H | H | H | O | $CH_3$— | $CH_3$— |
| 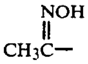 | H | H | H | H | O | $CH_3$— | $CH_3$— |
| 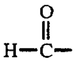 | H | H | H | H | O | $CH_3$— | $CH_3$— |
| 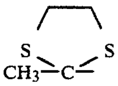 | H | H | H | H | O | $CH_3$— | $CH_3$ |
| 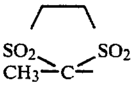 | H | H | H | H | O | $CH_3$— | $CH_3$— |
| 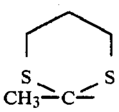 | H | H | H | H | O | $CH_3$— | $CH_3$— |
| 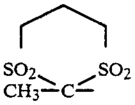 | H | H | H | H | O | $CH_3$— | $CH_3$— |
| 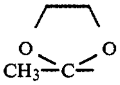 | H | H | H | H | O | $CH_3$— | $CH_3$— |

TABLE VII

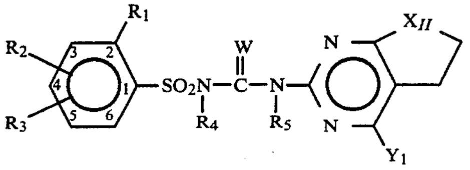

| $R_1$ | $R_2$ | $R_3$ | $R_4$ | $R_5$ | W | $X_{II}$ | $Y_1$ |
|---|---|---|---|---|---|---|---|
| $CH_3\overset{O}{\overset{\|}{C}}-$ | H | H | H | H | O | $-CH_2-$ | $CH_3O-$ |
| $CH_3\overset{O}{\overset{\|}{C}}-$ | H | H | H | H | O | $-CH_2-$ | $CH_3-$ |
| $CH_3\overset{O}{\overset{\|}{C}}-$ | H | H | H | H | O | $-O-$ | $CH_3-$ |
| $CH_3\overset{O}{\overset{\|}{C}}-$ | H | H | H | H | O | $-O-$ | $CH_3O-$ |
| $CH_3\overset{O}{\overset{\|}{C}}-$ | 3-Cl | H | H | H | O | $-O-$ | $CH_3-$ |
| $CH_3\overset{O}{\overset{\|}{C}}-$ | 4-Cl | H | H | H | O | $-O-$ | $CH_3-$ |
| $CH_3\overset{O}{\overset{\|}{C}}-$ | 5-Cl | H | H | H | O | $-O-$ | $CH_3-$ |
| $CH_3\overset{O}{\overset{\|}{C}}-$ | 6-Cl | H | H | H | O | $-O-$ | $CH_3-$ |
| $CH_3\overset{O}{\overset{\|}{C}}-$ | 4-Cl | 5-Cl | H | H | O | $-O-$ | $CH_3-$ |
| $CH_3\overset{O}{\overset{\|}{C}}-$ | 5-Cl | $6\text{-}CH_3$ | H | H | O | $-O-$ | $CH_3-$ |
| $CH_3\overset{O}{\overset{\|}{C}}-$ | 5-F | H | H | H | O | $-O-$ | $CH_3-$ |
| $CH_3\overset{O}{\overset{\|}{C}}-$ | 5-Br | H | H | H | O | $-O-$ | $CH_3-$ |
| $CH_3\overset{O}{\overset{\|}{C}}-$ | $5\text{-i-}C_3H_7$ | H | H | H | O | $-O-$ | $CH_3-$ |
| $CH_3\overset{O}{\overset{\|}{C}}-$ | $5\text{-}CH_3$ | H | H | H | O | $-O-$ | $CH_3-$ |
| $CH_3\overset{O}{\overset{\|}{C}}-$ | $5\text{-}NO_2$ | H | H | H | O | $-O-$ | $CH_3-$ |
| $CH_3\overset{O}{\overset{\|}{C}}-$ | $5\text{-}CH_3\overset{O}{\overset{\|}{\underset{O}{\underset{\|}{S}}}}-$ | H | H | H | O | $-O-$ | $CH_3-$ |
| $CH_3\overset{O}{\overset{\|}{C}}-$ | $5\text{-}CH_3O-$ | H | H | H | O | $-O-$ | $CH_3-$ |
| $CH_3\overset{O}{\overset{\|}{C}}-$ | $5\text{-}CH_3S-$ | H | H | H | O | $-O-$ | $CH_3-$ |

TABLE VII-continued

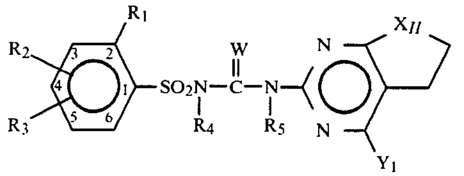

| $R_1$ | $R_2$ | $R_3$ | $R_4$ | $R_5$ | W | $X_{II}$ | $Y_1$ |
|---|---|---|---|---|---|---|---|
| $CH_3\overset{\overset{O}{\|}}{C}-$ | $5\text{-}CF_3-$ | H | H | H | O | —O— | $CH_3-$ |
| $CH_3\overset{\overset{O}{\|}}{C}-$ | $5\text{-}(CH_3)_2N-$ | H | H | H | O | —O— | $CH_3-$ |
| $CH_3\overset{\overset{O}{\|}}{C}-$ | $6\text{-}NO_2-$ | H | H | H | O | —O— | $CH_3-$ |
| $CH_3\overset{\overset{O}{\|}}{C}-$ | $6\text{-}CF_3$ | H | H | H | O | —O— | $CH_3-$ |
| $CH_3\overset{\overset{O}{\|}}{C}-$ | $6\text{-}CH_3\overset{\overset{O}{\|}}{\underset{\underset{O}{\|}}{S}}-$ | H | H | H | O | —O— | $CH_3-$ |
| $CH_3CH_2-\overset{\overset{O}{\|}}{C}-$ | H | H | H | H | O | —O— | $CH_3-$ |
| $(CH_3)_2CH-\overset{\overset{O}{\|}}{C}-$ | H | H | H | H | O | —O— | $CH_3-$ |
| $n\text{-}C_{12}H_{25}\overset{\overset{O}{\|}}{C}-$ | H | H | H | H | O | —O— | $CH_3-$ |
| $CH_2{=}CH-\overset{\overset{O}{\|}}{C}-$ | H | H | H | H | O | —O— | $CH_3-$ |
| $CH_2{=}CHCH_2\overset{\overset{O}{\|}}{C}-$ | H | H | H | H | O | —O— | $CH_3-$ |
| $CH_3C{\equiv}CCH_2\overset{\overset{O}{\|}}{C}-$ | H | H | H | H | O | —O— | $CH_3-$ |
| $ClCH_2\overset{\overset{O}{\|}}{C}-$ | H | H | H | H | O | —O— | $CH_3-$ |
| $BrCH_2CH_2\overset{\overset{O}{\|}}{C}-$ | H | H | H | H | O | —O— | $CH_3-$ |
| $CF_3\overset{\overset{O}{\|}}{C}-$ | H | H | H | H | O | —O— | $CH_3-$ |
| $CH_3OCH_2\overset{\overset{O}{\|}}{C}-$ | H | H | H | H | O | —O— | $CH_3-$ |
| $NCCH_2\overset{\overset{O}{\|}}{C}-$ | H | H | H | H | O | —O— | $CH_3-$ |
| $CH_3O\overset{\overset{O}{\|}}{C}-\overset{\overset{O}{\|}}{C}-$ | H | H | H | H | O | —O— | $CH_3-$ |

TABLE VII-continued
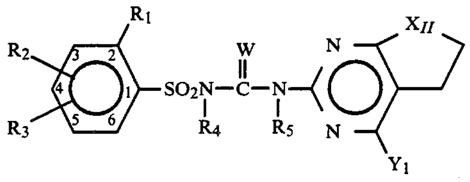
| $R_1$ | $R_2$ | $R_3$ | $R_4$ | $R_5$ | W | $X_{II}$ | $Y_1$ |
|---|---|---|---|---|---|---|---|
| 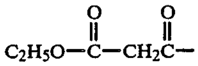 | H | H | H | H | O | —O— | $CH_3$— |
| 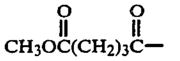 | H | H | H | H | O | —O— | $CH_3$— |
| 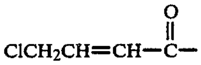 | H | H | H | H | O | —O— | $CH_3$— |
| 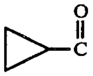 | H | H | H | H | O | —O— | $CH_3$— |
| 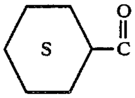 | H | H | H | H | O | —O— | $CH_3$— |
| 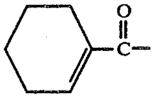 | H | H | H | H | O | —O— | $CH_3$— |
| 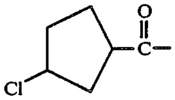 | H | H | H | H | O | —O— | $CH_3$— |
| 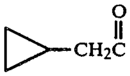 | H | H | H | H | O | —O— | $CH_3$— |
| 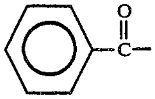 | H | H | H | H | O | —O— | $CH_3$— |
| 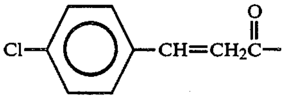 | H | H | H | H | O | —O— | $CH_3$— |
| 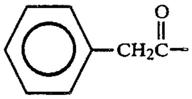 | H | H | H | H | O | —O— | $CH_3$— |
| 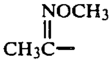 | H | H | H | H | O | —O— | $CH_3$— |
| 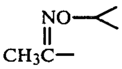 | H | H | H | H | O | —O— | $CH_3$— |
| 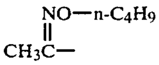 | H | H | H | H | O | —O— | $CH_3$— |

TABLE VII-continued
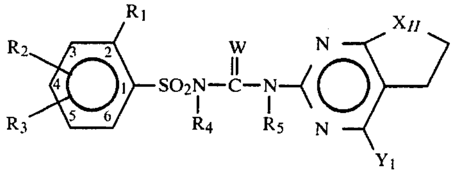
| $R_1$ | $R_2$ | $R_3$ | $R_4$ | $R_5$ | W | $X_{II}$ | $Y_1$ |
|---|---|---|---|---|---|---|---|
| 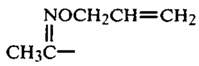 | H | H | H | H | O | —O— | $CH_3$— |
| 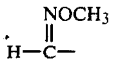 | H | H | H | H | O | —O— | $CH_3$— |
| 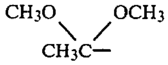 | H | H | H | H | O | —O— | $CH_3$— |
| 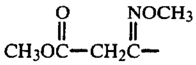 | H | H | H | H | O | —O— | $CH_3$— |
| 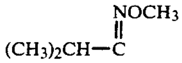 | H | H | H | H | O | —O— | $CH_3$— |
| 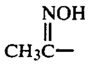 | H | H | H | H | O | —O— | $CH_3$— |
| 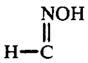 | H | H | H | H | O | —O— | $CH_3$— |
| 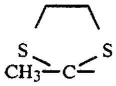 | H | H | H | H | O | —O— | $CH_3$— |
| 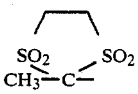 | H | H | H | H | O | —O— | $CH_3$— |
| 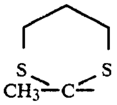 | H | H | H | H | O | —O— | $CH_3$— |
| 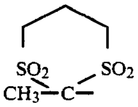 | H | H | H | H | O | —O— | $CH_3$— |
| 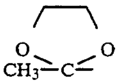 | H | H | H | H | O | —O— | $CH_3$— |
| 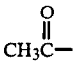 | H | H | H | H | O | —O— | H— |
| 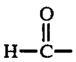 | H | H | H | H | O | —O— | $CH_3O$— |
| 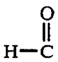 | H | H | H | H | O | —O— | CH— |
| 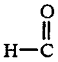 | H | H | H | H | O | —O— | H— |

TABLE VII-continued

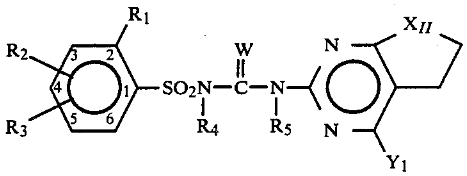

| $R_1$ | $R_2$ | $R_3$ | $R_4$ | $R_5$ | W | $X_{II}$ | $Y_1$ |
|---|---|---|---|---|---|---|---|
| $CH_3\overset{NOCH_3}{\overset{\|}{C}}-$ | H | H | H | H | O | —O— | $CH_3O-$ |
| $CH_3\overset{NOH}{\overset{\|}{C}}-$ | H | H | H | H | O | —O— | $CH_3O-$ |
| $CH_3CH_2\overset{O}{\overset{\|}{C}}-$ | H | H | H | H | O | —O— | $CH_3O-$ |
| $(CH_3)_2CH\overset{O}{\overset{\|}{C}}-$ | H | H | H | H | O | —O— | $CH_3O-$ |
| 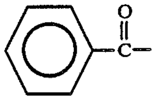 | H | H | H | H | O | —O— | $CH_3O-$ |
| $CH_3\overset{O}{\overset{\|}{C}}-$ | H | H | H | H | S | —O— | $CH_3-$ |
| $CH_3\overset{O}{\overset{\|}{C}}-$ | H | H | H | H | S | $-CH_2-$ | $CH_3-$ |
| $CH_3\overset{O}{\overset{\|}{C}}-$ | H | H | H | $CH_3$ | O | —O— | $CH_3-$ |
| $CH_3\overset{O}{\overset{\|}{C}}-$ | H | H | H | $CH_3O$ | O | —O— | $CH_3-$ |
| $CH_3\overset{O}{\overset{\|}{C}}-$ | H | H | $CH_3$ | H | O | —O— | $CH_3-$ |
| $CH_3\overset{O}{\overset{\|}{C}}-$ | H | H | $CH_3$ | $CH_3$ | O | —O— | $CH_3-$ |

TABLE VIII

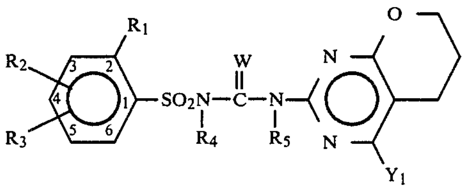

| $R_1$ | $R_2$ | $R_3$ | $R_4$ | $R_5$ | W | $Y_1$ |
|---|---|---|---|---|---|---|
| $CH_3\overset{O}{\overset{\|}{C}}-$ | H | H | H | H | O | $CH_3O-$ |
| $CH_3\overset{O}{\overset{\|}{C}}-$ | H | H | H | H | O | $CH_3-$ |
| $CH_3\overset{O}{\overset{\|}{C}}-$ | H | H | H | H | O | $CH_3-$ |

TABLE VIII-continued

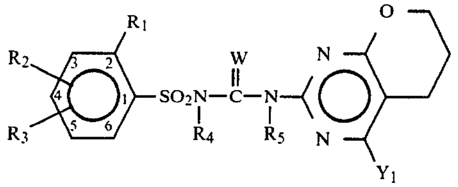

| $R_1$ | $R_2$ | $R_3$ | $R_4$ | $R_5$ | W | $Y_1$ |
|---|---|---|---|---|---|---|
| $CH_3\overset{\overset{O}{\|}}{C}-$ | H | H | H | H | O | $CH_3O-$ |
| $CH_3\overset{\overset{O}{\|}}{C}-$ | 3-Cl | H | H | H | O | $CH_3-$ |
| $CH_3\overset{\overset{O}{\|}}{C}-$ | 4-Cl | H | H | H | O | $CH_3-$ |
| $CH_3\overset{\overset{O}{\|}}{C}-$ | 5-Cl | H | H | H | O | $CH_3-$ |
| $CH_3\overset{\overset{O}{\|}}{C}-$ | 6-Cl | H | H | H | O | $CH_3-$ |
| $CH_3\overset{\overset{O}{\|}}{C}-$ | 4-Cl | 5-Cl | H | H | O | $CH_3-$ |
| $CH_3\overset{\overset{O}{\|}}{C}-$ | 5-Cl | 6-$CH_3$ | H | H | O | $CH_3-$ |
| $CH_3\overset{\overset{O}{\|}}{C}-$ | 5-F | H | H | H | O | $CH_3-$ |
| $CH_3\overset{\overset{O}{\|}}{C}-$ | 5-Br | H | H | H | O | $CH_3-$ |
| $CH_3\overset{\overset{O}{\|}}{C}-$ | 5-i-$C_3H_7$ | H | H | H | O | $CH_3-$ |
| $CH_3\overset{\overset{O}{\|}}{C}-$ | 5-$CH_3$ | H | H | H | O | $CH_3-$ |
| $CH_3\overset{\overset{O}{\|}}{C}-$ | 5-$NO_2$ | H | H | H | O | $CH_3-$ |
| $CH_3\overset{\overset{O}{\|}}{C}-$ | 5-$CH_3\underset{\underset{O}{\|}}{\overset{\overset{O}{\|}}{S}}-$ | H | H | H | O | $CH_3-$ |
| $CH_3\overset{\overset{O}{\|}}{C}-$ | 5-$CH_3O-$ | H | H | H | O | $CH_3-$ |
| $CH_3\overset{\overset{O}{\|}}{C}-$ | 5-$CH_3S-$ | H | H | H | O | $CH_3-$ |
| $CH_3\overset{\overset{O}{\|}}{C}-$ | 5-$CF_3-$ | H | H | H | O | $CH_3-$ |
| $CH_3\overset{\overset{O}{\|}}{C}-$ | 5-$(CH_3)_2N-$ | H | H | H | O | $CH_3-$ |
| $CH_3\overset{\overset{O}{\|}}{C}-$ | 6-$NO_2$ | H | H | H | O | $CH_3-$ |

TABLE VIII-continued

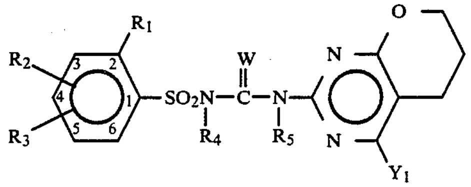

| $R_1$ | $R_2$ | $R_3$ | $R_4$ | $R_5$ | W | $Y_1$ |
|---|---|---|---|---|---|---|
| $CH_3\overset{O}{\overset{\|}{C}}-$ | 6-$CF_3$ | H | H | H | O | $CH_3-$ |
| $CH_3\overset{O}{\overset{\|}{C}}-$ | 6-$CH_3\underset{O}{\underset{\|}{\overset{O}{\overset{\|}{S}}}}-$ | H | H | H | O | $CH_3-$ |
| $CH_3CH_2-\overset{O}{\overset{\|}{C}}-$ | H | H | H | H | O | $CH_3-$ |
| $(CH_3)_2CH-\overset{O}{\overset{\|}{C}}-$ | H | H | H | H | O | $CH_3-$ |
| n-$C_{12}H_{25}\overset{O}{\overset{\|}{C}}-$ | H | H | H | H | O | $CH_3-$ |
| $CH_2{=}CH-\overset{O}{\overset{\|}{C}}-$ | H | H | H | H | O | $CH_3-$ |
| $CH_2{=}CHCH_2\overset{O}{\overset{\|}{C}}-$ | H | H | H | H | O | $CH_3-$ |
| $CH_3C{\equiv}CCH_2\overset{O}{\overset{\|}{C}}-$ | H | H | H | H | O | $CH_3-$ |
| $ClCH_2\overset{O}{\overset{\|}{C}}-$ | H | H | H | H | O | $CH_3-$ |
| $BrCH_2CH_2\overset{O}{\overset{\|}{C}}-$ | H | H | H | H | O | $CH_3-$ |
| $CF_3\overset{O}{\overset{\|}{C}}-$ | H | H | H | H | O | $CH_3-$ |
| $CH_3OCH_2\overset{O}{\overset{\|}{C}}-$ | H | H | H | H | O | $CH_3-$ |
| $NCCH_2\overset{O}{\overset{\|}{C}}-$ | H | H | H | H | O | $CH_3-$ |
| $CH_3O\overset{O}{\overset{\|}{C}}-\overset{O}{\overset{\|}{C}}-$ | H | H | H | H | O | $CH_3-$ |
| $C_2H_5O-\overset{O}{\overset{\|}{C}}-CH_2\overset{O}{\overset{\|}{C}}-$ | H | H | H | H | O | $CH_3-$ |
| $CH_3O\overset{O}{\overset{\|}{C}}(CH_2)_3\overset{O}{\overset{\|}{C}}-$ | H | H | H | H | O | $CH_3-$ |
| $ClCH_2CH{=}CH-\overset{O}{\overset{\|}{C}}-$ | H | H | H | H | O | $CH_3-$ |

TABLE VIII-continued
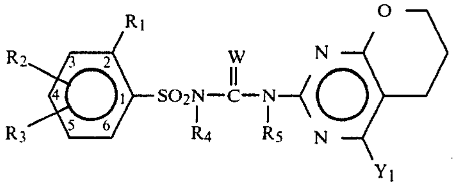
| $R_1$ | $R_2$ | $R_3$ | $R_4$ | $R_5$ | W | $Y_1$ |
|---|---|---|---|---|---|---|
| 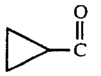 | H | H | H | H | O | $CH_3$— |
| 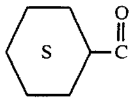 | H | H | H | H | O | $CH_3$— |
| 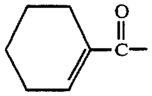 | H | H | H | H | O | $CH_3$— |
| 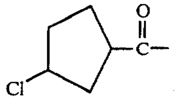 | H | H | H | H | O | $CH_3$— |
| 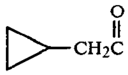 | H | H | H | H | O | $CH_3$— |
| 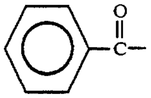 | H | H | H | H | O | $CH_3$— |
| 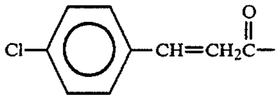 | H | H | H | H | O | $CH_3$— |
| 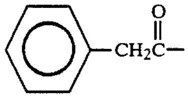 | H | H | H | H | O | $CH_3$— |
| 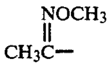 | H | H | H | H | O | $CH_3$— |
| 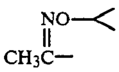 | H | H | H | H | O | $CH_3$— |
| 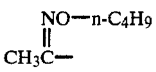 | H | H | H | H | O | $CH_3$— |
| 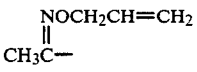 | H | H | H | H | O | $CH_3$— |
| 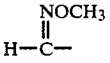 | H | H | H | H | O | $CH_3$— |
| 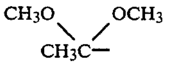 | H | H | H | H | O | $CH_3$— |

TABLE VIII-continued

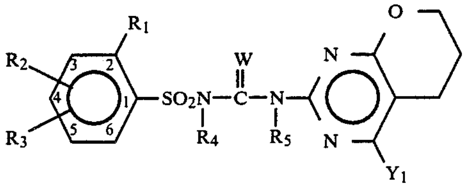

| $R_1$ | $R_2$ | $R_3$ | $R_4$ | $R_5$ | W | $Y_1$ |
|---|---|---|---|---|---|---|
| O NOCH₃<br>‖ ‖<br>$CH_3OC—CH_2C—$ | H | H | H | H | O | $CH_3—$ |
| NOCH₃<br>‖<br>$(CH_3)_2CN—C$ | H | H | H | H | O | $CH_3—$ |
| NOH<br>‖<br>$CH_3C—$ | H | H | H | H | O | $CH_3—$ |
| NOH<br>‖<br>H—C | H | H | H | H | O | $CH_3—$ |
| 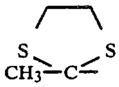 | H | H | H | H | O | $CH_3—$ |
| 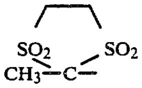 | H | H | H | H | O | $CH_3—$ |
| 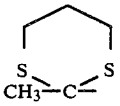 | H | H | H | H | O | $CH_3—$ |
| 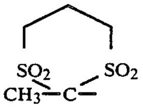 | H | H | H | H | O | $CH_3—$ |
| 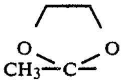 | H | H | H | H | O | $CH_3—$ |
| O<br>‖<br>$CH_3C—$ | H | H | H | H | O | H— |
| O<br>‖<br>H—C— | H | H | H | H | O | $CH_3O—$ |
| O<br>‖<br>H—C | H | H | H | H | O | CH— |
| O<br>‖<br>H—C | H | H | H | H | O | H— |
| NOCH₃<br>‖<br>$CH_3C—$ | H | H | H | H | O | $CH_3O—$ |
| NOH<br>‖<br>$CH_3C—$ | H | H | H | H | O | $CH_3O—$ |
| O<br>‖<br>$CH_3CH_2C—$ | H | H | H | H | O | $CH_3O—$ |

TABLE VIII-continued

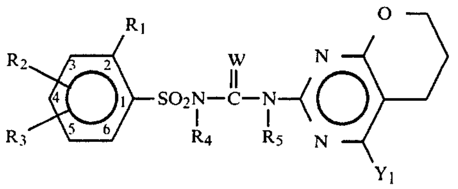

| $R_1$ | $R_2$ | $R_3$ | $R_4$ | $R_5$ | W | $Y_1$ |
|---|---|---|---|---|---|---|
| $(CH_3)_2CH\overset{\overset{O}{\parallel}}{C}-$ | H | H | H | H | O | $CH_3O-$ |
| 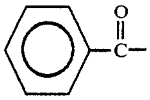 | H | H | H | H | O | $CH_3O-$ |
| $CH_3\overset{\overset{O}{\parallel}}{C}-$ | H | H | H | H | S | $CH_3-$ |
| $CH_3\overset{\overset{O}{\parallel}}{C}-$ | H | H | H | H | S | $CH_3-$ |
| $CH_3\overset{\overset{O}{\parallel}}{C}-$ | H | H | H | $CH_3$ | O | $CH_3-$ |
| $CH_3\overset{\overset{O}{\parallel}}{C}-$ | H | H | H | $CH_3O$ | O | $CH_3-$ |
| $CH_3\overset{\overset{O}{\parallel}}{C}-$ | H | H | $CH_3$ | H | O | $CH_3-$ |
| $CH_3\overset{\overset{O}{\parallel}}{C}-$ | H | H | $CH_3$ | $CH_3$ | O | $CH_3-$ |

TABLE IX

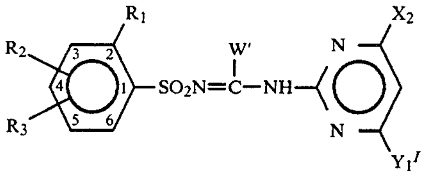

| $R_1$ | $R_2$ | $R_3$ | W' | $X_2$ | $Y_1^I$ |
|---|---|---|---|---|---|
| $CH_3\overset{\overset{O}{\parallel}}{C}-$ | H | H | $-OCH_3$ | $CH_3$ | $CH_3$ |
| $CH_3\overset{\overset{O}{\parallel}}{C}-$ | H | H | $-OCH_3$ | $CH_3O$ | $CH_3$ |
| $CH_3\overset{\overset{O}{\parallel}}{C}-$ | H | H | $-OCH_3$ | $CH_3O$ | $CH_3O$ |
| $CH_3\overset{\overset{O}{\parallel}}{C}-$ | H | H | $-SCH_3$ | $CH_3$ | $CH_3$ |
| $CH_3\overset{\overset{O}{\parallel}}{C}-$ | H | H | $-SCH_3$ | $CH_3O$ | $CH_3$ |

TABLE IX-continued

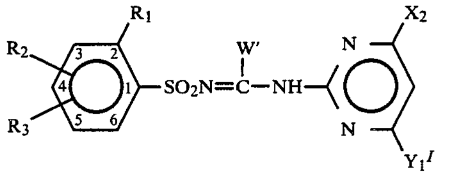

| $R_1$ | $R_2$ | $R_3$ | W' | $X_2$ | $Y_1^I$ |
|---|---|---|---|---|---|
| $CH_3\overset{O}{\overset{\|}{C}}-$ | H | H | $-SCH_3$ | $CH_3O$ | $CH_3O$ |
| $CH_3\overset{O}{\overset{\|}{C}}-$ | H | H | $-SCH(CH_3)_2$ | $CH_3$ | $CH_3O$ |
| $CH_3\overset{O}{\overset{\|}{C}}-$ | H | H | $-SC_{12}H_{25}$ | $CH_3$ | $CH_3O$ |
| $CH_3\overset{O}{\overset{\|}{C}}-$ | H | H | $-SCH_2CH{=}CH_2$ | $CH_3$ | $CH_3O$ |
| $CH_3\overset{O}{\overset{\|}{C}}-$ | H | H | $-SCH_2CH_2OCH_3$ | $CH_3$ | $CH_3O$ |
| $CH_3\overset{O}{\overset{\|}{C}}-$ | H | H | $-SCH_2CH_2OCH_2CH_3$ | $CH_3$ | $CH_3O$ |
| $CH_3\overset{O}{\overset{\|}{C}}-$ | H | H | $-S(CH_2)_3OCH_3$ | $CH_3$ | $CH_3O$ |
| $CH_3\overset{O}{\overset{\|}{C}}-$ | H | H | $-SCH_2-$ 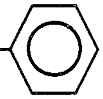 | $CH_3$ | $CH_3O$ |
| $CH_3\overset{O}{\overset{\|}{C}}-$ | H | H | $-SCH_2CO_2CH_3$ | $CH_3$ | $CH_3O$ |
| $CH_3\overset{O}{\overset{\|}{C}}-$ | H | H | $-S\underset{CH_3}{\underset{\|}{C}}HCO_2CH_3$ | $CH_3$ | $CH_3O$ |
| $CH_3\overset{O}{\overset{\|}{C}}-$ | H | H | $-SCH_2CO_2-$ 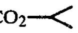 | $CH_3$ | $CH_3O$ |
| $CH_3\overset{O}{\overset{\|}{C}}-$ | H | H | $-S\underset{CH_3}{\underset{\|}{C}}HCO_2-n\text{-}C_4H_9$ | $CH_3$ | $CH_3O$ |
| $CH_3\overset{O}{\overset{\|}{C}}-$ | H | H | $-SCH_2\overset{O}{\overset{\|}{C}}NH_2$ | $CH_3$ | $CH_3O$ |
| $CH_3\overset{O}{\overset{\|}{C}}-$ | H | H | $-SCH_2\overset{O}{\overset{\|}{C}}NHCH_2CH_3$ | $CH_3$ | $CH_3O$ |
| $CH_3\overset{O}{\overset{\|}{C}}-$ | H | H | $-SCH_2\overset{O}{\overset{\|}{C}}N(C_4H_9)_2$ | $CH_3$ | $CH_3O$ |
| $CH_3\overset{O}{\overset{\|}{C}}-$ | H | H | $-S\underset{CH_3}{\underset{\|}{C}}H\overset{O}{\overset{\|}{C}}N(CH_3)_2$ | $CH_3$ | $CH_3O$ |
| $CH_3\overset{O}{\overset{\|}{C}}-$ | H | H | $-S\underset{CH_3}{\underset{\|}{C}}H-\overset{O}{\overset{\|}{C}}\underset{CH_3}{\underset{\|}{N}}-OCH_3$ | $CH_3$ | $CH_3O$ |

TABLE IX-continued

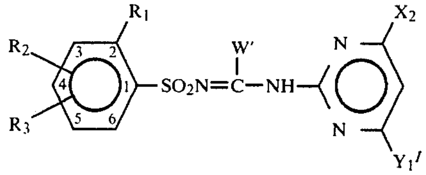

| $R_1$ | $R_2$ | $R_3$ | W' | $X_2$ | $Y_1{}^I$ |
|---|---|---|---|---|---|
| $CH_3\overset{O}{\overset{\|}{C}}-$ | H | H | $-SCH_2CN$ | $CH_3$ | $CH_3O$ |
| $CH_3\overset{O}{\overset{\|}{C}}-$ | H | H | $-SCH_2CH{=}CH-CH_3$ | $CH_3$ | $CH_3O$ |
| $CH_3\overset{O}{\overset{\|}{C}}-$ | H | H | $-SCH_2C{\equiv}C-CH_3$ | $CH_3$ | $CH_3O$ |
| $CH_3\overset{O}{\overset{\|}{C}}-$ | H | H | 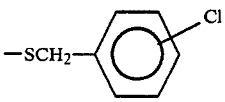 | $CH_3$ | $CH_3O$ |
| $CH_3\overset{O}{\overset{\|}{C}}-$ | H | H | $-\underset{CH_3}{SCH}-\overset{O}{\overset{\|}{C}}NHCH_3$ | $CH_3$ | $CH_3O$ |
| $CH_3\overset{O}{\overset{\|}{C}}-$ | H | H | 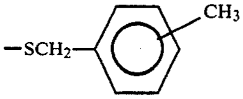 | $CH_3$ | $CH_3O$ |
| $CH_3\overset{O}{\overset{\|}{C}}-$ | H | H | $-\underset{CH_3}{SCH}-CO_2CH_3$ | $CH_3$ | $CH_3O$ |
| $CH_3\overset{O}{\overset{\|}{C}}-$ | 3-Cl | H | $-\underset{CH_3}{SCH}-CO_2CH_3$ | $CH_3$ | $CH_3O$ |
| $CH_3\overset{O}{\overset{\|}{C}}-$ | 4-Cl | H | $-\underset{CH_3}{SCH}-CO_2CH_3$ | $CH_3$ | $CH_3O$ |
| $CH_3\overset{O}{\overset{\|}{C}}-$ | 5-Cl | H | $-\underset{CH_3}{SCH}-CO_2CH_3$ | $CH_3$ | $CH_3O$ |
| $CH_3\overset{O}{\overset{\|}{C}}-$ | 6-Cl | H | $-\underset{CH_3}{SCH}-CO_2CH_3$ | $CH_3$ | $CH_3O$ |
| $CH_3\overset{O}{\overset{\|}{C}}-$ | 4-Cl | 5-Cl | $-\underset{CH_3}{SCH}-CO_2CH_3$ | $CH_3$ | $CH_3O$ |
| $CH_3\overset{O}{\overset{\|}{C}}-$ | 5-Cl | 6-$CH_3$ | $-\underset{CH_3}{SCH}-CO_2CH_3$ | $CH_3$ | $CH_3O$ |
| $CH_3\overset{O}{\overset{\|}{C}}-$ | 5-F | H | $-\underset{CH_3}{SCH}-CO_2CH_3$ | $CH_3$ | $CH_3O$ |
| $CH_3\overset{O}{\overset{\|}{C}}-$ | 5-$CH_3$ | H | $-\underset{CH_3}{SCH}-CO_2CH_3$ | $CH_3$ | $CH_3O$ |
| $CH_3\overset{O}{\overset{\|}{C}}-$ | 5-i-$C_3H_7$ | H | $-\underset{CH_3}{SCH}-CO_2CH_3$ | $CH_3$ | $CH_3O$ |

TABLE IX-continued

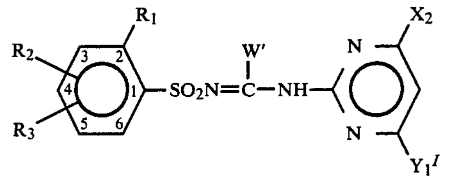

| $R_1$ | $R_2$ | $R_3$ | W' | $X_2$ | $Y_1{}^I$ |
|---|---|---|---|---|---|
| $CH_3\overset{O}{\overset{\|}{C}}-$ | 5-$NO_2$ | H | $-S\underset{CH_3}{\underset{\|}{C}}H-CO_2CH_3$ | $CH_3$ | $CH_3O$ |
| $CH_3\overset{O}{\overset{\|}{C}}-$ | 5-$CH_3\overset{O}{\overset{\|}{\underset{O}{\underset{\|}{S}}}}-$ | H | $-S\underset{CH_3}{\underset{\|}{C}}H-CO_2CH_3$ | $CH_3$ | $CH_3O$ |
| $CH_3\overset{O}{\overset{\|}{C}}-$ | 5-$CH_3S-$ | H | $-S\underset{CH_3}{\underset{\|}{C}}H-CO_2CH_3$ | $CH_3$ | $CH_3O$ |
| $CH_3\overset{O}{\overset{\|}{C}}-$ | 5-$CF_3$ | H | $-S\underset{CH_3}{\underset{\|}{C}}H-CO_2CH_3$ | $CH_3$ | $CH_3O$ |
| $CH_3\overset{O}{\overset{\|}{C}}-$ | 5-$(CH_3)_2N-$ | H | $-S\underset{CH_3}{\underset{\|}{C}}H-CO_2CH_3$ | $CH_3$ | $CH_3O$ |
| $CH_3\overset{O}{\overset{\|}{C}}-$ | 6-$NO_2$ | H | $-S\underset{CH_3}{\underset{\|}{C}}H-CO_2CH_3$ | $CH_3$ | $CH_3O$ |
| $CH_3\overset{O}{\overset{\|}{C}}-$ | 6-$CF_3$ | H | $-S\underset{CH_3}{\underset{\|}{C}}H-CO_2CH_3$ | $CH_3$ | $CH_3O$ |
| $CH_3\overset{O}{\overset{\|}{C}}-$ | 6-$CH_3\overset{O}{\overset{\|}{\underset{O}{\underset{\|}{S}}}}-$ | H | $-S\underset{CH_3}{\underset{\|}{C}}H-CO_2CH_3$ | $CH_3$ | $CH_3O$ |
| $CH_3\overset{O}{\overset{\|}{C}}-$ | H | H | $-S\underset{CH_3}{\underset{\|}{C}}H-CO_2CH_3$ | $CH_3CH_2O-$ | $CH_3$ |
| $CH_3\overset{O}{\overset{\|}{C}}-$ | H | H | $-S\underset{CH_3}{\underset{\|}{C}}H-CO_2CH_3$ | $C_4H_9O-$ | $CH_3$ |
| $CH_3\overset{O}{\overset{\|}{C}}-$ | H | H | $-S\underset{CH_3}{\underset{\|}{C}}H-CO_2CH_3$ | $CH_3OCH_2O-$ | $CH_3$ |
| $CH_3\overset{O}{\overset{\|}{C}}-$ | H | H | $-S\underset{CH_3}{\underset{\|}{C}}H-CO_2CH_3$ | $CH_3O(CH_2)_3O-$ | $CH_3$ |
| $CH_3\overset{O}{\overset{\|}{C}}-$ | H | H | $-S\underset{CH_3}{\underset{\|}{C}}H-CO_2CH_3$ | $\succ\!-OCH_2O-$ | $CH_3$ |
| $CH_3\overset{O}{\overset{\|}{C}}-$ | H | H | $-S\underset{CH_3}{\underset{\|}{C}}H-CO_2CH_3$ | $CH_3O\overset{O}{\overset{\|}{C}}CH_2O-$ | $CH_3$ |
| $CH_3\overset{O}{\overset{\|}{C}}-$ | H | H | $-S\underset{CH_3}{\underset{\|}{C}}H-CO_2CH_3$ | $CH_3O\overset{O}{\overset{\|}{C}}\underset{CH_3}{\underset{\|}{C}}H-O-$ | $CH_3$ |
| $CH_3\overset{O}{\overset{\|}{C}}-$ | H | H | $-S\underset{CH_3}{\underset{\|}{C}}H-CO_2CH_3$ | $C_3H_7O\overset{O}{\overset{\|}{C}}CH_2O-$ | $CH_3$ |

TABLE IX-continued

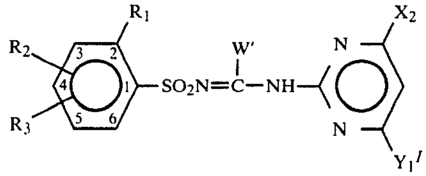

| $R_1$ | $R_2$ | $R_3$ | W' | $X_2$ | $Y_1{}^I$ |
|---|---|---|---|---|---|
| $CH_3\overset{O}{\overset{\|}{C}}-$ | H | H | $-S\underset{CH_3}{\underset{\|}{C}}H-CO_2CH_3$ | $CF_3CH_2O-$ | $CH_3$ |
| $CH_3\overset{O}{\overset{\|}{C}}-$ | H | H | $-S\underset{CH_3}{\underset{\|}{C}}H-CO_2CH_3$ | $CCl_3CH_2O-$ | $CH_3$ |
| $CH_3\overset{O}{\overset{\|}{C}}-$ | H | H | $-S\underset{CH_3}{\underset{\|}{C}}H-CO_2CH_3$ | $CH_3O-$ | $CH_3$ |
| $CH_3CH_2\overset{O}{\overset{\|}{C}}-$ | H | H | $-S\underset{CH_3}{\underset{\|}{C}}H-CO_2CH_3$ | $CH_3O$ | $CH_3$ |
| $(CH_3)_2CH-\overset{O}{\overset{\|}{C}}-$ | H | H | $-S\underset{CH_3}{\underset{\|}{C}}H-CO_2CH_3$ | $CH_3O$ | $CH_3$ |
| $n\text{-}C_{12}H_{25}\overset{O}{\overset{\|}{C}}-$ | H | H | $-S\underset{CH_3}{\underset{\|}{C}}H-CO_2CH_3$ | $CH_3O$ | $CH_3$ |
| $CH_2{=}CH-\overset{O}{\overset{\|}{C}}-$ | H | H | $-S\underset{CH_3}{\underset{\|}{C}}H-CO_2CH_3$ | $CH_3O$ | $CH_3$ |
| $CH_2{=}CHCH_2\overset{O}{\overset{\|}{C}}-$ | H | H | $-S\underset{CH_3}{\underset{\|}{C}}H-CO_2CH_3$ | $CH_3O$ | $CH_3$ |
| $CH_3(CH_2)_2CH{=}CH-\overset{O}{\overset{\|}{C}}-$ | H | H | $-S\underset{CH_3}{\underset{\|}{C}}H-CO_2CH_3$ | $CH_3O$ | $CH_3$ |
| $CH_3C{\equiv}C-CH_2\overset{O}{\overset{\|}{C}}-$ | H | H | $-S\underset{CH_3}{\underset{\|}{C}}H-CO_2CH_3$ | $CH_3O$ | $CH_3$ |
| $ClCH_2\overset{O}{\overset{\|}{C}}-$ | H | H | $-S\underset{CH_3}{\underset{\|}{C}}H-CO_2CH_3$ | $CH_3O$ | $CH_3$ |
| $BrCH_2CH_2\overset{O}{\overset{\|}{C}}-$ | H | H | $-S\underset{CH_3}{\underset{\|}{C}}H-CO_2CH_3$ | $CH_3O$ | $CH_3$ |
| $CF_3-\overset{O}{\overset{\|}{C}}-$ | H | H | $-S\underset{CH_3}{\underset{\|}{C}}H-CO_2CH_3$ | $CH_3O$ | $CH_3$ |
| $CH_3OCH_2\overset{O}{\overset{\|}{C}}-$ | H | H | $-S\underset{CH_3}{\underset{\|}{C}}H-CO_2CH_3$ | $CH_3O$ | $CH_3$ |
| $C_2H_5O\overset{O}{\overset{\|}{C}}CH_2\overset{O}{\overset{\|}{C}}$ | H | H | $-S\underset{CH_3}{\underset{\|}{C}}H-CO_2CH_3$ | $CH_3O$ | $CH_3$ |
| $CH_3O\overset{O}{\overset{\|}{C}}-\overset{O}{\overset{\|}{C}}-$ | H | H | $-S\underset{CH_3}{\underset{\|}{C}}H-CO_2CH_3$ | $CH_3O$ | $CH_3$ |
| $i\text{-}C_3H_7O\overset{O}{\overset{\|}{C}}(CH_2)_2\overset{O}{\overset{\|}{C}}-$ | H | H | $-S\underset{CH_3}{\underset{\|}{C}}H-CO_2CH_3$ | $CH_3O$ | $CH_3$ |

TABLE IX-continued

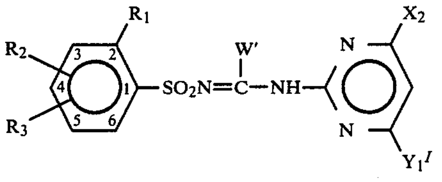

| $R_1$ | $R_2$ | $R_3$ | W' | $X_2$ | $Y_1^I$ |
|---|---|---|---|---|---|
| 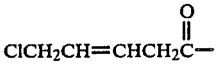 | H | H | $-SCH-CO_2CH_3$<br>$CH_3$ | $CH_3O$ | $CH_3$ |
| 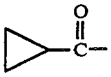 | H | H | $-SCH-CO_2CH_3$<br>$CH_3$ | $CH_3O$ | $CH_3$ |
| 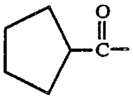 | H | H | $-SCH-CO_2CH_3$<br>$CH_3$ | $CH_3O$ | $CH_3$ |
| 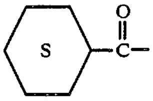 | H | H | $-SCH-CO_2CH_3$<br>$CH_3$ | $CH_3O$ | $CH_3$ |
| 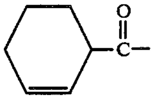 | H | H | $-SCH-CO_2CH_3$<br>$CH_3$ | $CH_3O$ | $CH_3$ |
| 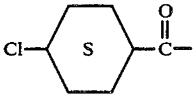 | H | H | $-SCH-CO_2CH_3$<br>$CH_3$ | $CH_3O$ | $CH_3$ |
| 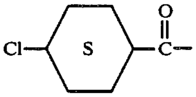 | H | H | $-SCH-CO_2CH_3$<br>$CH_3$ | $CH_3O$ | $CH_3$ |
| 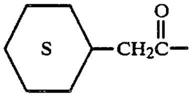 | H | H | $-SCH-CO_2CH_3$<br>$CH_3$ | $CH_3O$ | $CH_3$ |
| 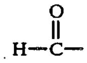 | H | H | $-SCH-CO_2CH_3$<br>$CH_3$ | $CH_3O$ | $CH_3$ |
| 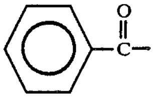 | H | H | $-SCH-CO_2CH_3$<br>$CH_3$ | $CH_3O$ | $CH_3$ |
| 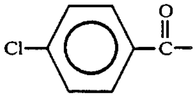 | H | H | $-SCH-CO_2CH_3$<br>$CH_3$ | $CH_3O$ | $CH_3$ |
| 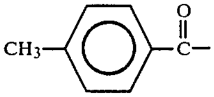 | H | H | $-SCH-CO_2CH_3$<br>$CH_3$ | $CH_3O$ | $CH_3$ |

TABLE IX-continued
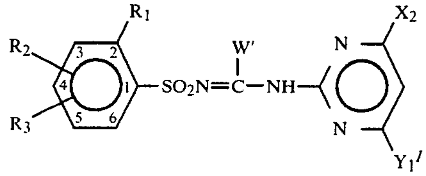
| $R_1$ | $R_2$ | $R_3$ | W′ | $X_2$ | $Y_1{}^I$ |
|---|---|---|---|---|---|
| 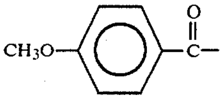 | H | H | 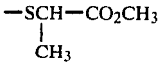 | $CH_3O$ | $CH_3$ |
| 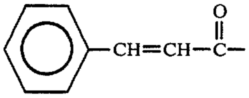 | H | H | 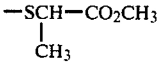 | $CH_3O$ | $CH_3$ |
| 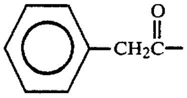 | H | H | 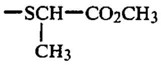 | $CH_3O$ | $CH_3$ |
| 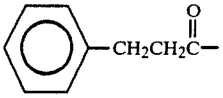 | H | H | 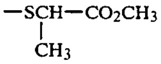 | $CH_3O$ | $CH_3$ |
| 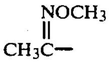 | H | H | 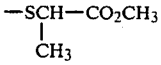 | $CH_3O$ | $CH_3$ |
| 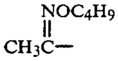 | H | H | 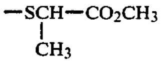 | $CH_3O$ | $CH_3$ |
| 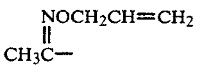 | H | H | 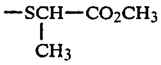 | $CH_3O$ | $CH_3$ |
| 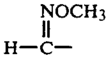 | H | H | 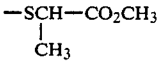 | $CH_3O$ | $CH_3$ |
| 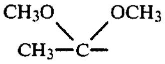 | H | H | 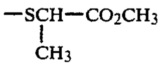 | $CH_3O$ | $CH_3$ |
| 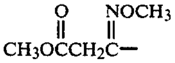 | H | H | 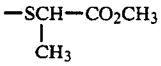 | $CH_3O$ | $CH_3$ |
| 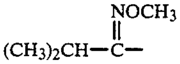 | H | H | 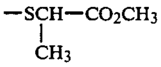 | $CH_3O$ | $CH_3$ |
| 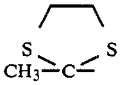 | H | H | 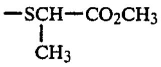 | $CH_3O$ | $CH_3$ |
| 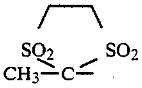 | H | H | 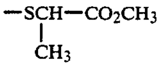 | $CH_3O$ | $CH_3$ |
| 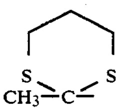 | H | H | 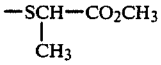 | $CH_3O$ | $CH_3$ |

TABLE IX-continued

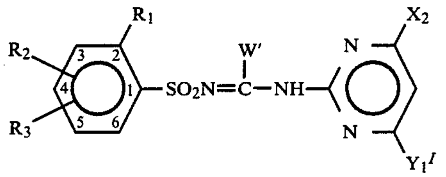

| $R_1$ | $R_2$ | $R_3$ | W' | $X_2$ | $Y_1^I$ |
|---|---|---|---|---|---|
| 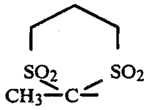 | H | H | $-SCH-CO_2CH_3$<br>\|<br>$CH_3$ | $CH_3O$ | $CH_3$ |
| NOH<br>‖<br>$CH_3C-$ | H | H | $-SCH-CO_2CH_3$<br>\|<br>$CH_3$ | $CH_3O$ | $CH_3$ |
| NOH<br>‖<br>$H-C-$ | H | H | $-SCH-CO_2CH_3$<br>\|<br>$CH_3$ | $CH_3O$ | $CH_3$ |
| 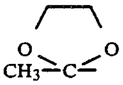 | H | H | $-SCH-CO_2CH_3$<br>\|<br>$CH_3$ | $CH_3O$ | $CH_3$ |

TABLE X

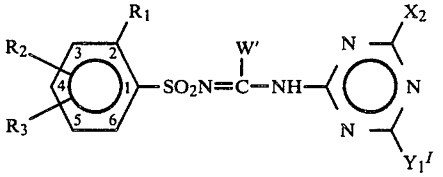

| $R_1$ | $R_2$ | $R_3$ | W' | $X_2$ | $Y_1^I$ |
|---|---|---|---|---|---|
| O<br>‖<br>$CH_3C-$ | H | H | $-OCH_3$ | $CH_3$ | $CH_3$ |
| O<br>‖<br>$CH_3C-$ | H | H | $-OCH_3$ | $CH_3O$ | $CH_3$ |
| O<br>‖<br>$CH_3C-$ | H | H | $-OCH_3$ | $CH_3O$ | $CH_3O$ |
| O<br>‖<br>$CH_3C-$ | H | H | $-SCH_3$ | $CH_3$ | $CH_3$ |
| O<br>‖<br>$CH_3C-$ | H | H | $-SCH_3$ | $CH_3O$ | $CH_3$ |
| O<br>‖<br>$CH_3C-$ | H | H | $-SCH_3$ | $CH_3O$ | $CH_3O$ |
| O<br>‖<br>$CH_3C-$ | H | H | $-SCH(CH_3)_2$ | $CH_3$ | $CH_3O$ |
| O<br>‖<br>$CH_3C-$ | H | H | $-SC_{12}H_{25}$ | $CH_3$ | $CH_3O$ |
| O<br>‖<br>$CH_3C-$ | H | H | $-SCH_2CH=CH_2$ | $CH_3$ | $CH_3O$ |

TABLE X-continued

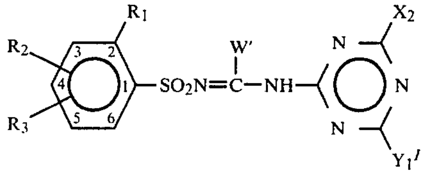

| $R_1$ | $R_2$ | $R_3$ | W' | $X_2$ | $Y_1{}^I$ |
|---|---|---|---|---|---|
| $CH_3\overset{O}{\overset{\|}{C}}-$ | H | H | $-SCH_2CH_2OCH_3$ | $CH_3$ | $CH_3O$ |
| $CH_3\overset{O}{\overset{\|}{C}}-$ | H | H | $-SCH_2CH_2OCH_2CH_3$ | $CH_3$ | $CH_3O$ |
| $CH_3\overset{O}{\overset{\|}{C}}-$ | H | H | $-S(CH_2)OCH_3$ | $CH_3$ | $CH_3O$ |
| $CH_3\overset{O}{\overset{\|}{C}}-$ | H | H | $-SCH_2-$ 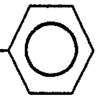 | $CH_3$ | $CH_3O$ |
| $CH_3\overset{O}{\overset{\|}{C}}-$ | H | H | $-SCH_2CO_2CH_3$ | $CH_3$ | $CH_3O$ |
| $CH_3\overset{O}{\overset{\|}{C}}-$ | H | H | $-S\underset{CH_3}{\underset{\|}{C}}HCO_2CH_3$ | $CH_3$ | $CH_3O$ |
| $CH_3\overset{O}{\overset{\|}{C}}-$ | H | H | $-SCH_2CO_2-$ 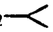 | $CH_3$ | $CH_3O$ |
| $CH_3\overset{O}{\overset{\|}{C}}-$ | H | H | $-S\underset{CH_3}{\underset{\|}{C}}HCO_2-n\text{-}C_4H_9$ | $CH_3$ | $CH_3O$ |
| $CH_3\overset{O}{\overset{\|}{C}}-$ | H | H | $-SCH_2\overset{O}{\overset{\|}{C}}NH_2$ | $CH_3$ | $CH_3O$ |
| $CH_3\overset{O}{\overset{\|}{C}}-$ | H | H | $-S\underset{CH_3}{\underset{\|}{C}}H_2\overset{O}{\overset{\|}{C}}NHCH_2CH_3$ | $CH_3$ | $CH_3O$ |
| $CH_3\overset{O}{\overset{\|}{C}}-$ | H | H | $-SCH_2\overset{O}{\overset{\|}{C}}N(C_4H_9)_2$ | $CH_3$ | $CH_3O$ |
| $CH_3\overset{O}{\overset{\|}{C}}-$ | H | H | $-S\underset{CH_3}{\underset{\|}{C}}H\overset{O}{\overset{\|}{C}}N(CH_3)_2$ | $CH_3$ | $CH_3O$ |
| $CH_3\overset{O}{\overset{\|}{C}}-$ | H | H | $-S\underset{CH_3}{\underset{\|}{C}}H-\overset{O}{\overset{\|}{C}}\underset{CH_3}{\underset{\|}{N}}-OCH_3$ | $CH_3$ | $CH_3O$ |
| $CH_3\overset{O}{\overset{\|}{C}}-$ | H | H | $-SCH_2CN$ | $CH_3$ | $CH_3O$ |
| $CH_3\overset{O}{\overset{\|}{C}}-$ | H | H | $-SCH_2CH{=}CH-CH_3$ | $CH_3$ | $CH_3O$ |
| $CH_3\overset{O}{\overset{\|}{C}}-$ | H | H | $-SCH_2C{\equiv}C-CH_3$ | $CH_3$ | $CH_3O$ |

TABLE X-continued
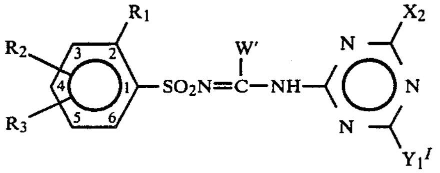
| $R_1$ | $R_2$ | $R_3$ | W' | $X_2$ | $Y_1{}^I$ |
|---|---|---|---|---|---|
| 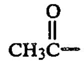 | H | H | 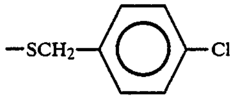 | $CH_3$ | $CH_3O$ |
| 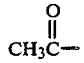 | H | H | 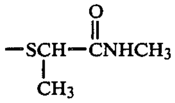 | $CH_3$ | $CH_3O$ |
| 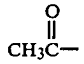 | H | H | 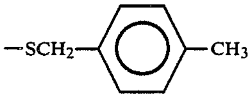 | $CH_3$ | $CH_3O$ |
| 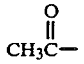 | H | H | 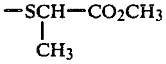 | $CH_3$ | $CH_3O$ |
| 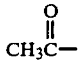 | 3-Cl | H | 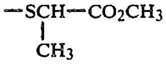 | $CH_3$ | $CH_3O$ |
| 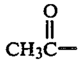 | 4-Cl | H | 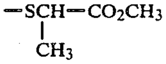 | $CH_3$ | $CH_3O$ |
| 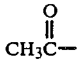 | 5-Cl | H | 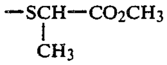 | $CH_3$ | $CH_3O$ |
| 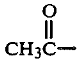 | 6-Cl | H | 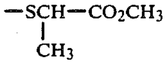 | $CH_3$ | $CH_3O$ |
| 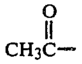 | 4-Cl | 5-Cl | 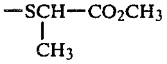 | $CH_3$ | $CH_3O$ |
| 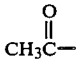 | 5-Cl | 6-$CH_3$ | 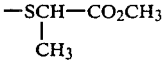 | $CH_3$ | $CH_3O$ |
| 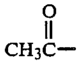 | 5-F | H | 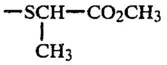 | $CH_3$ | $CH_3O$ |
| 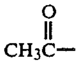 | 5-$CH_3$ | H | 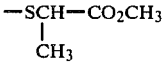 | $CH_3$ | $CH_3O$ |
| 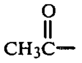 | 5-i-$C_3H_7$ | H | 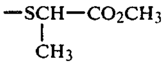 | $CH_3$ | $CH_3O$ |
| 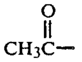 | 5-$NO_2$ | H | 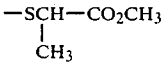 | $CH_3$ | $CH_3O$ |
| 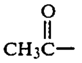 | 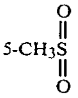 | H | 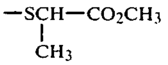 | $CH_3$ | $CH_3O$ |

TABLE X-continued
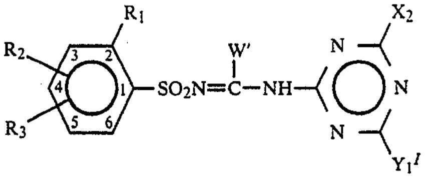
| $R_1$ | $R_2$ | $R_3$ | W' | $X_2$ | $Y_1{}^I$ |
|---|---|---|---|---|---|
| 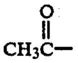 | 5-$CH_3S$ | H | 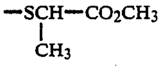 | $CH_3$ | $CH_3O$ |
| 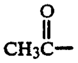 | 5-$CF_3$ | H | 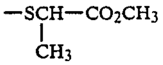 | $CH_3$ | $CH_3O$ |
| 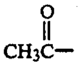 | 5-$(CH_3)_2N$— | H | 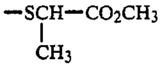 | $CH_3$ | $CH_3O$ |
| 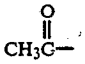 | 6-$NO_2$ | H | 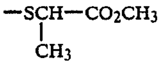 | $CH_3$ | $CH_3O$ |
| 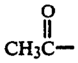 | 6-$CF_3$ | H | 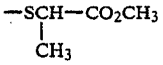 | $CH_3$ | $CH_3O$ |
| 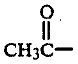 | 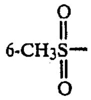 | H | 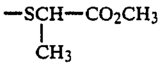 | $CH_3$ | $CH_3O$ |
| 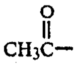 | H | H | 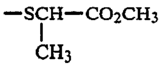 | $CH_3CH_2O$— | $CH_3O$ |
| 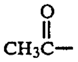 | H | H | 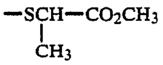 | $C_4H_9O$— | $CH_3O$ |
| 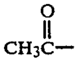 | H | H | 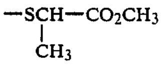 | $CH_3OCH_2O$— | $CH_3$ |
| 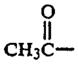 | H | H | 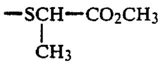 | $CH_3O(CH_2)_3O$— | $CH_3$ |
| 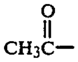 | H | H | 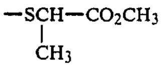 | 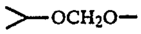 | $CH_3$ |
| 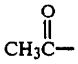 | H | H | 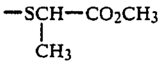 | 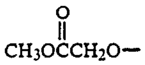 | $CH_3$ |
| 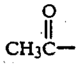 | H | H | 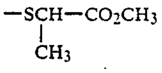 | 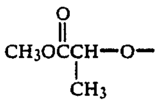 | $CH_3$ |
| 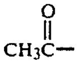 | H | H | 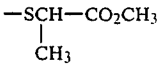 | 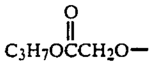 | $CH_3$ |
| 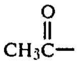 | H | H | 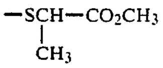 | $CF_3CH_2O$ | $CH_3$ |
| 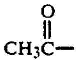 | H | H | 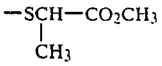 | $CCl_3CH_2O$— | $CH_3$ |

TABLE X-continued

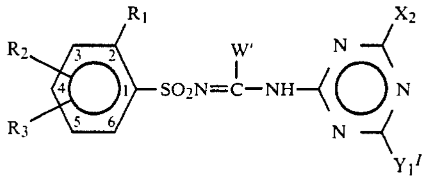

| $R_1$ | $R_2$ | $R_3$ | W' | $X_2$ | $Y_1{}^I$ |
|---|---|---|---|---|---|
| $CH_3\overset{O}{\overset{\|}{C}}-$ | H | H | $-\underset{CH_3}{\underset{\|}{SCH}}-CO_2CH_3$ | $CH_3O-$ | $CH_3$ |
| $CH_3CH_2\overset{O}{\overset{\|}{C}}-$ | H | H | $-\underset{CH_3}{\underset{\|}{SCH}}-CO_2CH_3$ | $CH_3O$ | $CH_3$ |
| $(CH_3)_2CH-\overset{O}{\overset{\|}{C}}-$ | H | H | $-\underset{CH_3}{\underset{\|}{SCH}}-CO_2CH_3$ | $CH_3O$ | $CH_3$ |
| $n\text{-}C_{12}H_{25}\overset{O}{\overset{\|}{C}}-$ | H | H | $-\underset{CH_3}{\underset{\|}{SCH}}-CO_2CH_3$ | $CH_3O$ | $CH_3$ |
| $CH_2{=}CH-\overset{O}{\overset{\|}{C}}-$ | H | H | $-\underset{CH_3}{\underset{\|}{SCH}}-CO_2CH_3$ | $CH_3O$ | $CH_3$ |
| $CH_2{=}CHCH_2\overset{O}{\overset{\|}{C}}-$ | H | H | $-\underset{CH_3}{\underset{\|}{SCH}}-CO_2CH_3$ | $CH_3O$ | $CH_3$ |
| $CH_3(CH_2)_2CH{=}CH-\overset{O}{\overset{\|}{C}}-$ | H | H | $-\underset{CH_3}{\underset{\|}{SCH}}-CO_2CH_3$ | $CH_3O$ | $CH_3$ |
| $CH_3C{\equiv}C-CH_2\overset{O}{\overset{\|}{C}}-$ | H | H | $-\underset{CH_3}{\underset{\|}{SCH}}-CO_2CH_3$ | $CH_3O$ | $CH_3$ |
| $ClCH_2\overset{O}{\overset{\|}{C}}-$ | H | H | $-\underset{CH_3}{\underset{\|}{SCH}}-CO_2CH_3$ | $CH_3O$ | $CH_3$ |
| $BrCH_2CH_2\overset{O}{\overset{\|}{C}}-$ | H | H | $-\underset{CH_3}{\underset{\|}{SCH}}-CO_2CH_3$ | $CH_3O$ | $CH_3$ |
| $CF_3-\overset{O}{\overset{\|}{C}}-$ | H | H | $-\underset{CH_3}{\underset{\|}{SCH}}-CO_2CH_3$ | $CH_3O$ | $CH_3$ |
| $CH_3OCH_2\overset{O}{\overset{\|}{C}}-$ | H | H | $-\underset{CH_3}{\underset{\|}{SCH}}-CO_2CH_3$ | $CH_3O$ | $CH_3$ |
| $C_2H_5O\overset{O}{\overset{\|}{C}}CH_2\overset{O}{\overset{\|}{C}}$ | H | H | $-\underset{CH_3}{\underset{\|}{SCH}}-CO_2CH_3$ | $CH_3O$ | $CH_3$ |
| $CH_3O\overset{O}{\overset{\|}{C}}-\overset{O}{\overset{\|}{C}}-$ | H | H | $-\underset{CH_3}{\underset{\|}{SCH}}-CO_2CH_3$ | $CH_3O$ | $CH_3$ |
| $i\text{-}C_3H_7O\overset{O}{\overset{\|}{C}}(CH_2)_2\overset{O}{\overset{\|}{C}}-$ | H | H | $-\underset{CH_3}{\underset{\|}{SCH}}-CO_2CH_3$ | $CH_3O$ | $CH_3$ |
| $ClCH_2CH{=}CHCH_2\overset{O}{\overset{\|}{C}}-$ | H | H | $-\underset{CH_3}{\underset{\|}{SCH}}-CO_2CH_3$ | $CH_3O$ | $CH_3$ |
| 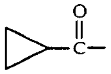 | H | H | $-\underset{CH_3}{\underset{\|}{SCH}}-CO_2CH_3$ | $CH_3O$ | $CH_3$ |

TABLE X-continued

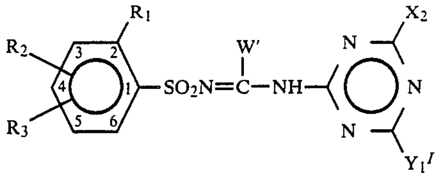

| $R_1$ | $R_2$ | $R_3$ | W' | $X_2$ | $Y_1{}^I$ |
|---|---|---|---|---|---|
| 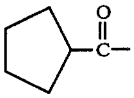 | H | H | $-\underset{\mid\;CH_3}{SCH}-CO_2CH_3$ | $CH_3O$ | $CH_3$ |
| 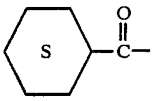 | H | H | $-\underset{\mid\;CH_3}{SCH}-CO_2CH_3$ | $CH_3O$ | $CH_3$ |
| 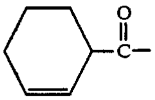 | H | H | $-\underset{\mid\;CH_3}{SCH}-CO_2CH_3$ | $CH_3O$ | $CH_3$ |
| 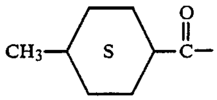 | H | H | $-\underset{\mid\;CH_3}{SCH}-CO_2CH_3$ | $CH_3O$ | $CH_3$ |
| 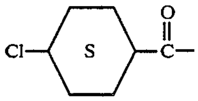 | H | H | $-\underset{\mid\;CH_3}{SCH}-CO_2CH_3$ | $CH_3O$ | $CH_3$ |
| 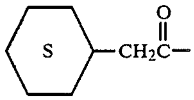 | H | H | $-\underset{\mid\;CH_3}{SCH}-CO_2CH_3$ | $CH_3O$ | $CH_3$ |
| 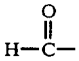 | H | H | $-\underset{\mid\;CH_3}{SCH}-CO_2CH_3$ | $CH_3O$ | $CH_3$ |
| 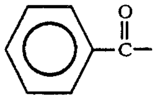 | H | H | $-\underset{\mid\;CH_3}{SCH}-CO_2CH_3$ | $CH_3O$ | $CH_3$ |
| 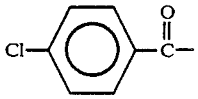 | H | H | $-\underset{\mid\;CH_3}{SCH}-CO_2CH_3$ | $CH_3O$ | $CH_3$ |
| 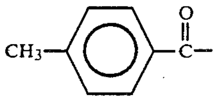 | H | H | $-\underset{\mid\;CH_3}{SCH}-CO_2CH_3$ | $CH_3O$ | $CH_3$ |
| 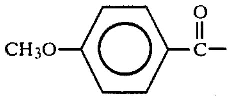 | H | H | $-\underset{\mid\;CH_3}{SCH}-CO_2CH_3$ | $CH_3O$ | $CH_3$ |
| 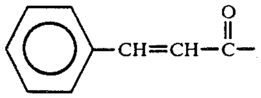 | H | H | $-\underset{\mid\;CH_3}{SCH}-CO_2CH_3$ | $CH_3O$ | $CH_3$ |

TABLE X-continued

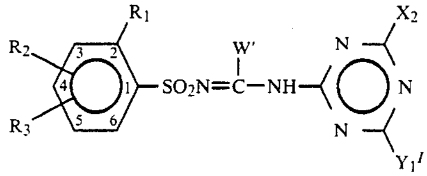

| $R_1$ | $R_2$ | $R_3$ | W' | $X_2$ | $Y_1{}^I$ |
|---|---|---|---|---|---|
| 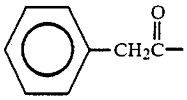 | H | H | $—SCH—CO_2CH_3$<br>\|<br>$CH_3$ | $CH_3O$ | $CH_3$ |
| 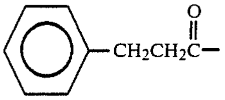 | H | H | $—SCH—CO_2CH_3$<br>\|<br>$CH_3$ | $CH_3O$ | $CH_3$ |
| $NOCH_3$<br>‖<br>$CH_3C—$ | H | H | $—SCH—CO_2CH_3$<br>\|<br>$CH_3$ | $CH_3O$ | $CH_3$ |
| $NOC_4H_9$<br>‖<br>$CH_3C—$ | H | H | $—SCH—CO_2CH_3$<br>\|<br>$CH_3$ | $CH_3O$ | $CH_3$ |
| $NOCH_2CH=CH_2$<br>‖<br>$CH_3C—$ | H | H | $—SCH—CO_2CH_3$<br>\|<br>$CH_3$ | $CH_3O$ | $CH_3$ |
| $NOCH_3$<br>‖<br>$H—C—$ | H | H | $—SCH—CO_2CH_3$<br>\|<br>$CH_3$ | $CH_3O$ | $CH_3$ |
| $CH_3O$ $OCH_3$<br>╲ ╱<br>$CH_3—C—$ | H | H | $—SCH—CO_2CH_3$<br>\|<br>$CH_3$ | $CH_3O$ | $CH_3$ |
| O $NOCH_3$<br>‖ ‖<br>$CH_3OCCH_2C—$ | H | H | $—SCH—CO_2CH_3$<br>\|<br>$CH_3$ | $CH_3O$ | $CH_3$ |
| $NOCH_3$<br>‖<br>$(CH_3)_2CH—C—$ | H | H | $—SCH—CO_2CH_3$<br>\|<br>$CH_3$ | $CH_3O$ | $CH_3$ |
| 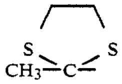 | H | H | $—SCH—CO_2CH_3$<br>\|<br>$CH_3$ | $CH_3O$ | $CH_3$ |
| 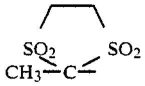 | H | H | $—SCH—CO_2CH_3$<br>\|<br>$CH_3$ | $CH_3O$ | $CH_3$ |
| 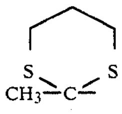 | H | H | $—SCH—CO_2CH_3$<br>\|<br>$CH_3$ | $CH_3O$ | $CH_3$ |
| 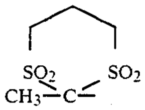 | H | H | $—SCH—CO_2CH_3$<br>\|<br>$CH_3$ | $CH_3O$ | $CH_3$ |
| $NOH$<br>‖<br>$CH_3C—$ | H | H | $—SCH—CO_2CH_3$<br>\|<br>$CH_3$ | $CH_3O$ | $CH_3$ |

TABLE X-continued

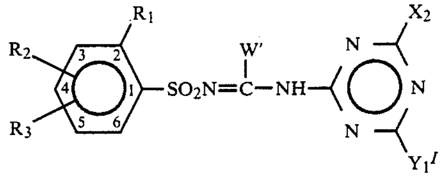

| $R_1$ | $R_2$ | $R_3$ | W' | $X_2$ | $Y_1{}^I$ |
|---|---|---|---|---|---|
| $H-\overset{NOH}{\overset{\|}{C}}-$ | H | H | $-S\underset{CH_3}{\underset{\|}{C}}H-CO_2CH_3$ | $CH_3O$ | $CH_3$ |
| 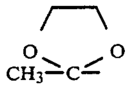 | H | H | $-S\underset{CH_3}{\underset{\|}{C}}H-CO_2CH_3$ | $CH_3O$ | $CH_3$ |

TABLE XI

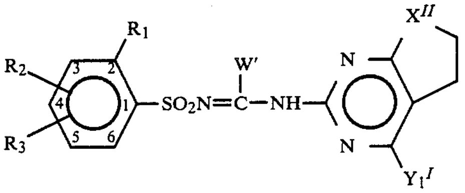

| $R_1$ | $R_2$ | $R_3$ | W' | $X_{II}$ | $Y_1{}^I$ |
|---|---|---|---|---|---|
| $CH_3CH_2\overset{O}{\overset{\|}{C}}-$ | H | H | $-S\underset{CH_3}{\underset{\|}{C}}H-CO_2CH_3$ | —O— | $CH_3$ |
| $(CH_3)_2CH-\overset{O}{\overset{\|}{C}}-$ | H | H | $-S\underset{CH_3}{\underset{\|}{C}}H-CO_2CH_3$ | —O— | $CH_3$ |
| $n\text{-}C_{12}H_{25}\overset{O}{\overset{\|}{C}}-$ | H | H | $-S\underset{CH_3}{\underset{\|}{C}}H-CO_2CH_3$ | —O— | $CH_3$ |
| $CH_2=CH-\overset{O}{\overset{\|}{C}}-$ | H | H | $-S\underset{CH_3}{\underset{\|}{C}}H-CO_2CH_3$ | —O— | $CH_3$ |
| $CH_2=CHCH_2\overset{O}{\overset{\|}{C}}-$ | H | H | $-S\underset{CH_3}{\underset{\|}{C}}H-CO_2CH_3$ | —O— | $CH_3$ |
| $CH_3(CH_2)_2CH=CH-\overset{O}{\overset{\|}{C}}-$ | H | H | $-S\underset{CH_3}{\underset{\|}{C}}H-CO_2CH_3$ | —O— | $CH_3$ |
| $CH_3C\equiv CH_2\overset{O}{\overset{\|}{C}}-$ | H | H | $-S\underset{CH_3}{\underset{\|}{C}}H-CO_2CH_3$ | —O— | $CH_3$ |
| $ClCH_2\overset{O}{\overset{\|}{C}}-$ | H | H | $-S\underset{CH_3}{\underset{\|}{C}}H-CO_2CH_3$ | —O— | $CH_3$ |
| $BrCH_2CH_2\overset{O}{\overset{\|}{C}}-$ | H | H | $-S\underset{CH_3}{\underset{\|}{C}}H-CO_2CH_3$ | —O— | $CH_3$ |
| $CF_3-\overset{O}{\overset{\|}{C}}-$ | H | H | $-S\underset{CH_3}{\underset{\|}{C}}H-CO_2CH_3$ | —O— | $CH_3$ |
| $CH_3OCH_2\overset{O}{\overset{\|}{C}}-$ | H | H | $-S\underset{CH_3}{\underset{\|}{C}}H-CO_2CH_3$ | —O— | $CH_3$ |

TABLE XI-continued

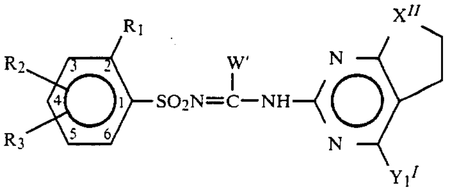

| $R_1$ | $R_2$ | $R_3$ | W' | $X_{II}$ | $Y_1{}^I$ |
|---|---|---|---|---|---|
| $CH_3\overset{O}{\overset{\|}{C}}-$ | H | H | $-S\underset{CH_3}{CH}\overset{O}{\overset{\|}{C}}N(CH_3)_2$ | —O— | $CH_3O$ |
| $CH_3\overset{O}{\overset{\|}{C}}-$ | H | H | $-S\underset{CH_3}{CH}-\overset{O}{\overset{\|}{C}}\underset{CH_3}{N}-OCH_3$ | —O— | $CH_3O$ |
| $CH_3\overset{O}{\overset{\|}{C}}-$ | H | H | $-SCH_2CN$ | —O— | $CH_3O$ |
| $CH_3\overset{O}{\overset{\|}{C}}-$ | H | H | $-SCH_2CH{=}CH-CH_3$ | —O— | $CH_3O$ |
| $CH_3\overset{O}{\overset{\|}{C}}-$ | H | H | $-SCH_2C{\equiv}C-CH_3$ | —O— | $CH_3O$ |
| $CH_3\overset{O}{\overset{\|}{C}}-$ | H | H | 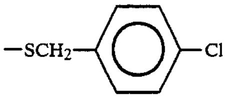 | —O— | $CH_3O$ |
| $CH_3\overset{O}{\overset{\|}{C}}-$ | H | H | 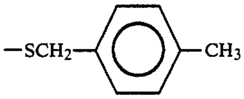 | —O— | $CH_3O$ |
| $CH_3\overset{O}{\overset{\|}{C}}-$ | H | H | $-S\underset{CH_3}{CH}-CO_2CH_3$ | —O— | $CH_3O$ |
| $CH_3\overset{O}{\overset{\|}{C}}-$ | 3-Cl | H | $-S\underset{CH_3}{CH}-CO_2CH_3$ | —O— | $CH_3O$ |
| $CH_3\overset{O}{\overset{\|}{C}}-$ | 4-Cl | H | $-S\underset{CH_3}{CH}-CO_2CH_3$ | —O— | $CH_3O$ |
| $CH_3\overset{O}{\overset{\|}{C}}-$ | 5-Cl | H | $-S\underset{CH_3}{CH}-CO_2CH_3$ | —O— | $CH_3O$ |
| $CH_3\overset{O}{\overset{\|}{C}}-$ | 6-Cl | H | $-S\underset{CH_3}{CH}-CO_2CH_3$ | —O— | $CH_3O$ |
| $CH_3\overset{O}{\overset{\|}{C}}-$ | 4-Cl | 5-Cl | $-S\underset{CH_3}{CH}-CO_2CH_3$ | —O— | $CH_3O$ |
| $CH_3\overset{O}{\overset{\|}{C}}-$ | 5-Cl | 6-$CH_3$ | $-S\underset{CH_3}{CH}-CO_2CH_3$ | —O— | $CH_3O$ |
| $CH_3\overset{O}{\overset{\|}{C}}-$ | 5-F | H | $-S\underset{CH_3}{CH}-CO_2CH_3$ | —O— | $CH_3O$ |

TABLE XI-continued

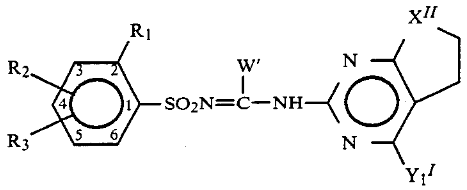

| $R_1$ | $R_2$ | $R_3$ | W' | $X_{II}$ | $Y_1^I$ |
|---|---|---|---|---|---|
| O<br>‖<br>$CH_3C-$ | 5-$CH_3$ | H | $-SCH-CO_2CH_3$<br>\|<br>$CH_3$ | —O— | $CH_3O$ |
| O<br>‖<br>$CH_3C-$ | 5-i-$C_3H_7$ | H | $-SCH-CO_2CH_3$<br>\|<br>$CH_3$ | —O— | $CH_3O$ |
| O<br>‖<br>$CH_3C-$ | 5-$NO_2$ | H | $-SCH-CO_2CH_3$<br>\|<br>$CH_3$ | —O— | $CH_3O$ |
| O<br>‖<br>$CH_3C-$ | O<br>‖<br>5-$CH_3S$<br>‖<br>O | H | $-SCH-CO_2CH_3$<br>\|<br>$CH_3$ | —O— | $CH_3O$ |
| O<br>‖<br>$CH_3C-$ | 5-$CH_3S$ | H | $-SCH-CO_2CH_3$<br>\|<br>$CH_3$ | —O— | $CH_3O$ |
| O<br>‖<br>$CH_3C-$ | 5-$CF_3$ | H | $-SCH-CO_2CH_3$<br>\|<br>$CH_3$ | —O— | $CH_3O$ |
| O<br>‖<br>$CH_3C-$ | 5-$(CH_3)_2N-$ | H | $-SCH-CO_2CH_3$<br>\|<br>$CH_3$ | —O— | $CH_3O$ |
| O<br>‖<br>$CH_3C-$ | 6-$NO_2$ | H | $-SCH-CO_2CH_3$<br>\|<br>$CH_3$ | —O— | $CH_3O$ |
| O<br>‖<br>$CH_3C-$ | 6-$CF_3$ | H | $-SCH-CO_2CH_3$<br>\|<br>$CH_3$ | —O— | $CH_3O$ |
| O<br>‖<br>$CH_3C-$ | O<br>‖<br>6-$CH_3S$<br>‖<br>O | H | $-SCH-CO_2CH_3$<br>\|<br>$CH_3$ | —O— | $CH_3O$ |
| O<br>‖<br>$CH_3C-$ | H | H | $-OCH_3$ | —O— | $CH_3O$ |
| O<br>‖<br>$CH_3C-$ | H | H | $-OCH_3$ | —O— | $CH_3$ |
| O<br>‖<br>$CH_3C-$ | H | H | $-OCH_3$ | $-CH_2-$ | $CH_3O$ |
| O<br>‖<br>$CH_3C-$ | H | H | $-SCH_3$ | —O— | $CH_3O$ |
| O<br>‖<br>$CH_3C-$ | H | H | $-SCH_3$ | —O— | $CH_3$ |
| O<br>‖<br>$CH_3C-$ | H | H | $-SCH_3$ | $-CH_2-$ | $CH_3O$ |
| O<br>‖<br>$CH_3C-$ | H | H | $-SCH(CH_3)_2$ | —O— | $CH_3$ |

TABLE XI-continued

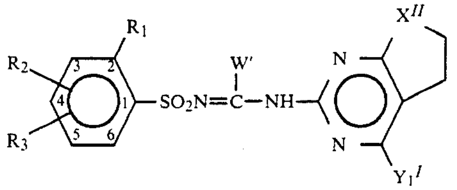

| $R_1$ | $R_2$ | $R_3$ | W' | $X_{II}$ | $Y_1{}^I$ |
|---|---|---|---|---|---|
| $CH_3\overset{\overset{O}{\|}}{C}-$ | H | H | $-SC_{12}H_{25}$ | —O— | $CH_3$ |
| $CH_3\overset{\overset{O}{\|}}{C}-$ | H | H | $-SCH_2CH{=}CH_2$ | —O— | $CH_3$ |
| $CH_3\overset{\overset{O}{\|}}{C}-$ | H | H | $-SCH_2CH_2OCH_3$ | —O— | $CH_3$ |
| $CH_3\overset{\overset{O}{\|}}{C}-$ | H | H | $-SCH_2CH_2OCH_2CH_3$ | —O— | $CH_3$ |
| $CH_3\overset{\overset{O}{\|}}{C}-$ | H | H | $-S(CH_2)_3OCH_3$ | —O— | $CH_3$ |
| $CH_3\overset{\overset{O}{\|}}{C}-$ | H | H | 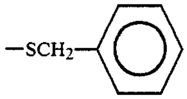 | —O— | $CH_3$ |
| $CH_3\overset{\overset{O}{\|}}{C}-$ | H | H | $-SCH_2CO_2CH_3$ | —O— | $CH_3$ |
| $CH_3\overset{\overset{O}{\|}}{C}-$ | H | H | $-\underset{\underset{CH_3}{\vert}}{S}CHCO_2CH_3$ | —O— | $CH_3$ |
| $CH_3\overset{\overset{O}{\|}}{C}-$ | H | H | 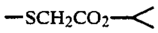 | —O— | $CH_3$ |
| $CH_3\overset{\overset{O}{\|}}{C}-$ | H | H | $-\underset{\underset{CH_3}{\vert}}{S}CHCO_2-n\text{-}C_4H_9$ | —O— | $CH_3$ |
| $CH_3\overset{\overset{O}{\|}}{C}-$ | H | H | $-SCH_2\overset{\overset{O}{\|}}{\underset{\underset{O}{\|}}{C}}NH_2$ | —O— | $CH_3$ |
| $CH_3\overset{\overset{O}{\|}}{C}-$ | H | H | $-SCH_2\overset{\overset{O}{\|}}{C}NHCH_2CH_3$ | —O— | $CH_3$ |
| $CH_3\overset{\overset{O}{\|}}{C}-$ | H | H | $-\underset{\underset{CH_3}{\vert}}{S}CH-\overset{\overset{O}{\|}}{C}NHCH_3$ | —O— | $CH_3$ |
| $CH_3\overset{\overset{O}{\|}}{C}-$ | H | H | $-SCH_2\overset{\overset{O}{\|}}{C}N(C_4H_9)_2$ | —O— | $CH_3$ |
| $C_2H_5O\overset{\overset{O}{\|}}{C}CH_2\overset{\overset{O}{\|}}{C}$ | H | H | $-\underset{\underset{CH_3}{\vert}}{S}CH-CO_2CH_3$ | —O— | $CH_3$ |
| $CH_3O\overset{\overset{O}{\|}}{C}-\overset{\overset{O}{\|}}{C}-$ | H | H | $-\underset{\underset{CH_3}{\vert}}{S}CH-CO_2CH_3$ | —O— | $CH_3$ |

TABLE XI-continued

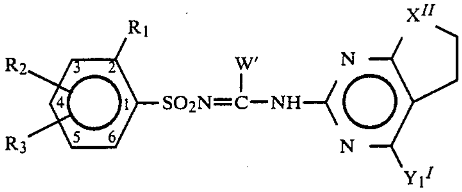

| $R_1$ | $R_2$ | $R_3$ | W' | $X_{II}$ | $Y_1{}^I$ |
|---|---|---|---|---|---|
| $i\text{-}C_3H_7OC(=O)(CH_2)_2C(=O)-$ | H | H | $-SCH(CH_3)-CO_2CH_3$ | —O— | $CH_3$ |
| $ClCH_2CH=CHCH_2C(=O)-$ | H | H | $-SCH(CH_3)-CO_2CH_3$ | —O—O | $CH_3$ |
| 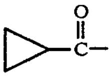 | H | H | $-SCH(CH_3)-CO_2CH_3$ | —O— | $CH_3$ |
| 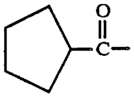 | H | H | $-SCH(CH_3)-CO_2CH_3$ | —O— | $CH_3$ |
| 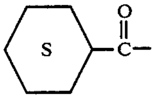 | H | H | $-SCH(CH_3)-CO_2CH_3$ | —O— | $CH_3$ |
| 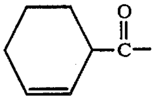 | H | H | $-SCH(CH_3)-CO_2CH_3$ | —O— | $CH_3$ |
| 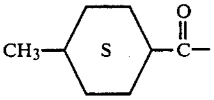 | H | H | $-SCH(CH_3)-CO_2CH_3$ | —O— | $CH_3$ |
| 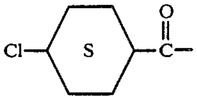 | H | H | $-SCH(CH_3)-CO_2CH_3$ | —O— | $CH_3$ |
| 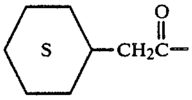 | H | H | $-SCH(CH_3)-CO_2CH_3$ | —O— | $CH_3$ |
| $H-C(=O)-$ | H | H | $-SCH(CH_3)-CO_2CH_3$ | —O— | $CH_3$ |
| 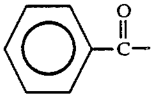 | H | H | $-SCH(CH_3)-CO_2CH_3$ | —O— | $CH_3$ |
| 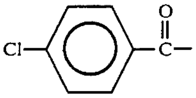 | H | H | $-SCH(CH_3)-CO_2CH_3$ | —O— | $CH_3$ |
| 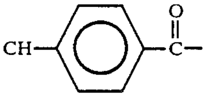 | H | H | $-SCH(CH_3)-CO_2CH_3$ | —O— | $CH_3$ |

TABLE XI-continued

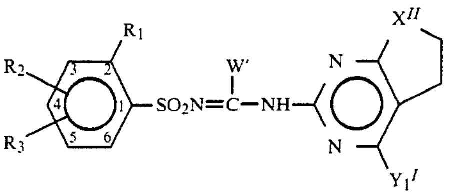

| $R_1$ | $R_2$ | $R_3$ | W' | $X_{II}$ | $Y_1{}^I$ |
|---|---|---|---|---|---|
| 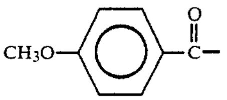 | H | H | $-SCH(CH_3)-CO_2CH_3$ | —O— | $CH_3$ |
| 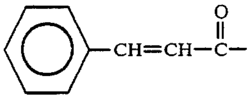 | H | H | $-SCH(CH_3)-CO_2CH_3$ | —O— | $CH_3$ |
| 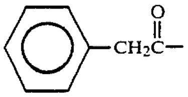 | H | H | $-SCH(CH_3)-CO_2CH_3$ | —O— | $CH_3$ |
| 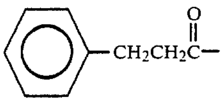 | H | H | $-SCH(CH_3)-CO_2CH_3$ | —O— | $CH_3$ |
| $CH_3C(=NOCH_3)-$ | H | H | $-SCH(CH_3)-CO_2CH_3$ | —O— | $CH_3$ |
| $CH_3C(=NOC_4H_9)-$ | H | H | $-SCH(CH_3)-CO_2CH_3$ | —O— | $CH_3$ |
| $CH_3C(=NOCH_2CH=CH_2)-$ | H | H | $-SCH(CH_3)-CO_2CH_3$ | —O— | $CH_3$ |
| $H-C(=NOCH_3)-$ | H | H | $-SCH(CH_3)-CO_2CH_3$ | —O— | $CH_3$ |
| 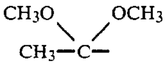 | H | H | $-SCH(CH_3)-CO_2CH_3$ | —O— | $CH_3$ |
| $CH_3OC(=O)CH_2C(=NOCH_3)-$ | H | H | $-SCH(CH_3)-CO_2CH_3$ | —O— | $CH_3$ |
| $(CH_3)_2CH-C(=NOCH_3)-$ | H | H | $-SCH(CH_3)-CO_2CH_3$ | —O— | $CH_3$ |
| 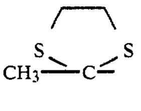 | H | H | $-SCH(CH_3)-CO_2CH_3$ | —O— | $CH_3$ |
| 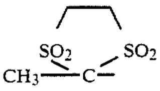 | H | H | $-SCH(CH_3)-CO_2CH_3$ | —O— | $CH_3$ |
| 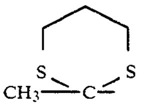 | H | H | $-SCH(CH_3)-CO_2CH_3$ | —O— | $CH_3$ |

TABLE XI-continued

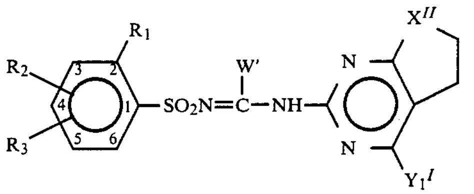

| $R_1$ | $R_2$ | $R_3$ | W' | $X_{II}$ | $Y_1^I$ |
|---|---|---|---|---|---|
| 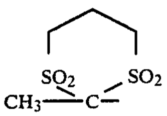 | H | H | 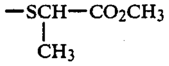 | —O— | $CH_3$ |
| 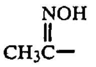 | H | H | 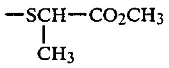 | —O— | $CH_3$ |
| 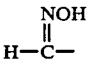 | H | H | 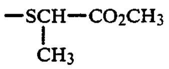 | —O— | $CH_3$ |
| 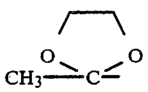 | H | H | 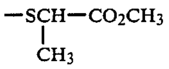 | —O— | $CH_3$ |

Formulations

Useful formulations of the compounds of Formula I can be prepared in conventional ways. They include dusts, granules, pellets, suspensions, emulsions, wettable powders, emulsifiable concentrates and the like. Many of them can be applied directly. Sprayable formulations can be extended in suitable media and used at spray volumes of from a few liters to several hundred liters per hectare. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the approximate proportions set forth in Table XII.

TABLE XII

| | Weight Percent* | | |
|---|---|---|---|
| | Active Ingredient | Diluent(s) | Surfactant(s) |
| Wettable Powders | 20-90 | 0-74 | 1-10 |
| Oil Suspensions, Solutions, Emulsions (including Emulsifiable Concentrates | 3-50 | 40-95 | 0-15 |
| Aqueous Suspensions | 10-50 | 40-84 | 1-20 |
| Dusts | 1-25 | 70-99 | 0-5 |
| Granules and Pellets | 0.1-95 | 5-99.9 | 0-15 |

*Active Ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation, or by tank mixing.

Some typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide", 2nd Ed., Interscience, New York, 1950. Solubility under 0.1% is preferred for suspension concentrates, solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending, and usually, grinding as in a hammer or fluid energy mill. Suspensions are prepared by wet milling (see, for example, Littler, U.S. Pat. No. 3,060,084). Granules and pellets may be made by spraying the active material on preformed granular carriers or by agglomeration techniques. See J. E. Browning, "Agglomeration", *Chemical Engineering,* Dec. 4, 1967, pp. 147ff and "Perry's Chemical Engineer's Handbook", 4th Ed., McGraw-Hill, New York, 1963, pp. 8-59ff.

For further information regarding the art of formulation, see for example:

H. M. Loux, U.S. Pat. No. 3,235,361, Col. 6, line 16 through Col. 7, line 19 and Examples 10 through 41.

R. W. Luckenbaugh, U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182.

H. Gysin and E. Knusli, U.S. Pat. No. 2,891,855, Col. 3, line 66 through Col. 5, line 17 and Examples 1-4.

G. C. Klingman, "Weed Control as a Science", John Wiley and Sons, Inc., New York, 1961, pp. 81-96.

J. D. Fryer and S. A. Evans, "Weed Control Handbook", 5th Ed., Blackwell Scientific Publications, Oxford, 1968, pp. 101-103.

Unless indicated otherwise, all parts are by weight in the following examples.

EXAMPLE 8

| Wettable Powder | |
|---|---|
| 2-Acetyl-N—[(4,6-dimethoxypyrimidin-2-yl)aminocarbonyl]benzenesulfonamide | 95% |
| dioctyl sodium sulfosuccinate | 0.1% |
| sodium ligninsulfonate | 1% |
| synthetic fine silica | 3.9% |

The ingredients are blended and ground in a hammermill to produce particles almost all of which are below 100 microns in size. That material is sifted through a U.S.S No. 50 screen and packaged.

EXAMPLE 9

| Wettable Powder | |
|---|---|
| 2-Acetyl-N—[(4-methoxy-6-methyl-1,3,5-triazin-2-yl)-aminocarbonyl]benzenesulfonamide | 50% |
| sodium alkylnaphthalenesulfonate | 2% |
| low viscosity methyl cellulose | 2% |
| diatomaceous earth | 46% |

The ingredients are blended, coarsely hammermilled and then air milled to produce particles of active essentially all below 10 microns in diameter. The product is reblended before packaging.

EXAMPLE 10

| Granule | |
|---|---|
| wettable powder of Example 8 | 10% |
| attapulgite granules (U.S.S. #20-40; 0.84-0.42 mm) | 90% |

A slurry of wettable powder containing 50% solids is sprayed onto the surface of attapulgite granules in a double-cone blender. The granules are dried and packaged.

EXAMPLE 11

| Wettable Powder | |
|---|---|
| 2-Acetyl-N—[(4,6-dimethoxypyrimidin-2-yl)-aminocarbonyl]bensenesulfonamide | 40% |
| dioctyl sodium sulfosuccinate | 1.5% |
| sodium ligninsulfonate | 3% |
| low viscosity methyl cellulose | 1.5% |
| attapulgite | 54% |

The ingredients are thoroughly blended and passed through an air mill to produce an average particle size under 15 microns, reblended, and sifted through a U.S.S. No. 50 sieve (0.3 mm opening) before packaging.

EXAMPLE 12

| Granule | |
|---|---|
| wettable powder of Example 8 | 25% |
| gypsum | 64% |

-continued

| Granule | |
|---|---|
| potassium sulfate | 11% |

The ingredients are blended in a rotating mixer, and water is sprayed onto that blend so as to effect granulation. When most of the granules have reached 1.0 to 0.42 mm (U.S.S. #18 to 40 sieves) in size, they are removed, dried and screened. Oversize material is crushed to produce additional material in the desired range. The resulting granules contain 10% of the active ingredient.

EXAMPLE 13

| Wettable Powder | |
|---|---|
| 2-Acetyl-N—[(4-methoxy-6-methyl-1,3,5-triazin-2-yl)-aminocarbonyl]benzenesulfonamide | 65% |
| dodecylphenol polyethylene glycol ether | 2% |
| sodium ligninsulfonate | 4% |
| sodium silicoaluminate | 6% |
| montmorillonite (calcined) | 23% |

The ingredients are thoroughly blended. The liquid surfactant is added by spraying on the solid ingredients in a blender. After grinding in a hammer mill to produce particles almost all of which are below 100 microns in size, the material is reblended, sifted through a U.S.S. #50 sieve (0.3 mm opening) and packaged.

EXAMPLE 14

| Oil Suspension | |
|---|---|
| 2-Acetyl-N—[(4,6-dimethoxypyrimidin-2-yl)-aminocarbonyl]benzenesulfonamide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting suspension may be applied directly, but preferably after being extended further with oils or emulsified in water.

EXAMPLE 15

| Aqueous Suspension | |
|---|---|
| 2-Acetyl-N—[(4-methoxy-6-methyl-1,3,5-triazin-2-yl)-aminocarbonyl]benzenesulfonamide | 25% |
| hydrated attapulgite | 3% |
| crude calcium ligninsulfonate | 10% |
| sodium dihydrogen phosphate | 0.5% |
| water | 61.5% |

The ingredients are ground together in a ball or roller mill until the solid particles have been reduced to sizes under 10 microns, and then packaged.

EXAMPLE 16

| Extruded Pellet | |
|---|---|
| 2-Acetyl-N—[(4,6-dimethoxypyrimidin-2-yl)aminocarbonyl]benzenesulfonamide | 25% |
| anhydrous sodium sulfate | 10% |

-continued

| Extruded Pellet | |
|---|---|
| crude calcium ligninsulfonate | 5% |
| sodium alkylnaphthalene-sulfonate | 1% |
| calcium/magnesium bentonite | 59% |

The ingredients are blended, hammer milled and then moistened with about 12% water. The mixture is extruded in the form of cylinders about 3 mm in diameter which are cut to produce pellets about 3 mm long. The pellets may be used directly, after drying, or dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 17

| Solution | |
|---|---|
| 2-Acetyl-N—[(4-methoxy-6-methyl-1,3,5-triazin-2-yl)-aminocarbonyl]benzenesulfonamide | 5% |
| dimethylformamide | 95% |

The ingredients are combined and stirred to produce a solution, which can be used for low volume applications.

EXAMPLE 18

| Wettable Powder | |
|---|---|
| 2-Acetyl-N—[(4,6-dimethoxypyrimidin-2-yl)aminocarbonyl]benzenesulfonamide | 80% |
| sodium alkylnaphthalenesulfonate | 2% |
| sodium ligninsulfonate | 2% |
| synthetic amorphous silica | 3% |
| kaolinite | 13% |

The ingredients are thoroughly blended after grinding in a hammer mill to produce particles essentially all of which are under 100 microns in size; the material is reblended, sifted through a U.S.S. No. 50 sieve and packaged.

Utility

The compounds of Formula I are useful as herbicides. They may be applied either pre- or post-emergence for the control of undesired vegetation in noncrop areas. By properly selecting rate and time of application, compounds of this invention may be used to modify plant growth beneficially.

The precise amount of the compound of Formula I to be used in any given situation will vary according to the particular end result desired, the use involved, the weeds to be controlled, the soil type, the formulation and mode of application, weather conditions, etc. Since so many variables play a role, it is not possible to state a rate of application suitable for all situations. Broadly speaking, the compounds of this invention are used at levels of about 0.005 to 20 kg/ha with a preferred range of 0.01 to 10 kg/ha. The lower rates of the range will generally be selected for lighter soils, or in situations where maximum persistence is not necessary. Some of the compounds of Formula I can be used at very low rates for plant growth modification, but higher rates may also be useful, depending on factors such as the crop being treated, timing of treatment, etc.

The compounds of Formula I may be combined with other herbicides and are particularly useful in combination with 3-(3,4-dichlorophenyl)-1,1-dimethylurea, the triazines such as 2-chloro-4-(ethylamino)-6-(isopropylamino)-s-triazine, the uracils such as 5-bromo-3-sec-butyl-6-methyluracil, N-(phosponomethyl)glycine, 3-cyclohexyl-1-methyl-6-dimethylamino-s-triazine-2,4(1H,3H)dione, 2,4-dichlorophenoxyacetic acid (and closely related compounds), 4-amino-6-tert-butyl-3-(methylthio)-1,2,4-triazin-5(4H)-one (Lexone®), 3-(3,4-dichlorophenyl)-1-methoxy-1-methylurea (Lorox®), 1,1′-dimethyl-4,4′-bipyridinium ion, monosodium methanearsonate, and 1,1-dimethyl-3-(α,α,α-trifluoro-m-tolyl)urea (Cotoran®).

The activity of these compounds was discovered in a greenhouse test. The test is described and the data resulting from it is shown below.

Test Procedure A

Seeds of crabgrass (Digitaria sp.), barnyardgrass (*Echinochloa crusgalli*), wild oats (*Avena fatua*), *Cassia tora*, morningglory (Ipomoea sp.), cocklebur (Xanthium sp.), sorghum, corn, soybean, rice, wheat and nutsedge tubers were planted in a growth medium and treated pre-emergence with the chemicals dissolved in a non-phytotoxic solvent. At the same time, cotton having five leaves (including cotyledonary ones), bushbeans with the third trifoliolate leaf expanding, crabgrass with two leaves, barnyardgrass with two leaves, wild oats with one leaf, cassia with three leaves (including cotyledonary ones), morningglory with four leaves (including cotyledonary ones), cocklebur with four leaves (including the cotyledonary ones), sorghum with three leaves, corn with three leaves, soybean with two cotyledonary leaves, rice with two leaves, wheat with one leaf, and nutsedge with three-five leaves were sprayed. Treated plants and controls were maintained in a greenhouse for 16 days, then all species were compared to controls and visually rated for response to treatment.

Ratings for compounds tested by this procedure are recorded in Table A.

TABLE A

| | 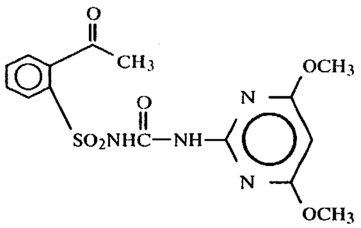 | 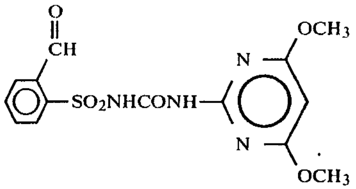 | 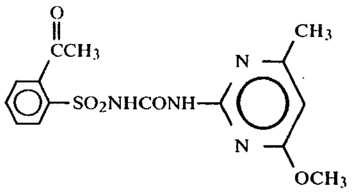 | 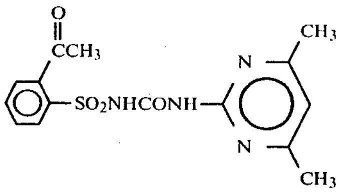 |
|---|---|---|---|---|
| kg/ha | .1 | 0.05 | 0.05 | 0.05 |
| POST-EMERGENCE | | | | |
| BUSHBEAN | 9C | 9C | 9D,9G,6Y | 9C |
| COTTON | 9C | 9C | 9C | 10C |
| MORNINGGLORY | 10C | 5C,8G | 9C | 9C |
| COCKLEBUR | 9C | 2C,5G | 9C | 9C |
| CASSIA | 9C | 9C | 9C | 9C |
| NUTSEDGE | 9C | 9C | 7C,9G | 9C |
| CRABGRASS | 2C,7G | 2C,5G | 9C | 9C |
| BARNYARDGRASS | 9C | 3C,9H | 9C | 10C |
| WILD OATS | 9C | 2C,5G | 5C,9G | 5C |
| WHEAT | 4C,9G | 1C | 3C,9G | 5C |
| CORN | 5U,9C | 2C,9H | 9C | 9C |
| SOYBEAN | 9C | 5C,9G | 9C | 9C |
| RICE | 9C | 5C,8G | 9C | 9C |
| SORGHUM | 9C | 1U,9H | 9C | 9C |
| PRE-EMERGENCE | | | | |
| MORNINGGLORY | 9G | 9G | 9C | 2C,9G |
| COCKLEBUR | 9G | 9H | 9G | 9H |
| CASSIA | 9G | 2C,8G | 9C | 9C |
| NUTSEDGE | 10E | 10E | 10E | 10E |
| CRABGRASS | 3G | 2C,4G | 3C,9G | 10E |
| BARNYARDGRASS | 9H | 2C,9H | 9H | 5C,9H |
| WILD OATS | 9H | 1C,8G | 5C,9G | 3C,9H |
| WHEAT | 9H | 8G | 10E | 10E |
| CORN | 5C,9G | 1C,9G | 10E | 10E |
| SOYBEAN | 9H | 8H | 9H | 9H |
| RICE | 10E | 10E | 10E | 10E |
| SORGHUM | 9H | 2C,9G | 10H | 10H |

O = no effect
10 = maximum effect
C = chlorosis or necrosis
E = emergence inhibition
G = growth retardation
H = formative effects
U = unusual pigmentation
6Y = abscised buds or flowers

Test B

Two bulb pans were filled with fertilized and limed Fallsington silt loam soil. One pan was planted with seeds of corn, sorghum, Kentucky bluegrass and several grassy weeds. The other pan was planted with seeds of soybeans, purple nutsedge tubers (*Cyperus rotundus*), and seeds of several broadleaf weeds. Seeds of the following grassy and broadleaf weeds were planted: crabgrass (*Digitaria sanguinalis*), barnyardgrass (*Echinochloa crusgalli*), wild oats (Avena fatua), johnsongrass (*Sorghum halepense*), giant foxtail (*Setaria faberii*), dallisgrass (*Paspalum dilatatum*), cheatgrass (*Bromus secalinus*), mustard (*Brassica arvensis*), cocklebur (*Xanthium pennsylvanicum*), pigweed (*Amaranthus retroflexus*), morningglory (*Ipomoea hederacea*), cassia (*Cassia tora*), teaweed (*Sida spinosa*), velvetleaf (*Abutilon theophrasti*), and jimsonweed (*Datura stramonium*). A smaller pot was also filled with prepared soil and planted with rice and wheat seeds. Another small pot was planted with seeds of sugarbeets. The above four containers were treated preemergence with nonphytotoxic solvent solutions of the compounds of this invention (i.e., solutions of said compound were sprayed on the soil surface before seed germination). Duplicates of the abovedescribed seeded containers were prepared without treatment and used as controls.

Twenty-eight days after treatment, the treated and control plants were evaluated and the data recorded are as set forth in Table B.

TABLE B

PRE-EMERGENCE ON FALLSINGTON SILT LOAM

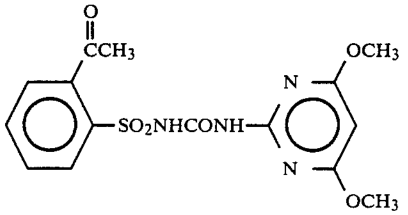

| Rate kg/ha | 0.125 | 0.03 |
|---|---|---|
| PRE-EMERGENCE | | |
| RICE | 10C | 8G,3H |
| BARNYARDGRASS | 9G,9C | 8G,5H |
| WHEAT | 7G | 5G |
| WILD OATS | 5E,7G | 6G |
| CRABGRASS | 6G | 5G |
| SORGHUM | 9G,9C | 7G,5H |
| JOHNSONGRASS | 9G,3H | 7G,3H |
| DALLASGRASS | 5G | 4G |
| GIANT FOXTAIL | 7G | 4G |
| BLUEGRASS | 8G,8C | 8G,8C |
| CHEATGRASS | 9C,9G | 7G,3C |
| CORN | 8G,7C | 3C,5G |
| MUSTARD | 10C | 10C |
| COCKLEBUR | 4G | 4G |
| PIG WEED | 9G,9C | 8G,5C |
| NUTSEDGE | 10E | 7G |
| COTTON | 7G | 5G |
| MORNINGGLORY | 5G | 5G |
| CASSIA | 8G | 7G |
| TEAWEED | 7G,3H | 4G |
| VELVET LEAF | 5H,9G | 8G,5H |
| JIMSON WEED | 8G | 7G |
| SOYBEAN | 7G,5H | 6G,5H |
| SUGAR BEET | 8G,9C | 4G |

TABLE B-continued

PRE-EMERGENCE ON FALLSINGTON SILT LOAM

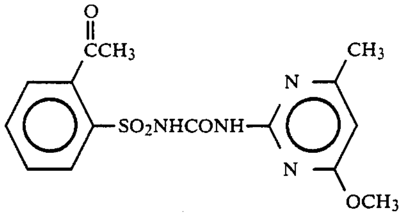

| Rate kg/ha | 0.125 | 0.03 | 0.015 | 0.008 |
|---|---|---|---|---|
| PRE-EMERGENCE | | | | |
| RICE | — | 10E | 10E | 9G,9C |
| BARNYARDGRASS | — | 9G,9C | 9G | 8G,3H |
| WHEAT | — | 7G,8C | 7G | 7G |
| WILD OATS | — | 7G,9C | 7G | 7G |
| CRABGRASS | 9G,8C | 9G,8C | 8G | 7G |
| SORGHUM | — | 10E | 10C | 10C |
| JOHNSONGRASS | — | 9C,9G | 9G | 9G,5H |
| DALLASGRASS | — | 8G,7C | 8G | 7G |
| GIANT FOXTAIL | — | 8G,5H | 9G | 8G,5H |
| BLUEGRASS | — | 9G,9C | 7G | 7G,5C |
| CHEATGRASS | — | 10E | 10C | 10E |
| CORN | — | 8G,4C | 8G | 5H,8G |
| MUSTARD | — | 10E | 10C | 10C |
| COCKLEBUR | — | 4G | 7G | 6G |
| PIG WEED | — | 10C | 9G | 10C |
| NUTSEDGE | — | 7C | 8G | 8G |
| COTTON | — | 3H,6G | 9G | 8G |
| MORNINGGLORY | — | 10C | 9G | 9G,6C |
| CASSIA | — | 9G,8C | 9G | 9G,8C |
| TEAWEED | 9G,8C | 7G,3C | 6G | 5G |
| VELVET LEAF | 10C | 8G | 10C | 6G,3H |
| JIMSON WEED | 10C | 9G,8C | 8G | 9G,7C |
| SOYBEAN | 8G,8C | 6G,3H | 7G | 7G,5H |
| SUGAR BEET | — | 10C | 9G | 8G,9C |

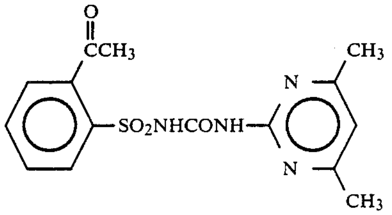

| Rate kg/ha | 0.125 | 0.03 | 0.015 | 0.008 |
|---|---|---|---|---|
| PRE-EMERGENCE | | | | |
| RICE | 10E | — | 10E | 10E |
| BARNYARDGRASS | — | 9G,9C | 9G,5H | 8G,5H |
| WHEAT | — | — | 6G | 4G |
| WILD OATS | 5E | 7G,5E | 7G | 8G |
| CRABGRASS | — | 9G,3C | 8G | 7G |
| SORGHUM | — | 10C | 10E | 10C |
| JOHNSONGRASS | 10C | 10C | 9G,5H | 8G,5H |
| DALLASGRASS | — | — | 8G | 7G |
| GIANT FOXTAIL | 10C | — | 9G,9C | 9G,5H |
| BLUEGRASS | 9G | — | 8G,7C | 5G,7C |
| CHEATGRASS | — | — | 10C | 10E |
| CORN | — | — | 7G,5H | 5H,7G |
| MUSTARD | 10E | 10E | 10C | 10C |
| COCKLEBUR | 7G,3H | 6G | 6G | 4G |
| PIG WEED | 10E | 8G,8C | 9G,8C | 9G,9C |
| NUTSEDGE | 10E | 10E | 8G | 8G |
| COTTON | 9G,3C | 9G | 9G,3C | 8G |
| MORNINGGLORY | 10C | 8G,3C | 9G,8C | 9G,6C |
| CASSIA | 10C | 9G,9C | 9G,9C | 9G,8C |
| TEAWEED | 10C | 6G | 7G,3C | 6G |
| VELVET LEAF | 9G | 8G | 10C | 9G,8C |
| JIMSON WEED | 9G,8C | 7G,5C | 9G,8C | 7G,8C |
| SOYBEAN | 9G,7C | 7G,5H | 8G,5H | 6G,5H |
| SUGAR BEET | — | — | 9G,9C | 9G,9C |

Test C

Twenty-five cm diameter plastic pots filled with Fallsington silt loam were planted with soybeans, cotton, alfalfa, corn, rice, wheat, sorghum, velvetleaf (*Abutilon theophrasti*), sesbania (*Sesbania exaltata*), Cassia (*Cassia tora*), morningglory (*Ipomoea hederacea*), jimsonweed (*Datura stramonium*), cocklebur (*Xanthium pennsylvanicum*), carbgrass (Digitaria spp.), nutsedge (*Cyperus rotundus*), barnyardgrass (*Echinochloa crus-galli*), giant foxtail (*Setaria faberii*) and wild oats (*Avena fatua*). Approximately two weeks after planting, the young plants and the soil around them were sprayed overall with the test chemicals dissolved in a non-phytotoxic solvent. Other groups of all the same weed and crop plants were sprayed with the same non-phytotoxic solvent so as to provide control plants. Two weeks after treatment, all species were compared to untreated controls and visually rated for response to treatment. The rating system was as described previously for Test A. The data are presented in Table C. Several of the compounds tested by this procedure are useful for the postemergence control of weeds in wheat and rice.

TABLE C

OVER THE TOP SOIL/FOLIAGE TREATMENT

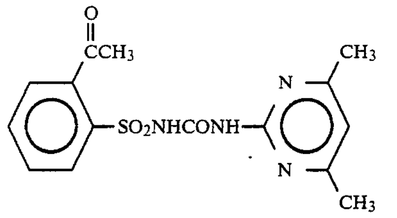

| Rate kg/ha | 0.06 | 0.015 | 0.004 |
|---|---|---|---|
| POST-EMERGENCE | | | |
| SOYBEAN | 10C | 9G,9C | 9G,9C |
| CORN | 10G,10U | 10G,10U | 5G,3U |
| COTTON | 10C | 7G,5C | 6G,1C |
| RICE | 6G,7C | 6G,5C | 6G,3C |
| WHEAT | 6G,1U | 4G,2C | 3G |
| VELVETLEAF | 9G,8C | 9G,8C | 8G,2C |
| SESBANIA | 9G,9C | 10C | 8G,5C |
| CASSIA | 7G,5C | 6G,2C | 4G,1C |
| MORNINGGLORY | 6G,5C | 3C,6G | 5G,2C |
| ALFALFA | 8G | 6G,3C | 4G |
| JIMSONWEED | 8G | 8G | 7G |
| COCKLEBUR | 10C | 8G | 7G |
| CRABGRASS | 9G,4C | 8G | 1G |
| BARNYARD GRASS | 9G,9C | 9G,9C | 9G,8C |
| GIANT FOXTAIL | 9G,7C | 7G | 5G |
| WILD OATS | 7G,7C | 7G,3C | 6G,1C |
| SORGHUM | 9G,8C | 7G,7U | 6G,6U |
| NUTSEDGE | 7G,8C | 7G,5C | 7G,3C |

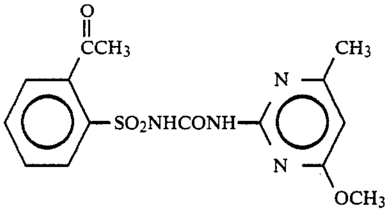

| Rate kg/ha | 0.06 | 0.015 |
|---|---|---|
| POST-EMERGENCE | | |
| SOYBEAN | 10G,8C | 10G,8C |
| CORN | 10G,7C | 10G,9U |
| COTTON | 10G,6C | 7G,3C |
| RICE | 10G,7C | 10G,7C |
| WHEAT | 9C | 5G,3C |

TABLE C-continued

OVER THE TOP SOIL/FOLIAGE TREATMENT

| | | |
|---|---|---|
| VELVETLEAF | 10G,8C | 10G, C |
| SESBANIA | 10G,9C | 10G,8C |
| CASSIA | 10G,7C | 10G,7C |
| MORNINGGLORY | 9G,7C | 9G,7C |
| ALFALFA | | — |
| JIMSONWEED | 10G,7C | 8G,6C |
| COCKLEBUR | 10G,9C | 8G,3C |
| CRABGRASS | 10G,5C | 7G,2C |
| BARNYARD GRASS | 10C | 10C |
| GIANT FOXTAIL | — | — |
| WILD OATS | 9C | 9C |
| SORGHUM | 10C | 10G,6C |
| NUTSEDGE | — | 8G,4C |

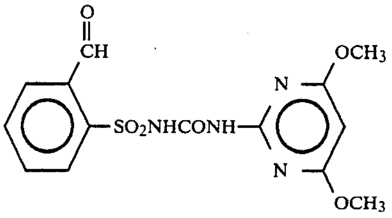

| Rate kg/ha | 0.06 | 0.015 |
|---|---|---|
| POST-EMERGENCE | | |
| SOYBEAN | 10G,7C | 10G,7C |
| CORN | 8G,6H | 7G,5H |
| COTTON | 6G,3C | 4G,2C |
| RICE | 7G,4C | 5G |
| WHEAT | 0 | 0 |
| VELVETLEAF | 5G,3C | 4C,1C |
| SESBANIA | 10G,6C | 8G,3C |
| CASSIA | 4G,3C | 3G,1C |
| MORNINGGLORY | 7G,3C | 1C |
| ALFALFA | 7G,3C | 3G |
| JIMSONWEED | 8G,1C | 4G,2C |
| COCKLEBUR | — | 5G,1C |
| CRABGRASS | 3G,1C | 0 |
| BARNYARD GRASS | 8G,4C | 6G,2C |
| GIANT FOXTAIL | — | 2G |
| WILD OATS | 1G | 1C |
| SORGHUM | 8G,3C | 7G,2U |
| NUTSEDGE | 7G,3C | 3C |

What is claimed is:

1. A compound of the formula:

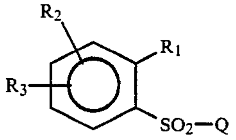

where $R_1$ is

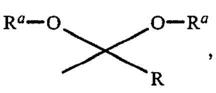
,
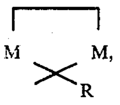

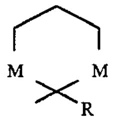
or
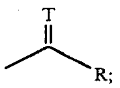

M=O or $S(O)_G$;

G=0 or 2;

$R^a$ is $CH_3$ or $CH_3CH_2$;

R=H; $C_1$–$C_{12}$ alkyl; $C_2$–$C_6$ alkenyl; $C_2$–$C_6$ alkynyl; $C_1$–$C_4$ alkyl substituted with one to four substituents selected from 0-3 F, 0-3 Cl, 0-3 Br, 0-2 $OCH_3$, 0-1 cyano, 0-1 $CO_2R_1'$ where $R_1'$ is $C_1$–$C_3$ alkyl; $CO_2R_1'$; $C_2$–$C_4$ alkenyl substituted with 1-3 Cl; $C_3$–$C_6$ cycloalkyl; $C_5$–$C_6$ cycloalkenyl; $C_5$–$C_6$ cycloalkyl substituted with substituents selected from 1-3 $CH_3$ or one of $CH_3CH_2$, Cl, $OCH_3$; $C_4$–$C_7$ cycloalkylalkyl;

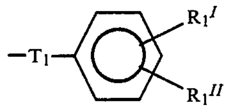

where $T_1$ is

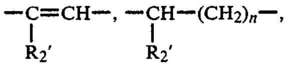

or a single bond;

where $R_2'$ is H or $CH_3$, n is 0 or 1;

$R_1^I$ and $R_1^{II}$ are independently H, $CH_3$, Cl or $OCH_3$;

T=O or

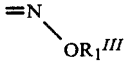

where $R_1^{III}$ is H, $C_1$–$C_4$ alkyl or $C_3$–$C_4$ alkenyl;

$R_2$=H, F, Cl, Br, $C_1$–$C_3$ alkyl, $NO_2$, $SO_2CH_3$, $OCH_3$, $SCH_3$, $CF_3$ or $N(CH_3)_2$;

$R_3$=H, F, Cl, Br or $CH_3$;

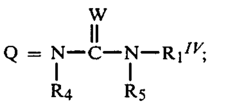

where $R_4$=H or $CH_3$;

$R_5$=H, $CH_3$ or $OCH_3$;

W=O or S;

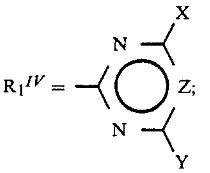

where

Z=N;

X=H, Cl, $-CH_3$, $-OCH_3$, $-OCH_2CH_3$ or $-OCH_2CH_2OCH_3$;

Y=H; Cl; $C_1$–$C_4$ alkyl; $C_1$–$C_4$ alkyl substituted with $-OCH_3$, $-OC_2H_5$, —CN, $-CO_2CH_3$, $-CO_2C_2H_5$ or 1-3 atoms of F, Cl, Br; $C_3$–$C_4$ alkenyl; $-CH_2C\equiv CR_6$ where $R_6$ is H, $-CH_3$, $-CH_2Cl$; $-A-(CH_2)_{n'}-A_1-(C_1-C_3$ alkyl) where n' is 2 or 3, A is O or S and $A_1$ is O, S or $SO_2$;

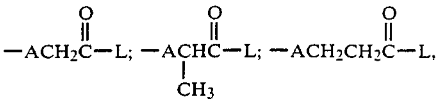

L is OH, $-NH_2$,

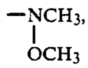

—NH($C_1$–$C_4$ alkyl), —N($C_1$–$C_4$ alkyl)$_2$, $C_1$–$C_6$ alkoxy; SCN; $-N_3$; $NR_7R_8$ where $R_7$ is H or $CH_3$ and $R_8$ is H, $-OCH_3$, $C_1$–$C_4$ alkyl, $C_3$–$C_6$ cycloalkyl, $C_1$–$C_4$ alkyl substituted with —CN or $-CO_2CH_3$ or $CO_2C_2H_5$, $C_3$–$C_4$ alkenyl or $C_2$–$C_3$ alkyl substituted with $OCH_3$ or $OC_2H_5$, or $R_7$ and $R_8$ can be taken together to form $-CH_2CH_2CH_2CH_2-$ or $-CH_2CH_2OCH_2CH_2-$; $-O-R_9$ where $R_9$ is $C_1$–$C_4$ alkyl, $C_2$–$C_4$ alkyl substituted with 1-3 atoms of F, Cl or Br, $C_1$–$C_4$ alkyl substituted with cyano, $C_3$–$C_4$ alkenyl, $-CH_2C\equiv CR_6$, where $R_6$ is as previously defined,

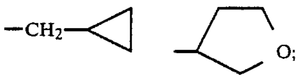

$-SR_{10}$ where $R_{10}$ is $C_1$–$C_4$ alkyl, $C_1$–$C_2$ alkyl substituted with CN, allyl or propargyl;

with the provisos that:

(1) when Y contains ≦4 carbon atoms, R contains ≦4 carbon atoms;

(2) when X is Cl, then Y is Cl;

(3) when X and Y are both H, ten R is ≦4 carbon atoms;

(4) when T is $-N-OR_1^{III}$, then R contains ≦5 carbon atoms; and their agriculturally suitable salts.

2. A composition of claim 1 where

X is $CH_3$, $OCH_3$ or $OCH_2CH_3$ and Y is H, $C_1$–$C_3$ alkyl, $CH_2OCH_3$, $CH_2OCH_2CH_3$, $-OCH_2CO_2-(C_1-C_2$ alkyl),

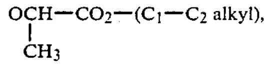

O—($C_1$–$C_3$ alkyl), O—($C_3$–$C_4$ alkenyl), $NR_7R_8$ where $R_7$ is H or $CH_3$ or $R_8$ is $C_1$–$C_3$ alkyl.

3. A composition of claim 1 where

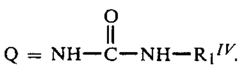

4. A composition of claim 1 where T=O.

5. A composition of claim 1 where $R_1$ is 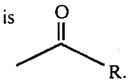

6. A composition of claim 1 where R is H or $C_1$–$C_4$ alkyl.

7. A compound of claim 1 wherein $R_4$ and $R_5$ are H and W is oxygen.

8. A compound of claim 1 wherein $R_2$ is H, F, Cl, Br, $C_1$–$C_3$ alkyl or $OCH_3$ and $R_3$ is H para to the sulfonyl group.

9. The compound of claim 1 is 2-acetyl-N-[(4-methoxy-6-methyl-1,3,5-triazin-2-yl)aminocarbonyl]-benzenesulfonamide.

10. The composition of claim 11 where the compound is 2-acetyl-N-[(4-methoxy-6-methyl-1,3,5-triazin-2-yl)aminocarbonyl]-benzenesulfonamide.

11. A composition suitable for controlling the growth of undesired vegetation which comprises an effective amount of a compound selected from

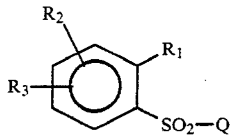

where $R_1$ is

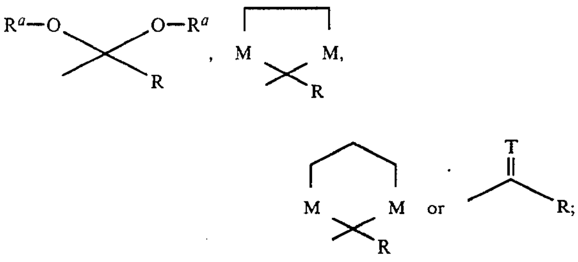

M=O or $S(O)_G$;

G=0 or 2;

$R^a$ is $CH_3$ or $CH_3CH_2$;

R=H; $C_1$–$C_{12}$ alkyl; $C_2$–$C_6$ alkenyl; $C_2$–$C_6$ alkynyl; $C_1$–$C_4$ alkyl substituted with one to four substituents selected from 0–3 F, 0–3 Cl, 0–3 Br, 0–2 $OCH_3$, 0–1 cyano, 0–1 $CO_2R_1'$ where $R_1'$ is $C_1$–$C_3$ alkyl; $CO_2R_1'$; $C_2$–$C_4$ alkenyl substituted with 1–3 Cl; $C_3$–$C_6$ cycloalkyl; $C_5$–$C_6$ cycloalkenyl; $C_5$–$C_6$ cycloalkyl substituted with substituents selected from 1–3 $CH_3$ or one of $CH_3CH_2$, Cl, $OCH_3$; $C_4$–$C_7$ cycloalkylalkyl;

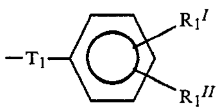

where $T_1$ is

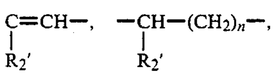

or a single bond;

where $R_2'$ is H or $CH_3$, n is 0 or 1;

$R_1^I$ and $R_1^{II}$ are independently H, $CH_3$, Cl or $OCH_3$;

T=O or

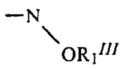

where $R_1^{III}$ is H, $C_1$–$C_4$ alkyl or $C_3$–$C_4$ alkenyl;

$R_2$=H, F, Cl, Br, $C_1$–$C_3$ alkyl, $NO_2$, $SO_2CH_3$, $OCH_3$, $SCH_3$, $CF_3$ or $N(CH_3)_2$;

$R_3$=H, F, Cl, Br or $CH_3$;

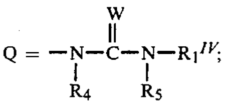

where $R_4$=H or $CH_3$;

$R_5$=H, $CH_3$ or $OCH_3$;

W=O or S;

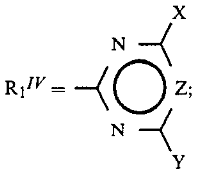

where

Z=N;

X=H, Cl, $-CH_3$, $-OCH_3$, $-OCH_2CH_3$ or $-OCH_2CH_2OCH_3$;

Y=H; Cl; $C_1$–$C_4$ alkyl; $C_1$–$C_4$ alkyl substituted with $-OCH_3$, $-OC_2H_5$, $-CN$, $-CO_2CH_3$, $-CO_2C_2H_5$ or 1–3 atoms of F, Cl, Br; $C_3$–$C_4$ alkenyl; $-CH_2C{\equiv}CR_6$ where $R_6$ is H, $-CH_3$, $-CH_2Cl$; $-A-(CH_2)_{n'}-A_1-(C_1$–$C_3$ alkyl) where n' is 2 or 3, A is O or S and $A_1$ is O, S or $SO_2$;

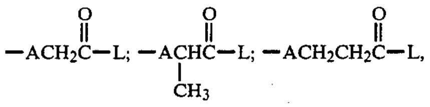

where

L is OH, $-NH_2$,

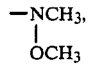

$-NH(C_1$–$C_4$ alkyl), $-N(C_1$–$C_4$ alkyl$)_2$, $C_1$–$C_6$ alkoxy; SCN; $-N_3$; $NR_7R_8$ where $R_7$ is H or $CH_3$ and $R_8$ is H, $-OCH_3$, $C_1$–$C_4$ alkyl, $C_3$–$C_6$ cycloalkyl, $C_1$–$C_4$ alkyl substituted with $-CN$ or $-CO_2CH_3$ or $CO_2C_2H_5$, $C_3$–$C_4$ alkenyl or $C_2$–$C_3$ alkyl substituted with $OCH_3$ or $OC_2H_5$, or $R_7$ and $R_8$ can be taken together to form $-CH_2CH_2CH_2CH_2-$ or $-CH_2CH_2OCH_2CH_2-$; $-O-R_9$ where $R_9$ is $C_1$–$C_4$ alkyl, $C_2$–$C_4$ alkyl substituted with 1–3 atoms of F, Cl or Br, $C_1$–$C_4$ alkyl substituted with cyano, $C_3$–$C_4$ alkenyl, $-CH_2C{\equiv}CR_6$, where $R_6$ is as previously defined,

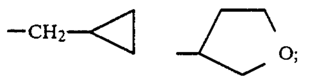

—$SR_{10}$ where $R_{10}$ is $C_1$–$C_4$ alkyl, $C_1$–$C_2$ alkyl substituted with CN, allyl or propargyl;

with the provisos that:

(1) when Y contains ≦4 carbon atoms, R contains ≦4 carbon atoms;

(2) when X is Cl, then Y is Cl;

(3) when X and Y are both H, then R is ≦4 carbon atoms;

(4) when T is —N—$OR_1^{III}$, then R contains ≦5 carbon atoms; and their agriculturally suitable salts and at least one of the following; surfactant, solid or liquid diluent.

12. A composition of claim 11 where $R_4$ and $R_5$ are H and W is oxygen.

13. A composition of claim 12 where $R_2$ is H, F, Cl, Br, $C_1$-$C_3$ alkyl, $OCH_3$ and $R_3$ is H in the position para to the sulfonyl group.

14. A composition of claim 13 where $R_1$ is

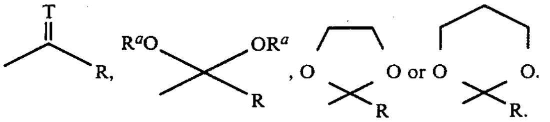

15. A composition of claim 14 where

R is H, $C_1$-$C_6$ alkyl, $C_2$-$C_6$ alkenyl, $C_3$-$C_6$ cycloalkyl, or

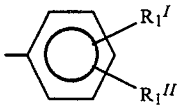

where $R_1^I$ and $R_1^{II}$ are independently H, $CH_3$, Cl or $OCH_3$.

16. A method for controlling the growth of undesired vegetation which comprises applying to the locus to be protected an effective amount of a compound selected from

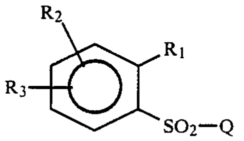

where $R_1$ is

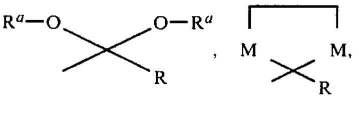

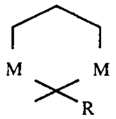

or

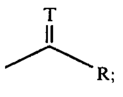

M=O or $S(O)_G$;

G=0 or 2;

$R^a$ is $CH_3$ or $CH_3CH_2$;

R=H; $C_1$-$C_{12}$ alkyl; $C_2$-$C_6$ alkenyl; $C_2$-$C_6$ alkynyl; $C_1$-$C_4$ alkyl substituted with one to four substituents selected from 0-3 F, 0-3 Cl, 0-3 Br, 0-2 $OCH_3$, 0-1 cyano, 0-1 $CO_2R_1'$ where $R_1'$ is $C_1$-$C_3$ alkyl; $CO_2R_1'$; $C_2$-$C_4$ alkenyl substituted with 1-3 Cl; $C_3$-$C_6$ cycloalkyl; $C_5$-$C_6$ cycloalkenyl; $C_5$-$C_6$ cycloalkyl substituted with substituents selected from 1-3 $CH_3$ or one of $CH_3CH_2$, Cl, $OCH_3$; $C_4$-$C_7$ cycloalkylalkyl;

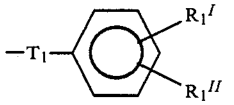

where $T_1$ is

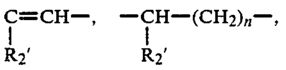

or a single bond;

where $R_2'$ is H or $CH_3$, n is 0 or 1;

$R_1^I$ and $R_1^{II}$ are independently H, $CH_3$, Cl or $OCH_3$;

T=O or

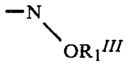

where $R_1^{III}$ is H, $C_1$-$C_4$ alkyl or $C_3$-$C_4$ alkenyl;

$R_2$=H, F, Cl, Br, $C_1$-$C_3$ alkyl, $NO_2$, $SO_2CH_3$, $OCH_3$, $SCH_3$, $CF_3$ or $N(CH_3)_2$;

$R_3$=H, F, Cl, Br or $CH_3$;

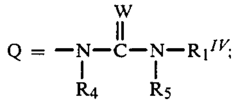

where $R_4$=H or $CH_3$;

$R_5$=H, $CH_3$ or $OCH_3$;

W=O or S;

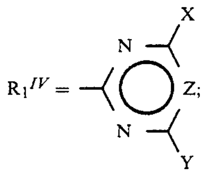

where

Z=N;

X=H, Cl, —$CH_3$, —$OCH_3$, —$OCH_2CH_3$ or —$OCH_2CH_2OCH_3$;

Y=H; Cl; $C_1$-$C_4$ alkyl; $C_1$-$C_4$ alkyl substituted with —$OCH_3$, —$OC_2H_5$, —CN, —$CO_2CH_3$, —$CO_2C_2H_5$ or 1-3 atoms of F, Cl, Br; $C_3$-$C_4$ alkenyl; —$CH_2C≡CR_6$ where $R_6$ is H, —$CH_3$, —$CH_2Cl$; —A—$(CH_2)_{n'}$—$A_1$—($C_1$-$C_3$ alkyl)

where n' is 2 or 3, A' is O or S and $A_1$ is O, S or $SO_2$;

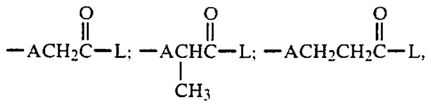

where L is OH, $-NH_2$,

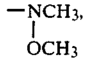

$-NH(C_1-C_4$ Alkyl), $-N(C_1-C_4$ alkyl$)_2$, $C_1-C_6$ alkoxy; SCN; $-N_3$; $NR_7R_8$ where $R_7$ is H or $CH_3$ and $R_8$ is H, $-OCH_3$, $C_1-C_4$ alkyl, $C_3-C_6$ cycloalkyl, $C_1-C_4$ alkyl substituted with $-CN$ or $-CO_2CH_3$ or $CO_2C_2H_5$, $C_3-C_4$ alkenyl or $C_2-C_3$ alkyl substituted with $OCH_3$ or $OC_2H_5$, or $R_7$ and $R_8$ can be taken together to form $-CH_2CH_2CH_2CH_2-$ or $-CH_2CH_2OCH_2CH_2-$; $-O-R_9$ where $R_9$ is $C_1-C_4$ alkyl, $C_2-C_4$ alkyl substituted with 1-3 atoms of F, Cl or Br, $C_1-C_4$ alkyl substituted with cyano, $C_3-C_4$ alkenyl, $-CH_2C\equiv CR_6$, where $R_6$ is as previously defined,

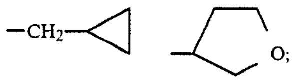

$-SR_{10}$ where $R_{10}$ is $C_1-C_4$ alkyl, $C_1-C_2$ alkyl substituted with CN, allyl or propargyl;

with the provisos that:

(1) when Y contains $\leqq 4$ carbon atoms, R contains $\leqq 4$ carbon atoms;

(2) when X is Cl, then Y is Cl;

(3) when X and Y are both H, then R is $\leqq 4$ carbon atoms;

(4) when T is $-N-OR_1^{III}$, then R contains $\leqq 5$ carbon atoms; and their agriculturally suitable salts.

17. A method of claim 16 where $R_4$ and $R_5$ are H and W is oxygen.

18. A method of claim 17 where $R_2$ is H, F, Cl, Br, $C_1-C_3$ alkyl, $OCH_3$ and $R_3$ is H in the position para to the sulfonyl group.

19. A method of claim 18 where

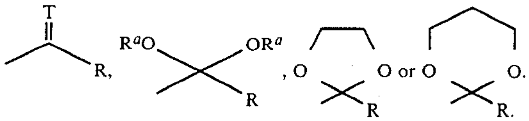

20. A method of claim 19 where R is H, $C_1-C_6$ alkyl, $C_2-C_6$ alkenyl, $C_3-C_6$ cycloalkyl, or

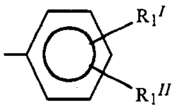

where $R_1^I$ and $R_1^{II}$ are independently H, $CH_3$, Cl or $OCH_3$.

21. A method of claim 20 where X is $CH_3$, $OCH_3$ or $OCH_2CH_3$ and Y is H, $C_1-C_3$ alkyl, $CH_2OCH_3$, $CH_2OCH_2CH_3$, $-OCH_2CO_2-(C_1-C_2$ alkyl),

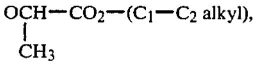

$O-(C_1-C_3$ alkyl), $O-(C_3-C_4$ alkenyl), $NR_7R_8$ where $R_7$ is H or $CH_3$ or $R_8$ is $C_1-C_3$ alkyl.

22. A method of claim 21 where

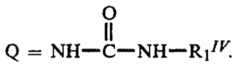

23. A method of claim 22 where T=0.

24. A method of claim 23 where $R_1$ is 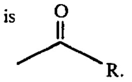

25. A method of claim 24 where R is H or $C_1-C_4$ alkyl.

26. The method of claim 16, where the compound is 2-acetyl-N-[(4-methoxy-6-methyl-1,3,5-triazin-2-yl)aminocarbonyl]-benzenesulfonamide.

* * * * *